(12) United States Patent
O'Shea

(10) Patent No.: US 8,907,107 B2
(45) Date of Patent: Dec. 9, 2014

(54) FLUORESCENT NEAR INFRA-RED (NIR) DYES

(75) Inventor: Donal O'Shea, Dublin (IE)

(73) Assignee: Hae Therapeutics Limited, Dublin (IE)

( * ) Notice: Subject to any disclaimer, the term of this patent is extended or adjusted under 35 U.S.C. 154(b) by 191 days.

(21) Appl. No.: 13/503,195

(22) PCT Filed: Oct. 22, 2010

(86) PCT No.: PCT/EP2010/065991
§ 371 (c)(1),
(2), (4) Date: May 21, 2012

(87) PCT Pub. No.: WO2011/048217
PCT Pub. Date: Apr. 28, 2011

(65) Prior Publication Data
US 2012/0232282 A1  Sep. 13, 2012

(30) Foreign Application Priority Data
Oct. 23, 2009 (IE) .................................. S2009/0823

(51) Int. Cl.
*C07F 5/02* (2006.01)

(52) U.S. Cl.
CPC ...................................... *C07F 5/022* (2013.01)
USPC ........................................................ 548/405

(58) Field of Classification Search
CPC ...................................................... C07F 5/022
USPC ........................................................ 548/405
See application file for complete search history.

(56) References Cited

FOREIGN PATENT DOCUMENTS

WO    WO 03/080627 A1    10/2003
WO    WO 2006/058448 A1    6/2006

OTHER PUBLICATIONS

Yuan et al. "Light Harvesting and Efficient Energy Transfer in Dendritic Systems: New Strategy for Functionalized Near-Infrared BF2-Azadipyrromethenes" Chemistry—An Asian Journal, 2009, vol. 4, pp. 707-713.*

International Search Report and Written Opinion of the International Searching Authority mailed Mar. 7, 2011 in connection with International Application No. PCT/EP2010/065991.
Tasior, M. et al. "BF2-chelated tetraarylazadipyrromethenes as NIR fluorochromes", Bioconjugate Chemistry, vol. 21, No. 7, Jul. 21, 2010, pp. 1130-1133.
Tasior M. et al. "Water-solubilised BF2-chelated tetraarylazadpyrromethenes", Organic & Biomolecular Chemistry, vol. 8, No. 3, Feb. 7, 2010, pp. 522-525.
Murtagh J et al. "Azide conjugatable and pH responsive near-infrared fluorescent imaging probes", Organic Letters, vol. 11, No. 23, Dec. 3, 2009, pp. 5386-5389.
Loudet A et al. "Functionalized BF2 chelated azadipyrromethene dyes", Tetrahedron, vol. 64, No. 17, Feb. 3, 2008, pp. 3642-3654.

* cited by examiner

*Primary Examiner* — Joseph Kosack
(74) *Attorney, Agent, or Firm* — Cesari and McKenna, LLP

(57) ABSTRACT

A compound of formula (I) is described in which each A, which may be the same or different, is a halide selected from fluoride, chloride, bromide and iodide, or is O—Y, wherein Y is a substituted or unsubstituted, saturated or unsaturated, straight or branched chain alkyl moiety. $R_1$, $R_2$, $R_3$, $R_6$, $R_7$, and $R_8$ are each independently H, OH, $NO_2$ or O-L-X, wherein L is a spacer group, and X is a conjugation group or a water-solubilizing group. At least one of $R_1$, $R_2$, $R_3$ is OH or O-L-X and at least one of $R_6$, $R_7$, and $R_8$ is OH or O-L-X. $R_4$ and $R_5$, which may be the same or different, are each independently H; or are a substituted or unsubstituted, saturated or unsaturated, cyclic moiety; a substituted or unsubstituted, saturated or unsaturated heterocyclic moiety; or a substituted or unsubstituted, saturated or unsaturated, straight or branched chain alkyl moiety. Also described are dye conjugates comprising a compound of the invention.

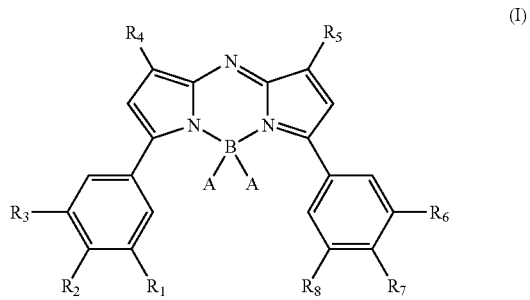

34 Claims, 28 Drawing Sheets

| Entry | Conjugate | $\lambda_{max}$abs nm$^a$ | $\lambda_{max}$emiss nm$^{a,b,c}$ |
|---|---|---|---|
| 1 | lysosyme | 690 | 720 |
| 2 | trypsin | 692 | 725 |

$^a$PBS pH 7.0 with 0.4% SDS. $^b$ excitation at 640 nm. $^c$slit widths 5 nm.

(circled area is blue)

FLUORESCENT NEAR INFRA-RED (NIR) DYES

CROSS REFERENCE TO RELATED APPLICATIONS

This application is a National Stage of International Application No. PCT/EP2010/065991, filed on Oct. 22, 2010, which claims priority to Irish Patent Application No. S2009/0823, filed Oct. 23, 2009. The contents of the prior applications are incorporated herein by reference in their entirety.

TECHNICAL FIELD

The invention relates to novel fluorescent near-infrared (NIR) dyes and to methods for preparing the dyes. The invention also relates to dye conjugates comprising the dyes of the invention covalently bound to molecules of interest.

BACKGROUND OF THE INVENTION

Fluorescent dyes, also referred to herein as fluorescent compounds, fluorophores and fluorochromes, have many useful applications. For example, fluorescence can be used as a non-destructive way of tracking or analysing many diverse molecules. Such molecules are labelled with a fluorescent dye, enabling the fluorescence of the dye to be detected.

In recent years there has been growing interest in visible red and near-infrared (NIR) fluorescent dyes (>700 nm) for qualitative and quantitative assays. Their simplicity of use, coupled with high sensitivity also ensures a continual expansion of their use for in vitro and in vivo imaging. In terms of commercial application, high sensitivity NIR fluorescence imaging has become an indispensable tool for probing the molecular processes of biological systems in living cells. Its application to non-invasive in vivo animal and human imaging is currently a re-emerging field with applications varying from vascular mapping to tumor diagnosis. NIR optical imaging of tissues is an inexpensive, real-time and non-invasive technique that does not require the use of radionuclides. Recently developed ultra sensitive low noise charge coupled cameras, mathematical models of photon propagation in tissue, and more target-specific molecular probes, have created exciting possibilities in this field. The inherent advantages of NIR fluorochromes over those that absorb in the shorter blue and green wavelengths lie in the dramatic reduction in background autofluorescence which leads to greatly improved sensitivity, increased light penetration of biological tissue, and minimal damaging of the cells/tissue under observation. As an example, in the case of in vivo imaging, it is strongly preferential to use fluorophores with absorption/emission profiles in the far visible red or near infrared spectral (NIR) regions (700 nm-1400 nm), as at lower wavelength, strong interference from endogenous chromophores is problematic.

Despite the optical benefits, there is a surprising scarcity of NIR compounds which have the desired absorption and emission properties. Among the fluorescent platforms used for the construction of visible red/NIR fluorescent probes for bioconjugation, the cyanine dyes are by far the most widely utilised. To date, of the cyanine dyes, only indocyanine green (ICG) has been approved for clinical use. Furthermore, despite their widespread use, the cyanine dyes have disadvantages, including poor photostability and lengthy synthetic routes.

The boron chelated tetraarylazadipyrromethene class of compounds has been found to be relatively easily synthesised and to exhibit excellent spectral properties. Their strong absorption and emissions within the NIR spectral region, together with high photostability make them promising candidates for biological imaging applications. For example, the compound 1 has an absorption $\lambda_{max}$ at 696 nm and emission at 727 nm ($\phi_F$=0.36) in formulated aqueous solutions, and absorption $\lambda_{max}$ at 688 nm ($\epsilon$=85,000 dm$^{-3}$ mol$^{-1}$ cm$^{-1}$) and emission at 716 nm ($\phi_F$=0.36) in chloroform.

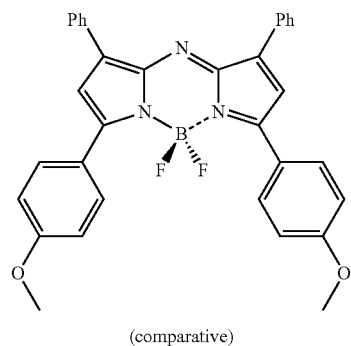

(comparative)

These promising photophysical characteristics have encouraged the adaption of this class to specific functions such as photodynamic therapy. WO 03/080627 discloses the use of these compounds 1 as photodynamic therapeutic agents. However, such compounds, although useful, also have disadvantages. For example, their commercial application has been limited to date by their inability to be bound to a molecule or particle of interest for tracking or analysing the molecule. Specifically, it is not feasible to add a conjugation group onto the carbon of the methoxy groups of the compound. For the above reasons, a distinct need exists for novel NIR fluorescent dyes.

It is an object of the invention to avoid or mitigate the problems associated with known NIR fluorescent dyes.

It is a further object of the invention to provide novel NIR fluorescent dyes that are stable and are capable of binding to a molecule or particle of interest.

It is a still further object of the invention to provide novel NIR fluorescent dyes that are water-soluble.

It is a still further object of the invention to provide novel NIR fluorescent dyes that have a predictable fluorescence intensity response to environmental changes, for example pH.

STATEMENTS OF THE INVENTION

According to the invention, there is provided a compound of the formula (I)

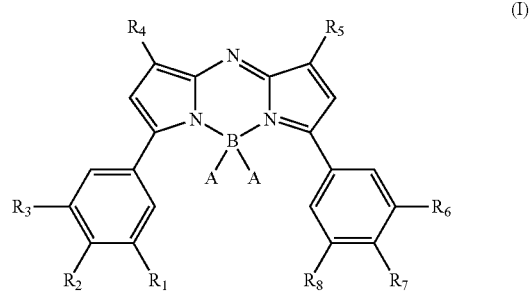

in which each A, which may be the same or different, is a halide selected from fluoride, chloride, bromide and iodide, or is O—Y, wherein Y is a substituted or unsubstituted, saturated or unsaturated, straight or branched chain alkyl moiety; $R_1$, $R_2$, $R_3$, $R_6$, $R_7$, and $R_8$ are each independently H, OH, $NO_2$ or O-L-X, wherein L is a spacer group, and X is a conjugation group or a water-solubilizing group; with the proviso that at least one of $R_1$, $R_2$, $R_3$ is OH or O-L-X and at least one of $R_6$, $R_7$, and $R_8$ is OH or O-L-X; and $R_4$ and $R_5$, which may be the same or different, are each independently H; or are a substituted or unsubstituted, saturated or unsaturated, cyclic moiety; a substituted or unsubstituted, saturated or unsaturated heterocyclic moiety; or a substituted or unsubstituted, saturated or unsaturated, straight or branched chain alkyl moiety.

As used herein, the term "cyclic" is intended to embrace substituted or unsubstituted, saturated or unsaturated, moieties containing one or more rings. If more than one ring is present, the rings may be fused together.

As used herein, the term "aryl", which is included within the scope of "cyclic", is intended to embrace substituted or unsubstituted, unsaturated, monocyclic or polycyclic (fused or separate) aromatic hydrocarbon moieties. Preferred monocyclic aromatic moieties include phenyl, substituted phenyl moieties including, but not limited to, tolyl, xylyl, mesityl, cumenyl (isopropyl phenyl) and substituted phenylene derivatives including, but not limited to, benzyl, benzhydryl, cinnamyl, phenethyl, styryl and trityl. Preferred fused polycyclic moieties include substituted and unsubstituted naphthalene and anthracene moieties.

As used herein, the term "heterocyclic" is intended to embrace substituted or unsubstituted, saturated or unsaturated, monocyclic or polycyclic (fused or separate) heterocyclic moieties. Suitable non-aromatic moieties are substituted or unsubstituted piperidine, dioxane, piperazine and pyrrolidine moieties.

As used herein, the term "heteroaryl", which is included within the scope of "heterocyclic", is intended to embrace substituted or unsubstituted, unsaturated, monocyclic or polycyclic (fused or separate) aromatic heterocyclic moieties. Preferred are substituted or unsubstituted pyridine, pyridazine, pyrimidine, pyrazine, purine, furan, pyrrole, benzofuran, indole and thiophene moieties.

As used herein, the term "aromatic" is intended to embrace a fully unsaturated, substituted or unsubstituted, cyclic moiety.

As used herein, the term "alkyl" is intended to embrace substituted or unsubstituted, straight or branched chain, saturated or unsaturated alkyl, alkenyl or alkynyl moieties having up to 25 carbon atoms. Preferred are alkyl moieties such as methyl, ethyl, propyl, isopropyl, butyl, isobutyl, sec-butyl, pentyl, isopentyl, hexyl, methylpentyl, isohexyl, heptyl, isoheptyl, octyl, isooctyl, nonyl, isononyl, decyl, isodecyl, undecyl, dodecyl, tridecyl, tetradecyl, pentadecyl, hexadecyl, heptadecyl, octodecyl, nonadecyl, icosyl, henicosyl, docosyl, tricosyl, tetracosyl and pentacosyl, all of which may be further substituted. Preferred alkenyl and alkynyl moieties include vinyl, ethynyl, allyl, isopropenyl, propynyl, butenyl, butynyl, pentenyl, pentynyl, hexenyl, hexynyl, heptenyl, heptynyl, octenyl, octynyl, nonenyl, nonynyl, decenyl, decynyl, undecenyl, undecynyl, dodecenyl, dodecynyl, tridecenyl, tridecynyl, tetradecenyl, tetradecynyl, pentadecenyl, pentadecynyl, hexadecenyl, hexadecynyl, heptadecenyl, heptadecynyl, octadecenyl (oleic or elaidic), octadecynyl, nonadecenyl, nonadecynyl, icosenyl, icosynyl, henicosenyl, henicosynyl, docosenyl, docosynyl, tricosenyl, tricosynyl, tetracosenyl, tetracosynyl, pentacosenyl and pentacosynyl, all of which may be further substituted.

When A is O—Y, Y is preferably a substituted or unsubstituted, saturated or unsaturated, straight or branched chain alkyl moiety having up to 10 carbon atoms, more preferably up to 5 carbon atoms. Preferably, Y is selected from methyl, ethyl, propyl, isopropyl, butyl and isobutyl, even more preferably selected from methyl or ethyl, most preferably methyl.

Preferably, each A is a halide. Most preferably, each A is fluoride.

Each of $R_4$ and $R_5$ may be, independently, a heterocyclic, preferably heteroaryl, moiety. Preferably, each of $R_4$ and $R_5$ is, independently, a cyclic, preferably an aryl, moiety, more preferably a monocyclic aryl moiety. These moieties may be substituted or unsubstituted. Most preferably, each of $R_4$ and $R_5$ is phenyl (Ph).

In an especially preferred embodiment, each A is F, $R_4$ is Ph and $R_5$ is Ph.

Included in compounds of the formula (I) are compounds of the formula (IA).

In compounds of the formula (IA),

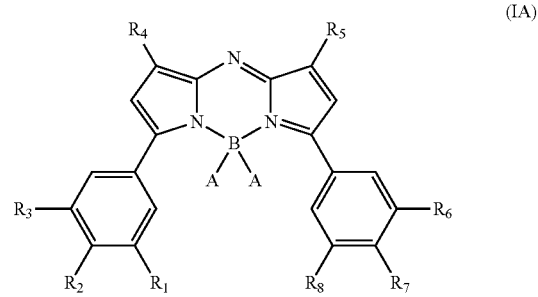

(IA)

each A and $R_4$ and $R_5$ are as defined above for compounds of the formula (I);

$R_1$, $R_2$, $R_3$, $R_6$, $R_7$, and $R_8$ are each independently H, OH, $NO_2$ or O-L-X, wherein L and X are as defined above for compounds of the formula (I); subject to the proviso as recited for compounds of the formula (I); and with the further proviso that at least one of $R_1$, $R_2$, $R_3$, $R_6$, $R_7$, and $R_8$ is O-L-X.

Preferably, only one of $R_1$, $R_2$, $R_3$ is OH or O-L-X, and the remaining groups of $R_1$, $R_2$ and $R_3$ are each independently H or $NO_2$; and/or only one of $R_6$, $R_7$, and $R_8$ is OH or O-L-X, and the remaining groups of $R_6$, $R_7$, and $R_8$ are each independently H or $NO_2$.

Preferably, when one of $R_1$, $R_2$, $R_3$ is OH or O-L-X, the remaining groups of $R_1$, $R_2$ and $R_3$ are each independently H.

Preferably, when one of $R_6$, $R_7$, and $R_8$ is OH or O-L-X, the remaining groups of $R_6$, $R_7$, and $R_8$ are each independently H.

In one embodiment of compounds of the formula (IA), only one of $R_1$, $R_2$ and $R_3$ is O-L-X and only one of $R_6$, $R_7$, and $R_8$ is OH, wherein X is a conjugation group or a water-solubilizing group.

In another embodiment of compounds of the formula (IA), only one of $R_1$, $R_2$ and $R_3$ is OH and only one of $R_6$, $R_7$, and $R_8$ is O-L-X, wherein X is a conjugation group or a water-solubilizing group.

In a preferred embodiment of compounds of the formula (IA), only one of $R_1$, $R_2$ and $R_3$ is O-L-X and only one of $R_6$, $R_7$, and $R_8$ is O-L-X, wherein:

(a) each X is a conjugation group; or (b) each X is a water-solubilizing group; or (c) one X is a conjugation group and the other X is a water-solubilizing group.

In a particularly preferred embodiment, $R_1$ is H, $R_2$ is O-L-X, $R_3$ is H, $R_6$ is H, $R_7$ is O-L-X and $R_8$ is H, wherein one X is a conjugation group and the other X is a water-solubilizing group.

In an especially preferred embodiment, each A is F, $R_1$ is H, $R_2$ is O-L-X, $R_3$ is H, $R_4$ is Ph, $R_5$ is Ph, $R_6$ is H, $R_7$ is O-L-X and $R_8$ is H, wherein one X is a conjugation group and the other X is a water-solubilizing group.

Suitable spacer groups L include moieties selected from substituted or unsubstituted, saturated or unsaturated, straight or branched chain alkyls, methylenes, amines, amides and ethers, or derivatives thereof. Alkyl moieties include substituted or unsubstituted, saturated or unsaturated, straight or branched chain alkyl moieties having up to 25 carbon atoms, more preferably up to 10 carbon atoms, even more preferably up to 5 carbon atoms. Methylene moieties include —$(CH_2)_n$—, wherein n is an integer from 1 to 16, preferably from 1 to 10, more preferably from 1 to 5, even more preferably from 1 to 3. Amine moieties include —$(CH_2)_2NH$—. Amide moieties include —$(CH_2)_2NHCO(CH_2)$—, —$(CH_2)_2NHCO(CH_2)_2$— and —$CONH(CH_2)_2NHCO(CH_2)_2$. Ether moieties include —$CH_2CH_2OCH_2CH_2$—. It will be appreciated that any suitable spacer group not listed here may be included in the compounds of the invention. It will also be appreciated that more than one spacer group may be included, and that the length and the number of the spacer group(s) may vary in accordance with the intended use of the compound.

Suitable conjugation groups include moieties selected from carboxylic acids, amines, alkynes, succinimidyl esters, azides, acyl azides, maleimides, diarylphosphonyl-aryl esters and biotin, or derivatives thereof.

A suitable diarylphosphonyl-aryl ester is ortho-diarylphosphonyl-aryl-methyl ester.

Moieties selected from carboxylic acids, amines, alkynes and succinimidyl esters are preferred, more preferably selected from alkynes and succinimidyl esters, most preferably succinimidyl esters. It will be appreciated that any suitable conjugation group not listed here may be included in the compounds of the invention. Advantageously, the conjugation group is chosen according to the intended use, as discussed in more detail below.

Suitable water-solubilizing groups include moieties selected from carboxylic acids, amines, sulfonic acids, alcohols, ethers, polyethers, amides, sulphonamides and tetrazoles, or derivatives thereof.

Moieties selected from sulfonic acids, carboxylic acids, ethers and polyethers are preferred, more preferably selected from sulfonic acids and carboxylic acids, most preferably sulfonic acids. It will be appreciated that any suitable water-solubilizing group not listed here may be included in the compounds of the invention.

In a preferred embodiment, one of $R_1$, $R_2$ and $R_3$ is O-L-X and one of $R_6$, $R_7$, and $R_8$ is O-L-X, wherein one X is a sulfonic acid moiety and the other X is a succinimidyl ester moiety. In this embodiment, preferably, each A is F, $R_4$ is Ph and $R_5$ is Ph.

In an especially preferred embodiment, one of $R_1$, $R_2$ and $R_3$ is O-L-X, wherein O-L-X is O—$(CH_2)_3$—$SO_3Na$ or O—$(CH_2)_3$—$SO_3H$ or O—$(CH_2)_3$—$SO_3^-$, and one of $R_6$, $R_7$, and $R_8$ is O-L-X, wherein O-L-X is O—$CH_2$-succinimidyl ester or O—$(CH_2)_2NHCO(CH_2)_2$-succinimidyl ester or O—$CONH(CH_2)_2NHCO(CH_2)_2$-succinimidyl ester; or one of $R_6$, $R_7$, and $R_8$ is O-L-X, wherein O-L-X is O—$(CH_2)_3$—$SO_3Na$ or O—$(CH_2)_3$—$SO_3H$ or O—$(CH_2)_3$—$SO_3$, and one $R_1$, $R_2$ and $R_3$ is O-L-X, wherein O-L-X is O—$CH_2$-succinimidyl ester or O—$(CH_2)_2NHCO(CH_2)_2$-succinimidyl ester or O—$CONH(CH_2)_2NHCO(CH_2)_2$-succinimidyl ester. In this embodiment, preferably, each A is F, $R_4$ is Ph and $R_5$ is Ph.

It will be appreciated by the skilled person that, depending on the intended use, some of the moieties used as conjugation groups may alternatively function as water-solubilizing groups. For example, carboxylic acid and amine moieties may be used as conjugation groups or as water-solubilizing groups. Thus, when a compound of the formulae (I) or (IA) includes two carboxylic acids as X, one carboxylic acid may, if desired, function as a conjugation group and the other as a water-solubilizing group; similarly for two amines as X; also similarly for a compound comprising one carboxylic acid moiety as X and one amine moiety as X.

It will be further appreciated by the skilled person that depending on the intended use, ether moieties typically used as water-solubilizing groups may also function as spacer groups. For example, where more than one ether group is present, forming a polyether, one or more of the ether groups present may be providing the function of a spacer group.

Preferably, the compounds according to the invention have a maximum absorbance $\lambda_{max}$ at greater than 660 nm, preferably greater than 670 nm, and a maximum emission at greater than 690 nm, preferably greater than 720 nm, as measured in aqueous solutions.

Table 1 contains representative compounds according to the formulae (I) and (IA), wherein each A is F, $R_1$ is H, $R_3$ is H, $R_4$ is Ph, $R_5$ is Ph and $R_8$ is H. The compounds provided in Table 1 are representative compounds only and are not intended to be an exhaustive list.

TABLE 1

| Reference number of compound in Examples where applicable | $R^2$ | $R^6$ | $R^7$ |
| --- | --- | --- | --- |
| 2 (Example 2(A)) | OH | H | $OCH_2$—C≡CH |
| 9 (Example 3(A)) | $O((CH_2)_2O)_3CH_3$ | H | $O(CH_2)_2NHBoc$ |
| Variation of 9 (Example 3(A)) | $O((CH_2)_2O)_3CH_3$ | H | $O(CH_2)_2NH_2$ |
| 10 (Example 3(A)) | $O((CH_2)_2O)_3CH_3$ | H | $O(CH_2)_2NHCO(CH_2)_2CO_2H$ |

TABLE 1-continued

| Reference number of compound in Examples where applicable | R² | R⁶ | R⁷ |
|---|---|---|---|
| 11a (Example 3(A)) | O((CH₂)₂O)₃CH₃ | H | O(CH₂)₂NHCO(CH₂)₂-C(=O)-O-N(succinimide) |
| 11b (Example 3(A)) | O((CH₂)₂O)₃CH₃ | H | O(CH₂)₂NHCO(CH₂)₂-C(=O)-O-N(sulfo-succinimide, SO₃⁻) |
| 16 (Example 4) | OCH₂CO₂⁻ | H | OCH₂CO₂⁻ |
| Variation of 16 (Example 4) | OCH₂CO₂H | H | OCH₂CO₂H |
| 17 (Example 4) | O(CH₂)₃SO₃⁻ | H | O(CH₂)₃SO₃⁻ |
| Variation of 17 (Example 4) | O(CH₂)₃SO₃H | H | O(CH₂)₃SO₃H |
| 26 (Example 6) | OCH₂CH₂CH₂SO₃Na | H | OCH₂—C≡CH |
| — | OCH₂CO₂H | H | OCH₂—C≡CH |
| — | O(CH₂)₃SO₃Na | H | O(CH₂)₂NH₂ |
| — | O(CH₂)₃SO₃Na | H | OCH₂CO₂H |
| — | O(CH₂)₃SO₃Na | H | OCH₂-C(=O)-O-N(succinimide) |
| 27 (Example 6) | O(CH₂)₃SO₃Na | H | OH |
| — | OCH₂CO₂H | H | OH |
| — | OCH₂CO₂H | NO₂ | OH |
| — | OCH₂-C(=O)-O-N(succinimide) | H | OH |
| — | O(CH₂)₃SO₃Na | H | OCONH(CH₂)₂NHCO(CH₂)₂-C(=O)-O-N(succinimide) |

TABLE 1-continued

| Reference number of compound in Examples where applicable | R² | R⁶ | R⁷ |
|---|---|---|---|
| 28 (Example 6) | O(CH₂)₃SO₃Na | H | O(CH₂)₂NHCO(CH₂)₂–C(=O)–O–N(succinimidyl) |
| — | O(CH₂)₃SO₃Na | H | O(CH₂)₂NHCO(CH₂)₂–N(maleimidyl) |
| — | OCH₂–C(=O)–O–N(succinimidyl) | H | OCH₂–C(=O)–O–N(succinimidyl) |
| 29 (Example 6) | O((CH₂)₂O)₃CH₃ | H | O(CH₂)₂NHCO(CH₂)₂–N(maleimidyl) |
| 30 (Example 6) | O((CH₂)₂O)₃CH₃ | H | O(CH₂)₂NH–C(=O)–C₆H₃(P(Ph)₂)–C(=O)OCH₃ |
| 31 (Example 6) | O((CH₂)₂O)₃CH₃ | H | O(CH₂)₂NH–C(=O)–(CH₂)₄–biotinyl |

Included in compounds of the formula (I) are compounds of the formula (IB).

In compounds of the formula (IB),

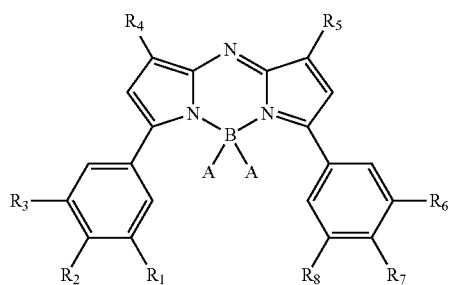

(IB)

each A and R₄ and R₅ are as defined above for compounds of the formula (I); and $R_1$, $R_2$, $R_3$, $R_6$, $R_7$, and $R_8$ are each independently H, OH or NO₂; with the proviso that at least one of $R_1$, $R_2$, $R_3$ is OH and at least one of $R_6$, $R_7$, and $R_8$ is OH.

Preferably, only one of $R_1$, $R_2$, $R_3$ is OH, and the remaining groups of $R_1$, $R_2$, and $R_3$ are each independently H or NO₂; and/or only one of $R_6$, $R_7$, and $R_8$ is OH, and the remaining groups of $R_6$, $R_7$, and $R_8$ are each independently H or NO₂.

Preferably, when one of $R_1$, $R_2$, $R_3$ is OH, the remaining groups of $R_1$, $R_2$, and $R_3$ are each independently H.

Preferably, when one of $R_6$, $R_7$, and $R_8$ is OH, the remaining groups of $R_6$, $R_7$, and $R_8$ are each independently H.

In a preferred embodiment of compound (IB), $R_1$ is H, $R_2$ is OH, $R_3$ is H, $R_6$ is H, $R_7$ is OH and $R_8$ is H. In an especially preferred embodiment of compound (IB), each A is F, $R_1$ is H, $R_2$ is OH, $R_3$ is H, $R_4$ is Ph, $R_5$ is Ph, $R_6$ is H, $R_7$ is OH and $R_8$ is H.

Compounds of the formula (IB) are useful in the preparation of compounds of the formula (I), including compounds of the formula (IA).

The compounds of the invention may be prepared in accordance with Scheme A:

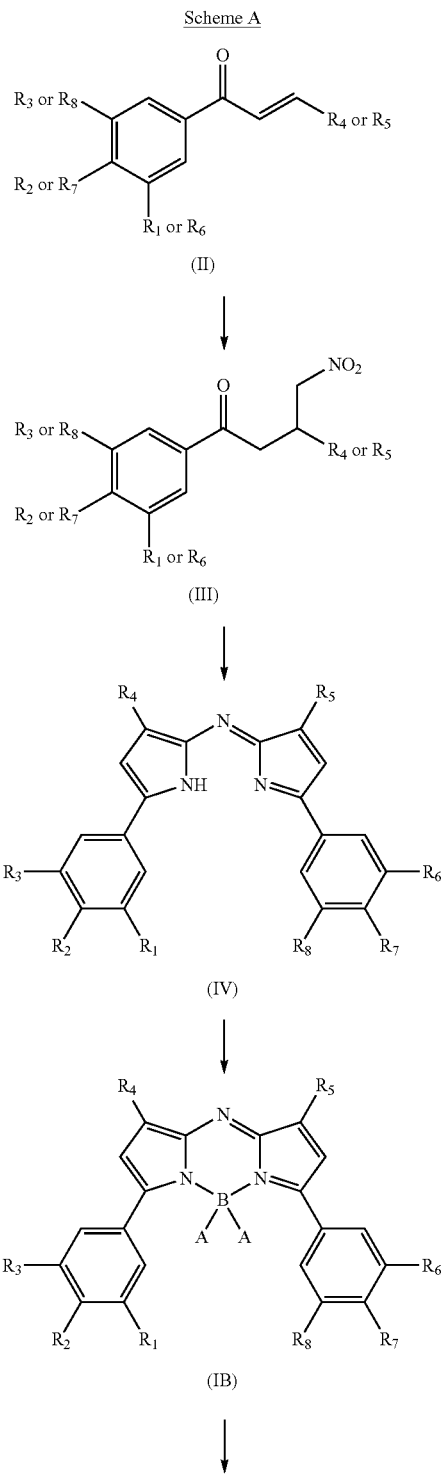

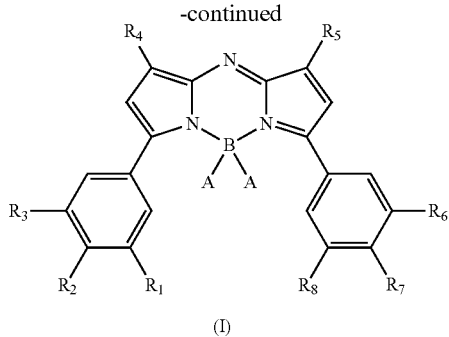

Compounds of the Formula (IV) to Compounds of the Formula (IB):

The invention further provides a method of preparing a compound of the formula (IB), wherein the method comprises reacting a compound of formula (IV), wherein $R_1$-$R_8$ are as defined above for compounds of the formula (IB), with boron trihalide or a derivative thereof.

Compounds of the formula (IB) wherein each A is O—Y, may be formed by reacting a product formed by the above reaction with a suitable alkoxide.

Suitable boron trihalides include boron trifluoride, boron trichloride, boron tribromide and boron triiodide, preferably boron trifluoride. A derivative of boron trifluoride is preferred, especially boron trifluoride diethyletherate ($BF_3OEt_2$).

The reaction may be carried out in the presence of a suitable base. Suitable bases include diisopropylethylamine (DIEA, Hünig's base), triethylamine and caesium carbonate, preferably diisopropylethylamine.

Preferably, the reaction is carried out in the presence of a suitable solvent. Suitable solvents include THF, dichloromethane ($CH_2Cl_2$), toluene and benzene, preferably dichloromethane ($CH_2Cl_2$).

Preferably, in the compound of the formula (IV), $R_1$ is H, $R_2$ is OH, $R_3$ is H, $R_4$ is Ph, $R_5$ is Ph, $R_6$ is H, $R_7$ is OH and $R_8$ is H, wherein the compound of the formula (IV) is [5-(4-Hydroxyphenyl)-3-phenyl-1H-pyrrol-2-yl]-[5-(4-hydroxyphenyl)-3-phenylpyrrol-2-ylidene]amine.

Conveniently, compounds of the formula (IV) also form part of the invention.

Compounds of the Formula (III) to Compounds of the Formula (IV):

The compound of the formula (IV) may be prepared by reacting a compound of the formula (III), wherein $R_1$-$R_8$ are as defined above for compounds of the formula (IB), with an ammonium source in a suitable solvent.

Suitable ammonium sources include ammonium chloride, ammonium acetate and ammonium formate, preferably ammonium acetate.

Suitable solvents include THF, dichloromethane ($CH_2Cl_2$), ethanol and isopropyl alcohol, preferably ethanol.

Preferably, in the compound of the formula (III), $R_1$/$R_6$ is H, $R_2$/$R_7$ is OH, $R_3$/$R_8$ is H, and $R_4$/$R_5$ is Ph, wherein the compound of the formula (III) is 1-(4-hydroxyphenyl)-4-nitro-3-phenylbutan-1-one.

Conveniently, compounds of the formula (III) also form part of the invention.

Compounds of the Formula (II) to Compounds of the Formula (III):

The compound of the formula (III) may be prepared by reacting a compound of the formula (II), wherein $R_1$-$R_8$ are as defined above for compounds of the formula (IB), with a methylene nitro source in a suitable solvent.

A suitable methylene nitro source is nitromethane.

Suitable solvents include THF, dichloromethane ($CH_2Cl_2$), methanol, ethanol, preferably ethanol.

Preferably, in the compound of the formula (II), $R_1/R_6$ is H, $R_2/R_7$ is OH, $R_3/R_8$ is H, and $R_4/R_5$ is Ph, wherein the compound of the formula (II) is a known chalcone, available from TCI laboratory Chemicals.

Compounds of the Formula (IB) to Compounds of the Formula (I):

The invention further provides a method of preparing a compound of the formula (I), wherein the method comprises converting at least one OH group of a compound of the formula (IB) to O-L-X, in the presence of a suitable solvent.

Suitable solvents include THF, dichloromethane ($CH_2Cl_2$), acetonitrile, toluene, DMF and acetone, preferably THF.

The reaction may be carried out in the presence of a suitable base. Suitable bases include NaH, diisopropylethylamine (DIEA, Hünig's base), triethylamine and caesium carbonate, preferably NaH.

Preferably, the conversion of the at least one OH group to O-L-X is achieved by alkylation of the at least one OH group.

Preferably, the conversion of the at least one OH group to O-L-X involves the conversion of at least two OH groups to O-L-X. Further preferably, at least one O-L-X group is provided on one of $R_1$, $R_2$ and $R_3$ of the compound of the formula (I), and at least one O-L-X group is provided on one of $R_6$, $R_7$, and $R_8$ of the compound of the formula (I). More preferably, only one O-L-X group is provided on one of $R_1$, $R_2$ and $R_3$ of the compound of the formula (I), and only one O-L-X group is provided on one of $R_6$, $R_7$, and $R_8$ of the compound of the formula (I), wherein, further preferably, one X is a conjugation group and the other X is a water-solubilizing group.

Preferably, the compound of formula (I) is a compound of formula (IA).

The invention still further provides a dye conjugate, comprising (i) a compound of the formula (I) bearing at least one conjugation group X, and (ii) a complementary binding group; wherein the conjugation group X is capable of covalently binding the compound of the formula (I) to the complementary binding group.

Preferably, the compound of the formula (I) is a compound of the formula (IA).

Suitable binding groups include carboxylic acids, aldehydes, ketones, esters, amines, thiols, azides and avidins.

Suitable conjugation groups and complementary binding groups include the following:—

(a) an amine as conjugation group and a carboxylic acid, aldehyde, ketone or ester as complementary binding group;

(b) a carboxylic acid as conjugation group and an amine as complementary binding group;

(c) a succinimidyl ester as conjugation group and an amine as complementary binding group;

(d) a maleimide as conjugation group and a thiol as complementary binding group;

(e) an alkyne as conjugation group and an azide as complementary binding group;

(f) an ortho-diarylphosphonyl-aryl-methyl ester as conjugation group and an azide as complementary binding group; and (g) biotin as conjugation group and avidin as complementary binding group.

Some of these conjugation groups and complementary binding groups are indicated in Table 2 below, wherein the complementary binding group is referred to as a reacting moiety:

TABLE 2

| Conjugatable Group | Reacting Moiety |
|---|---|
| $H_2N$—Spacer-Fluorophore | R—$CO_2H$ or R-C(O)-CH$_2$-N(succinimide) |
| HO-C(=O)-Spacer-Fluorophore | R—$NH_2$ |
| (succinimidyl)-O-C(=O)-Spacer-Fluorophore | R—$NH_2$ |
| (sulfo-succinimidyl, $^\ominus O_3S$)-O-C(=O)-Spacer-Fluorophore | R—$NH_2$ |

TABLE 2-continued

| Conjugatable Group | Reacting Moiety |
|---|---|
| Maleimide-CH2-Spacer-Fluorophore | R—SH |
| 2-(diphenylphosphino)-4-(Spacer-Fluorophore-carbonyl)-methyl benzoate | R—N$_3$ |
| HC≡C-CH$_2$-Spacer-Fluorophore | R—N$_3$ |

The binding group may form part of a larger molecule including, but not limited to, nucleic acids, nucleotides, carbohydrates, drugs, polymers, peptides, proteins, antibodies, lipids including nanoparticle forms thereof; and other biologically derived or synthetic chemical materials including nanoparticle forms thereof.

Such a molecule may, if desired, be in the form of or attached to synthetic particles. Such particles may be in the form of nano-beads, preferably having a diameter from about 0.5 nm to about 500 nm, more preferably from about 5 nm to about 500 nm, more preferably from about 50 nm to about 200 nm, most preferably about 100 nm.

Suitable nano-beads include polystyrene, gold or silver. It will be appreciated that other metallic and/or inorganic nano-beads may be used.

The invention still further provides the use of a compound of the formula (I) in the fluorescent labelling of a molecule to produce a dye conjugate. Preferably, the compound of the formula (I) is a compound of the formula (IA).

The invention even further provides the use of a compound of the formula (I) as a water-soluble fluorescent dye. Preferably, the compound of the formula (I) is a compound of the formula (IA).

Advantages of the invention:

The compounds have strong absorption and emissions within the NIR spectral region.

The compounds have high photostability.

The compounds are versatile and have many commercial uses:

For example, in some embodiments, when OH is present, the compounds may be pH responsive, wherein the fluorescence can be switched on and off as desired.

In other embodiments, the water-solubilizing groups advantageously enhance the solubility of the compounds of the invention in aqueous solution.

In still other embodiments, the conjugation groups enable the compound to be covalently bound to a complementary binding group, forming a dye conjugate. When two X groups are present, and one X is a conjugation group and the other X is a water-solubilizing group, preferably facilitated by a desymmetrization step during manufacture, the compound may be bound to one complementary binding group, with the water-solubilizing group conveniently enhancing the solubility of the compounds in aqueous solution. When two X groups are present, and both X are COOH, the compound may conveniently be bound to two separate complementary binding groups on small molecules, for example, two amine groups on two small peptides.

The compounds may be bound to particles such as nanobeads.

Polymeric nanoparticle conjugate dyes of the invention have been found to exhibit a dramatic increase in fluorescent intensity upon entry into a cell, typically at least a 2-fold, 3-fold, 4-fold, 5-fold, 6-fold, 7-fold, 8-fold, 9-fold, or 10-fold increase in fluorescent intensity when compared with the fluorescent intensity when the conjugate dye is outside the cell.

The invention will now be further described, with reference to the following non-limiting examples:—

BRIEF DESCRIPTION OF THE DRAWINGS

The invention will be more clearly understood from the following description of an embodiment thereof, given by way of example only, with reference to the accompanying drawings, in which:—

FIG. 11. Fluorescence pH Sigmoidal Plot for 8a.

DETAILED DESCRIPTION OF THE INVENTION

EXAMPLE 1

Compound 6

Figure 1:
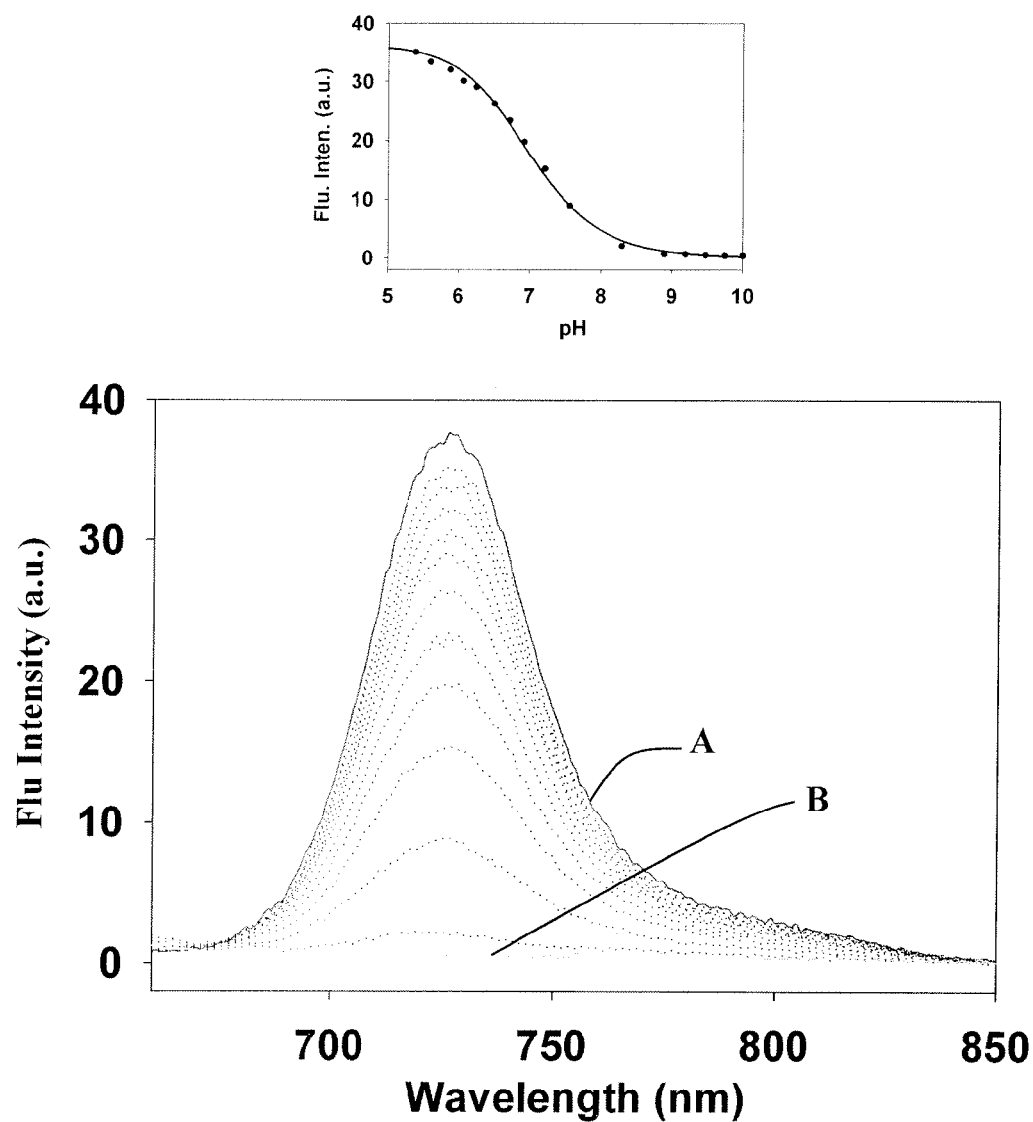
FIG. 1. pH responsive fluorescence spectra of 2. A trace pH=6.0, B trace pH=9.0. Excitation at 640 nm, slit widths 10 nm, 5×10$^{-7}$ M in water/CrEL. I$_{NaCl}$=150 mmol/L. Insert; sigmoidal plot predicting a pKa value of 6.9.

Compound 6, which is a compound of the formula (IB), was prepared as follows. With reference to Scheme 1, the synthetic route commenced with an addition of nitromethane to chalcone 3, which is compound of the formula (II), which gave 1-(4-hydroxyphenyl)-4-nitro-3-phenylbutan-1-one 4, which is a compound of the formula (III), in 73% yield.

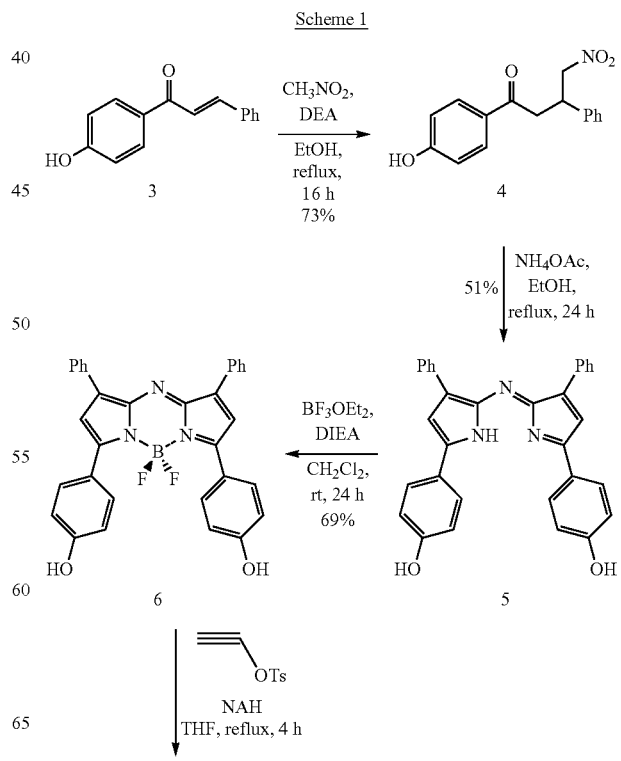

Scheme 1

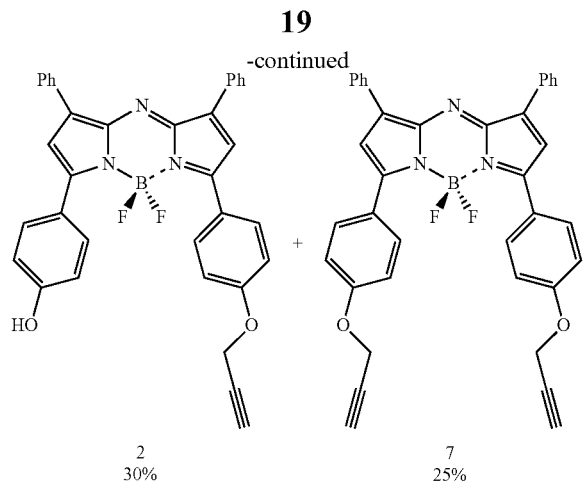

2
30%

7
25%

Subsequent generation of the bis-phenol substituted azadipyrromethene 5, which is a compound of the formula (IV), was achieved by the reflux of 4 with ammonium acetate in ethanol for 24 h. Filtration of the precipitate from the crude reaction mixture gave the pure product in 51% yield. Compound 5 was converted to its $BF_2$ chelated analogue 6 with $BF_3$ diethyletherate and diisopropylethylamine (DIEA) in dichloromethane for 24 h. An isolated yield of 69% of 6 was obtained following chromatography on silica gel. Compound 6 can advantageously be used to prepare a wide variety of compounds (I) according to the invention, as described in Examples 2(A), 3(A), 4 and 6, and also a wide variety of dye conjugates according to the invention, as described in Examples 2(B), 3(B) and 5.

Further details of the products 4, 5 and 6 and synthesis thereof are provided below.

1-(4-Hydroxyphenyl)-4-nitro-3-phenylbutan-1-one (4)

A solution of 1-(4-hydroxyphenyl)-3-phenylpropenone 3 (9 mmol) in EtOH (15 mL) was treated with diethylamine (4.6 mL, 45 mmol) and nitromethane (4.8 mL, 90 mmol) and heated under reflux for 16 h. The solution was cooled and acidified with 4 M HCl, partitioned between EtOAc (50 mL) and $H_2O$ (50 mL). The organic layer was separated, dried over sodium sulfate and evaporated under reduced pressure. The residue was stirred in cold $Et_2O$ (30 mL) for 10 min and filtered to give the product 4 as a colorless solid (1.84 g, 73%), m.p. 112-113° C. (MeOH). $^1H$ NMR (300 MHz, $CDCl_3$): δ 7.86 (d, J=8.5 Hz, 2H), 7.35-7.26 (m, 5H), 6.85 (d, J=8.5, 2H), 5.44 (s, 1H), 4.86-4.80 (m, 1H), 4.64-4.71 (m, 1H), 4.25-4.16 (m, 1H), 3.46-3.31 (m, 2H). $^{13}C$ NMR (125 MHz, $CDCl_3$): δ 195.3, 160.3, 139.2, 130.6, 129.6, 129.0, 127.8, 127.4, 115.4, 79.6, 41.1, 39.4. IR (KBr disc): 3427, 1646 $cm^{-1}$. ES-MS: m/z 284.1 $[M–H]^–$ HRMS $[M+Na]^+$: 308.0887, $C_{16}H_{15}NNaO_4^+$ requires 308.0899.

[5-(4-Hydroxyphenyl)-3-phenyl-1H-pyrrol-2-yl]-[5-(4-hydroxyphenyl)-3-phenylpyrrol-2-ylidene]amine (5)

Compound 4 (2.0 g, 7.0 mmol) and ammonium acetate (18.9 g, 245 mmol) in EtOH (50 mL) were heated under reflux for 24 h. The reaction was cooled to rt, the precipitate filtered and the isolated solid washed with cold ethanol (20 mL) to yield the product 5 as a blue-black solid (0.86 g, 51%), mp 245-246° C. (MeOH). $^1H$ NMR (300 MHz, MeOD): δ 7.99 (d, J=6.6 Hz, 4H), 7.79 (d, J=8.7 Hz, 4H), 7.36-7.29 (m, 6H), 7.20 (s, 2H), 6.92 (d, J=8.7 Hz, 4H), (NH, OH not observed). $^{13}C$ NMR (125 MHz, MeOD): δ 159.9, 154.5, 148.8, 141.5, 133.9, 128.6, 128.0, 127.7, 127.3, 123.4, 115.8, 113.8. IR (KBr disc): 3054, 1603, 1265 $cm^{-1}$. ES-MS: m/z 482.3 $[M+H]^+$. HRMS $[M+H]^+$: 482.1851, $C_{32}H_{24}N_3O_2$ requires 482.1869.

$BF_2$ Chelate of [5-(4-hydroxyphenyl)-3-phenyl-1H-pyrrol-2-yl]-[5-(4-hydroxyphenyl)-3-phenylpyrrol-2-ylidene]amine (6).

Compound 5 (0.15 g, 0.31 mmol) was dissolved in dry $CH_2Cl_2$ (15 mL), treated with diisopropylethylamine (0.54 mL, 3.11 mmol) and $BF_3$ diethyletherate (0.55 mL, 4.35 mmol), and stirred under $N_2$ for 24 h. The reaction mixture was diluted with EtOAc (30 mL), washed with water (30 mL) and the organic layer evaporated to dryness. Purification by column chromatography on silica eluting with $CH_2Cl_2$/EtOAc (4:1) gave the product 6 as a red metallic solid (113 mg, 69%), mp 253-254° C. (MeOH). $^1H$ NMR (300 MHz, MeOD): δ 8.08-8.05 (m, 8H), 7.40-7.30 (m, 6H), 7.20 (s, 2H), 6.91-6.88 (m, 4H), (OH not observed). $^{13}C$ NMR (125 MHz, MeOD): δ 160.5, 157.9, 144.8, 142.3, 132.3, 131.7, 128.9, 128.7, 128.0, 122.7, 118.3, 115.2. IR (KBr disc): 3351, 1605 $cm^{-1}$. ES-MS: m/z 530.3 $[M+H]^+$. HRMS $[M+H]^+$: 530.1876, $C_{32}H_{23}BF_2N_3O_2$ requires 530.1851.

EXAMPLE 2(A)

Compound 2: pH Responsive Compound Comprising a Conjugation Group

With reference to Scheme 1, the synthesis of compound 2, which is a compound of formula (I), specifically, a compound of the formula (IA), required a desymmetrization step involving alkylation of one of the two phenol groups of 6. This alkylation was carried out using 2.2 equiv. of propargyltosylate and NaH in THF for 4 h under reflux. It was found that these specific conditions biased the distribution of mono-2 and bis-alkylated 7 products toward the mono substituted derivative (Scheme 1). Exploiting the large polarity difference between 2 and 7 allowed for facile separation on silica gel chromatography and gave products in isolated yields of 30 and 25% respectively.

Further details of the products 2 and 7 and synthesis thereof are provided below.

$BF_2$ Chelate of 4-{4-phenyl-5-[3-phenyl-5-(4-prop-2-ynyloxyphenyl)-pyrrol-2-ylideneamino]-1H-pyrrol-2-yl}phenol (2)

Compound 6 (75 mg, 0.14 mmol) and NaH (60% oil dispersion) (12 mg, 0.52 mmol) were stirred in dry THF (8 mL) and treated with propargyltoluolsulfonate (12 mg, 0.31 mmol) at 0° C. under $N_2$. The reaction was warmed to rt and then heated under reflux for 3 h. The reaction mixture was cooled and partitioned between EtOAc (10 mL) and brine (20 mL). The organic layer was separated, dried over sodium sulfate and the solvent removed under reduced pressure. Purification by column chromatography on silica eluting with $C_6H_{12}$/EtOAc (4:1) first eluted compound 7 (21 mg, 25%) 166-169° C. followed by the desired product eluted with $C_6H_{12}$/EtOAc (3:2) 2 as a red metallic solid (25 mg, 30%, m.p. 82-84° C.).

Analysis for 2

$^1$H NMR (300 MHz, CDCl$_3$): δ 8.09-7.99 (m, 8H), 7.47-7.38 (m, 6H), 7.07 (d, J=8.7 Hz, 2H), 7.02 (s, 2H), 6.88 (d, J=8.6 Hz, 2H), 5.6 (bs, 1H), 4.75 (s, 2H), 2.55 (s, 1H). $^{13}$C NMR (125 MHz, CDCl$_3$): δ 159.8, 158.7, 158.4, 157.7, 145.5, 145.2, 143.5, 143.1, 132.4, 132.3, 131.8, 131.5, 131.4, 131.3, 129.3, 129.3, 129.2, 128.5, 125.0, 124.1, 118.8, 118.5, 115.8, 115.0, 78.0, 76.0, 55.9. IR (KBr disc): 3502, 1603 cm$^{-1}$. ES-MS: m/z 568.4, [M+H]$^+$. HRMS [M+H]$^+$: 568.2034, C$_{35}$H$_{25}$BF$_2$N$_3$O$_2$ requires 568.2008.

Analysis for 7

$^1$H NMR (300 MHz, CDCl$_3$): δ 8.12-8.07 (m, 8H), 7.49-7.42 (m, 6H), 7.06 (d, J=9.1 Hz, 2H), 7.02 (s, 2H), 4.79 (s, 4H), 2.58 (s, 2H). $^{13}$C NMR (125 MHz, CDCl$_3$): δ 159.8, 158.1, 145.4, 143.4, 132.4, 131.6, 131.5, 129.2, 128.5, 124.9, 118.7, 115.0, 78.0, 76.0, 55.8. IR (KBr disc): 1601, 1504 cm$^{-1}$. ES-MS: m/z 606.2, [M+H]$^+$. HRMS [M+H]$^+$: 606.2135, C$_{38}$H$_{27}$BF$_2$N$_3$O$_2$ requires 606.2164.

Spectral properties of 2 in organic solvents were very similar to the prior art compound 1 with the absorption and emission maxima of 2 in CHCl$_3$ at 680 and 708 nm respectively with a high fluorescence quantum yield (Φ$_f$) of 0.37 (Table 3).

TABLE 3

Absorption/Emission Properties of 2

| entry | solvent | λ$_{max}$ abs (nm)$^a$ | λ$_{max}$ flu (nm)$^b$ |
|---|---|---|---|
| 1 | CHCl$_3$ | 680 | 708$^c$ |
| 2 | C$_7$H$_8$ | 685 | 711 |
| 3 | CH$_3$OH | 688 | 716 |
| 4 | H$_2$O/CrEL | 700 | 729 |

$^a$(5 × 10$^{-6}$ M).
$^b$(5 × 10$^{-7}$ M).
$^c$Φ$_f$ = 0.37 (1 as standard).

Spectral characteristics showed a slight dependence upon solvent dipolarity with a bathochromatic shifts of 8 nm for absorbance and emission maxima in methanol. Additionally an aqueous solution generated by formulation using Cremophor EL (CrEL) showed further small bathochromic shifts (700/729 nm) when compared to organic solvents.

Figure 2:
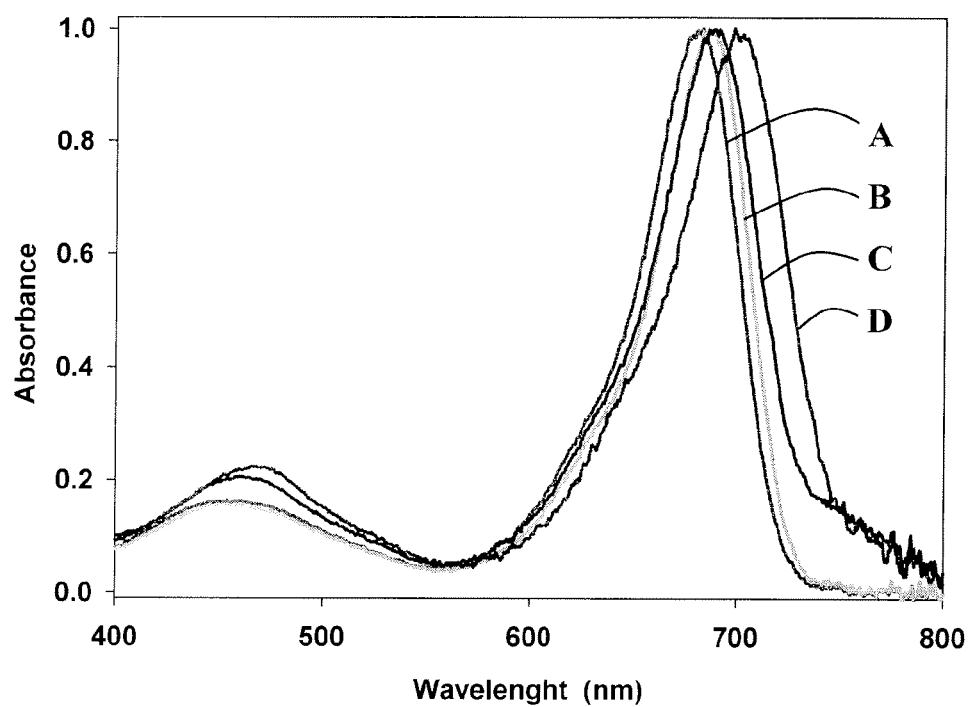
FIG. 2. UV-Visible Spectral of 2 in Various Solvents. Solvents CHCl$_3$ (A); toluene (B), ethanol (C), H$_2$O/CrEl (D).
Figure 3:
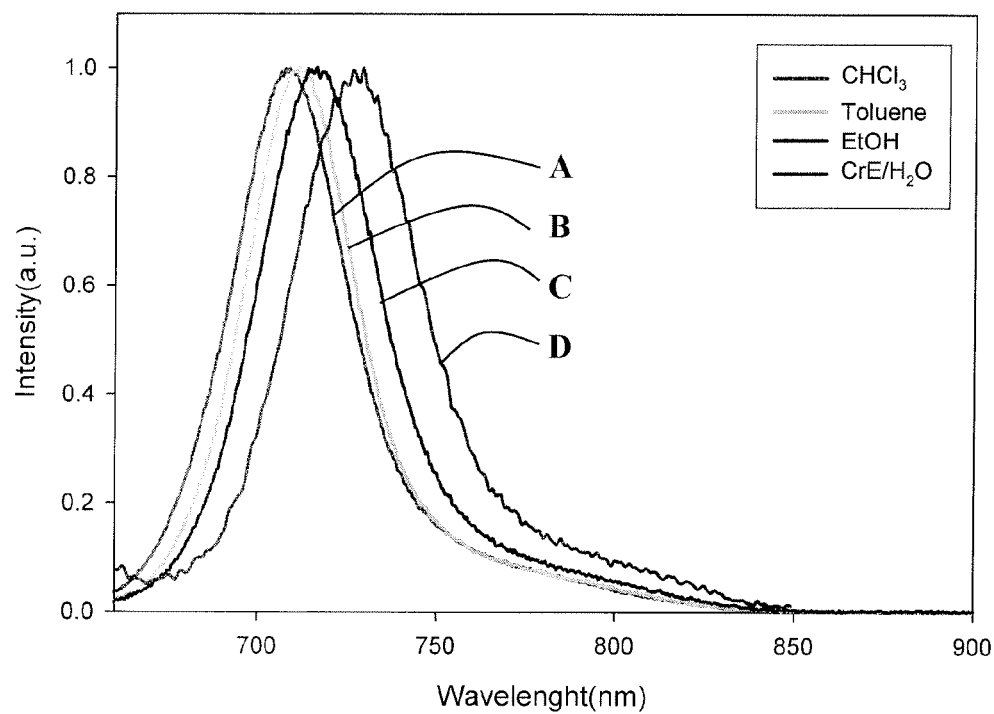
FIG. 3. Fluorescence Spectral of 2 in Various Solvents. Solvents CHCl$_3$ (A); toluene (B), ethanol (C), H$_2$O/CrEl (D).
Figure 4:
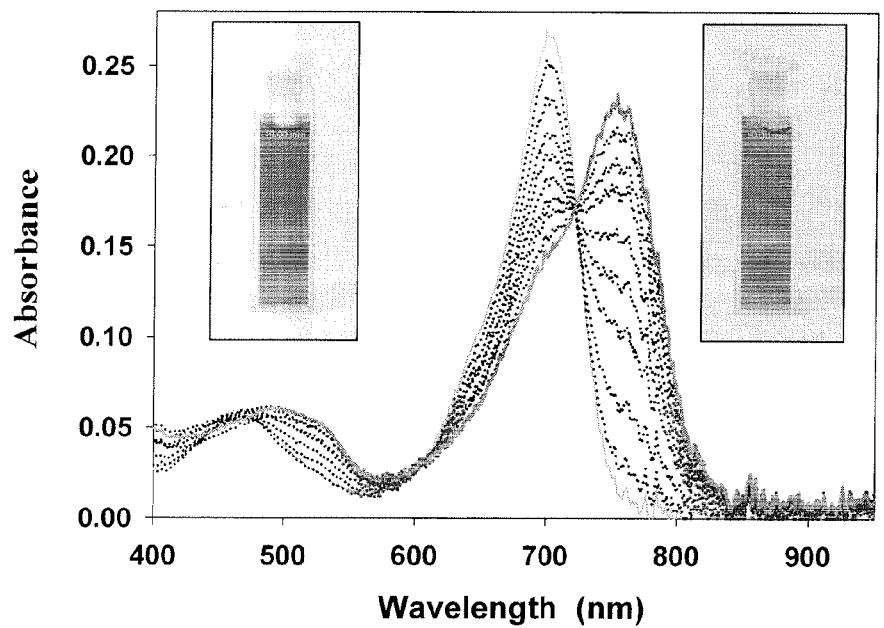
FIG. 4. UV-Visible pH profile of conversion of 2 to 2-H$^+$ at 5×10$^{-6}$ M in water/CrEL, I$_{NaCl}$=150 mmol/L. Inset: Colormetric response of 2; LHS pH=6.8, RHS pH=8.8.

In contrast to 1, the spectral properties of 2 displayed a striking response across the physiological pH range (FIG. 1). The excited state response of 2 at the λ max of 729 nm in aqueous solutions showed a greater than 15 fold fluorescence intensity differential between pH 6 and 8 with virtually complete suppression of fluorescence signal at pH 9 (FIG. 1). A sigmoidal plot of pH versus fluorescence intensity predicted an apparent pKa of 6.9 (FIG. 1, inset). Further spectral properties are illustrated in FIGS. 2, 3 and 4. As would be expected for an ICT process, the UV-visible spectrum of 2 was strongly influenced by pH (FIG. 4). The absorption band at 700 nm was progressively reduced in intensity with increasing pH and a new band appeared at 775 nm with an isosbestic point at 740 nm indicative of the formation of a mono-deprotonated species.

Compound 2 provides the advantage of being both pH responsive via the OH group, and conjugatable via the alkyne group, as illustrated below.

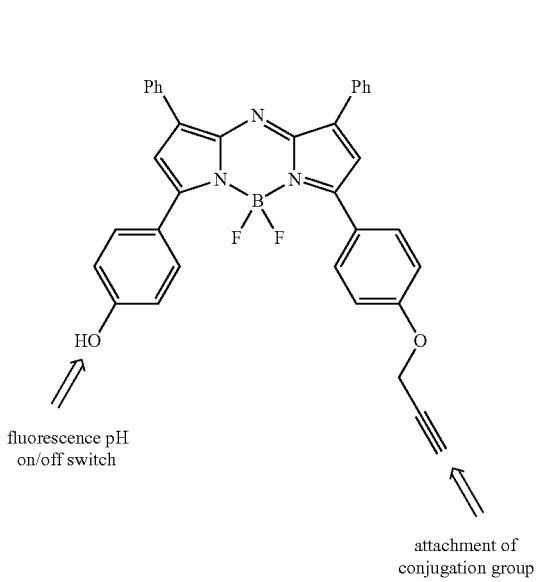

2 fluorescence pH on/off switch attachment of conjugation group

EXAMPLE 2(B)

Compounds 8a, 8b, 8c: pH Responsive Dye Conjugates

In the prior art, in conjunction with optimal photophysical characteristics, two complementary approaches have often been adopted to enhance differentiation of the imaging target from background fluorophore. The first, and more common, is the use of conjugated fluorophores generated by the covalent attachment of a targeting (bio)-molecule to the fluorescent probe which facilitates a target selective accumulation of fluorophore. An alternative approach is the modulation of the fluorescence signal intensity (from low to high) in response to a specific molecular recognition at the endogenous target. In spite of the success of both strategies a combination of both processes are rarely investigated. Here, a strategy is outlined to achieve a prototype azide-conjugatable and pH responsive NIR fluorescent platform. It was proposed that the on/off fluorescence switching operation would be governed by a straight-forward phenol/phenolate interconversion on the fluorophore, with conjugation to a molecular targeting motif via an alkyne-azide cycloaddition. To date, there are few literature reports of NIR pH responsive fluorophores in spite of their potential imaging applications for disease states that can induce localized intra- and extracellular pH changes such as cancers, renal failure and ischemia.

It was investigated as to whether 2 would be capable of conjugation via azide cycloaddition and pH modulation of the intensity of fluorescence output would be controlled by a phenol/phenolate interconversion. The mild aqueous conditions required for azide-alkyne cycloadditions offer distinct advantages when utilized for bioconjugation reactions.

With reference to Scheme 2, in order to demonstrate functional group tolerance of azide reactions with 2, three azides containing amino, carboxy and carbohydrate substitutents were tested. The optimized reaction conditions with 1-azido-1-deoxy-β-D-galactopyranoside, 4-azidobutyric acid and (2-azidoethyl)carbamic acid t-butyl ester were identified as CuSO$_4$/Cu/sodium ascorbate in THF/H$_2$O (3:1) under reflux for 3 h (Scheme 2). The copper salts were removed by aqueous extraction and cycloadducts 8a-c were isolated in good yields of 68 to 88% following either recrystallization from methanol or column chromatography.

Scheme 2. Azide Cycloaddition reactions
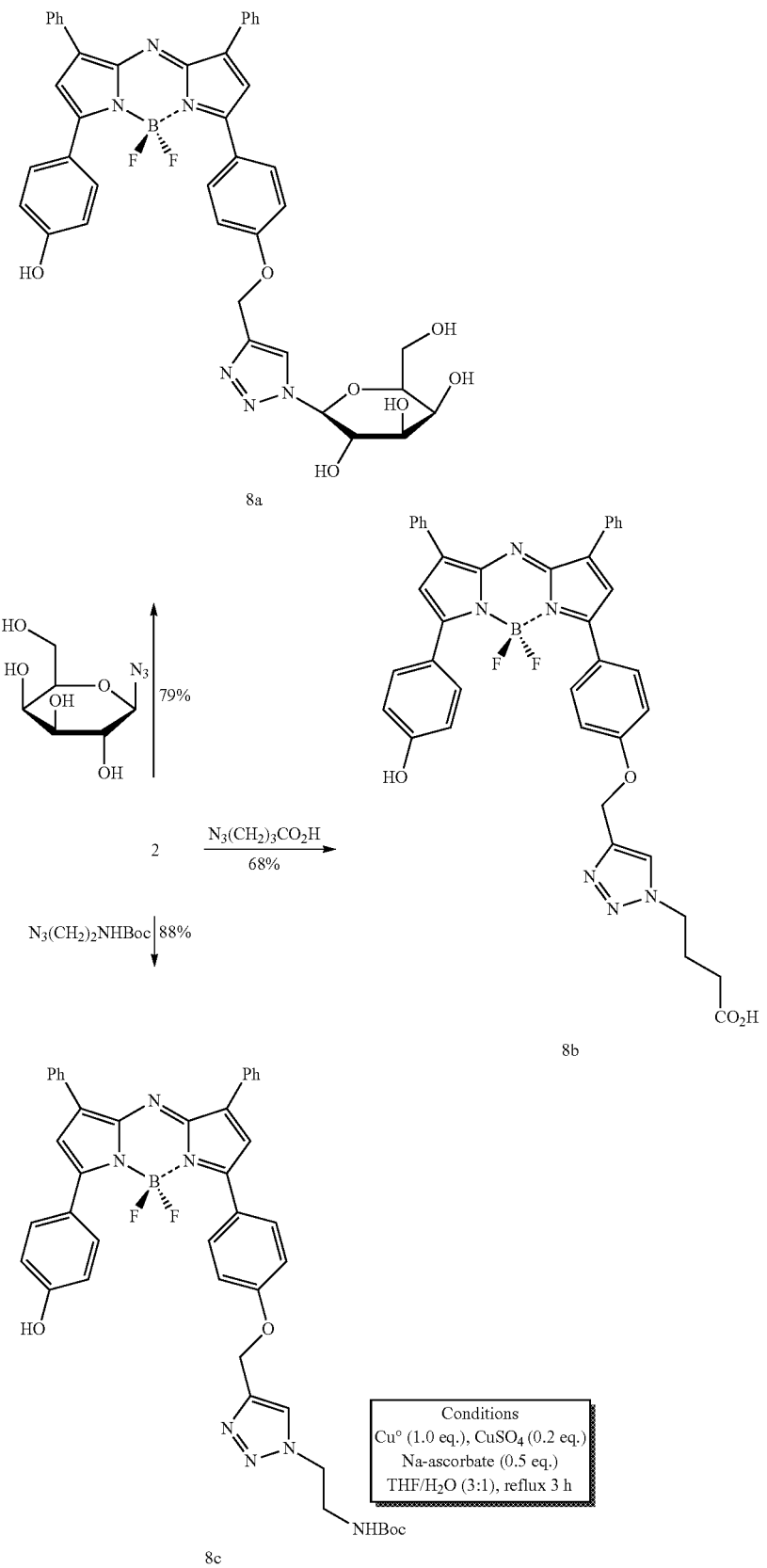

Further details of the products 8a, 8b and 8c, and synthesis thereof are provided below.

2-Hydroxymethyl-6-[4-(4-[5-[5-(4-hydroxyphenyl)-3-phenyl-1H-pyrrol-2-ylimino]-4-phenyl-5H-pyrrol-2-yl]-phenoxymethyl)-[1,2,3]triazol-1-yl]-tetrahydropyran-3,4,5-triol (8a)

A solution of 2 (0.14 g, 0.24 mmol) and 1-azido-1-deoxy-β-D-galactopyranoside (0.12 g, 0.64 mmol) in THF:H$_2$O (20 mL, 3:1) was treated with a THF:H$_2$O (15 mL, 3:1) solution of Cu(0) (15 mg, 0.24 mmol), CuSO$_4$.5H$_2$O (8 mg, 0.049 mmol) and Na-ascorbate (24 mg, 0.12 mmol). The reaction mixture was heated for 3 h under N$_2$, cooled and partitioned between EtOAc (30 mL) and water (30 mL). The aqueous layer was re-extracted with EtOAc (2×30 mL) and the combined organic layers were dried and evaporated to dryness under reduced pressure. Recrystallization from MeOH gave the product 8a as a dark green solid (142 mg, 79%, m.p. 180-182° C.). $^1$H NMR (300 MHz, MeOD): δ 8.36 (s, 1H), 8.14-8.10 (m, 8H), 7.48-7.35 (m, 6H), 7.34 (s, 1H), 7.21 (s, 1H), 7.17 (d, J=9.1 Hz, 2H), 6.91 (d, J=8.8 Hz, 2H), 5.60 (d, J=4.5 Hz, 1H), 5.32 (s, 2H), 4.52 (bs, 1H), 4.18 (t, J=9.5 Hz, 1H), 4.08 (m, 1H), 3.87-3.70 (m, 5H). $^{13}$C NMR (125 MHz, THF-d8): δ 161.1, 160.9, 159.1, 156.9, 145.4, 144.7, 143.0, 142.9, 141.8, 132.8, 132.6, 132.2 (t, J=5 Hz), 131.5 (t, J=5 Hz), 129.1, 129.0, 128.8, 128.6, 128.2, 124.5, 122.5, 122.0, 119.0, 118.2, 115.4, 114.5, 88.8, 78.8, 74.5, 70.4, 69.0, 61.9, 61.4. IR (KBr disc): 1596, 1455 cm$^{-1}$. ES-MS: m/z 771.6 [M−H]$^-$. HRMS [M+H]$^+$: 773.2717, C$_{41}$H$_{36}$BF$_2$N$_6$O$_7$ requires 773.2707.

4-[4-(4-[5-[5-(4-Hydroxyphenyl)-3-phenyl-1H-pyrrol-2-ylimino]-4-phenyl-5H-pyrrol-2-yl]-phenoxymethyl)-[1,2,3]triazol-1-yl]butyric acid (8b)

A solution of 2 (0.12 g, 0.21 mmol) and 4-azidobutyric acid (68 mg, 0.53 mmol) in THF:H$_2$O (15 mL, 3:1) was treated with a THF:H$_2$O (15 mL, 3:1) solution of Cu(0) (13 mg, 0.21 mmol), CuSO$_4$.5H$_2$O (7 mg, 0.042 mmol) and Na-ascorbate (21 mg, 0.1 mmol). The reaction mixture was heated at reflux for 3 h under N$_2$, cooled to rt and partitioned between EtOAc (25 mL) and water (25 mL). The aqueous layer was re-extracted with EtOAc (2×30 mL) and the combined organic layers were dried and evaporated to dryness under reduced pressure. Recrystallization from MeOH gave the product 8b as a red metallic solid (99 mg, 68%), m.p. 194-200° C. $^1$H NMR (300 MHz, MeOD): δ 8.16-8.12 (m, 8H), 7.9 (bs, 1H) 7.47-7.38 (m, 6H), 7.35 (s, 1H), 7.29 (s, 1H), 7.17 (d, J=8.8 Hz, 2H), 6.93 (d, J=8.2 Hz, 2H), 5.30 (s, 2H), 4.43 (t, 7 Hz, 2H), 2.47 (bs, 1H), 2.30 (m, 2H), 2.17 (m, 2H). $^{13}$C NMR (125 MHz, THF-d8): δ 172.7, 161.0, 160.9, 159.0, 157.0, 145.4, 144.7, 142.8, 141.9, 132.8, 132.6, 132.2 (t, J=5 Hz), 131.5 (t, J=5 Hz), 129.1, 129.0, 128.8, 128.6, 128.2, 128.2, 124.5, 122.6, 118.9, 118.2, 115.4, 114.5, 62.1, 48.8, 29.8, 25.5. IR (KBr disc): 3404, 3055, 1725, 1593 cm$^{-1}$. ES-MS: m/z 695.6 [M−H]$^-$. HRMS [M+Na]$^+$: 719.2382, C$_{39}$H$_{31}$BF$_2$N$_6$O$_4$Na requires 719.2366.

{2-[4-(4-{5-[5-(4-Hydroxyphenyl)-3-phenyl-1H-pyrrol-2-ylimino]-4-phenyl-5H-pyrrol-2-yl}-phenoxymethyl)-[1,2,3]triazol-1-yl]ethyl}carbamic acid t-butyl ester (8c)

A solution of 2 (0.33 g, 0.59 mmol) and (2-azidoethyl) carbamic acid t-butyl ester (0.19 g, 1.47 mmol) in THF:H$_2$O (40 mL, 3:1) was treated with a THF:H$_2$O (20 mL, 3:1) solution of Cu(0) (37 mg, 0.59 mmol), CuSO$_4$.5H$_2$O (18 mg, 0.18 mmol) and Na-ascorbate (58 mg, 0.3 mmol) at rt under N$_2$. The reaction mixture was heated under reflux for 3 h, cooled and partitioned between EtOAc (30 mL) and water (30 mL). The organic layer was dried and evaporated to dryness. Column chromatography on silica gel eluting with acetone:EtOAc (1:1) gave the product 8c as an dark green solid. (73.4 mg, 88%, m.p. 128-130° C.). $^1$H NMR (600 MHz, acetone-d6): δ 8.22-8.20 (m, 8H), 8.19 (bs, 1H), 7.54-7.45 (m, 7H), 7.42 (s, 1H), 7.22 (d, J=8.8 Hz, 2H), 7.02 (d, J=8.8 Hz, 2H), 6.20 (bs, 1H), 5.32 (s, 2H), 4.56 (t, J=5.9 Hz, 2H), 3.60 (t, J=5.9 Hz, 2H), 1.40 (s, 9H), (OH not observed). $^{13}$C NMR (125 MHz, THF-d8): δ 161.0, 160.8, 159.0, 157.3, 145.3, 144.7, 143.1, 142.2, 132.5, 132.3 (t, J=5 Hz), 131.7 (t, J=5 Hz), 129.3, 129.4, 129.3, 129.2, 129.1, 128.6, 128.5, 124.4, 122.7, 119.5, 118.8, 115.7, 114.9, 49.5, 40.4, 31.7, 27.6. IR (KBr disc): 3054, 1661, 1601 cm$^{-1}$. ES-MS: m/z [752.5]$^-$ [M−H]$^-$. HRMS [M+H]$^+$: 754.3160, C$_{42}$H$_{39}$BF$_2$N$_7$O$_4$ requires 754.3125.

Figure 5:
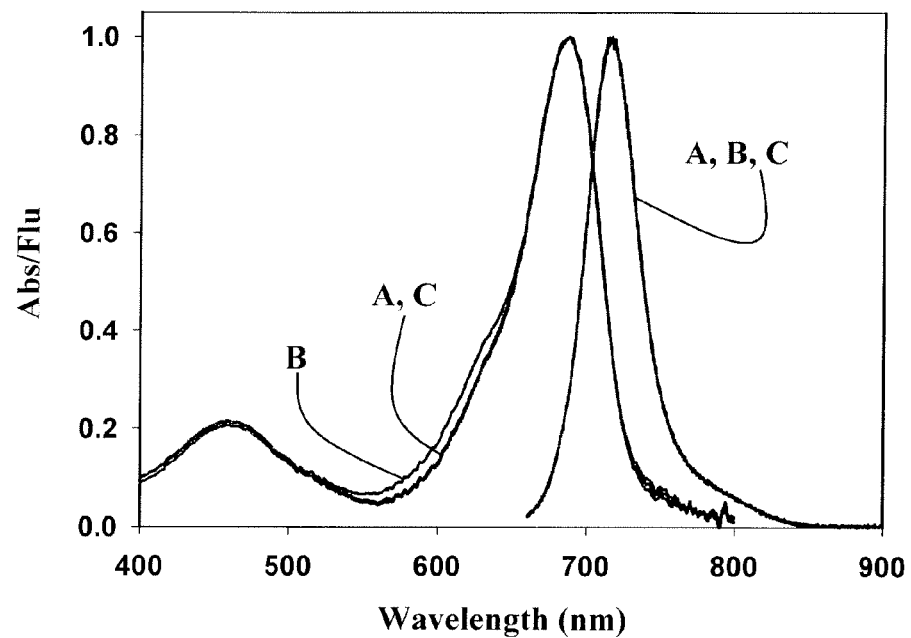
FIG. 5. Normalized UV-visible (5×10$^{-6}$ M) and fluorescence (5×10$^{-7}$ M) spectra of 8a ($\lambda_{max}$ 687/716 nm; A), 8b ($\lambda_{max}$ 687/716 nm; B) and 8c ($\lambda_{max}$ 687/716 nm; C) in MeOH.
Figure 6:
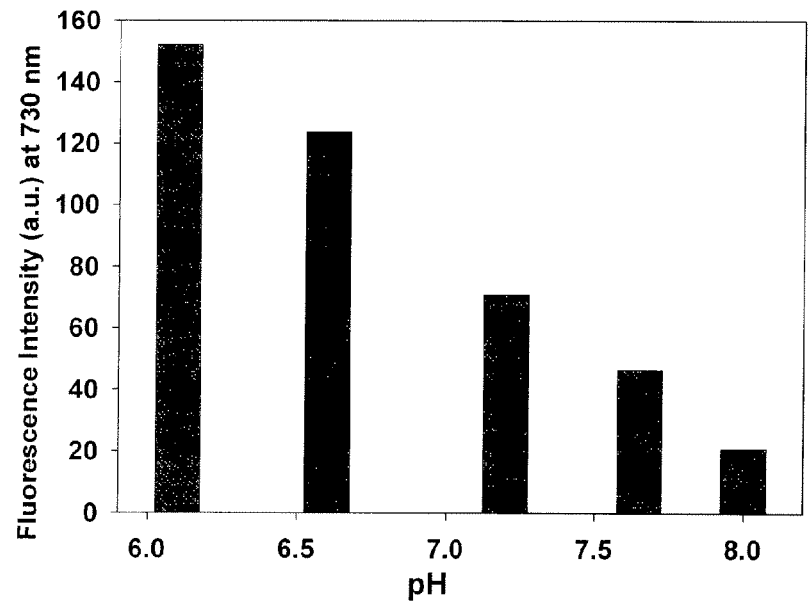
FIG. 6. Relative fluorescence intensity at 730 nm of 8a at pH 6.1, 6.6, 7.2, 7.6 and 8.0. Excitation at 640 nm, slit widths 20 nm, 5×10$^{-7}$ M in water/CrEL. I$_{NaCl}$=150 mmol/L.
Figure 9:
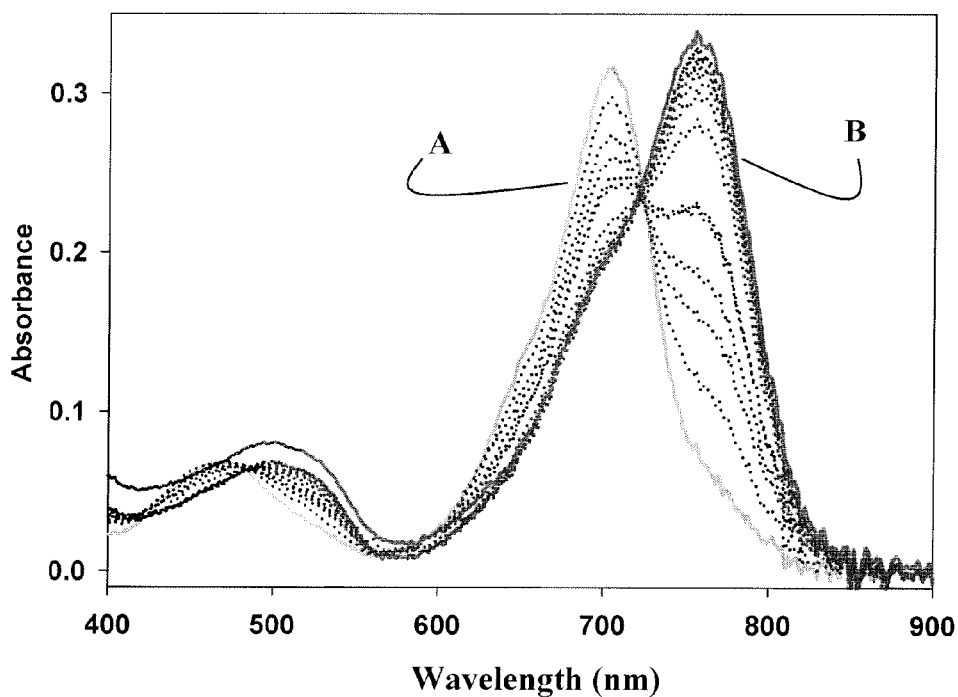
FIG. 9. UV-Visible pH Spectral Profile of 8a: pH=6.0=A trace; pH=9.0=B trace.
Figure 10:
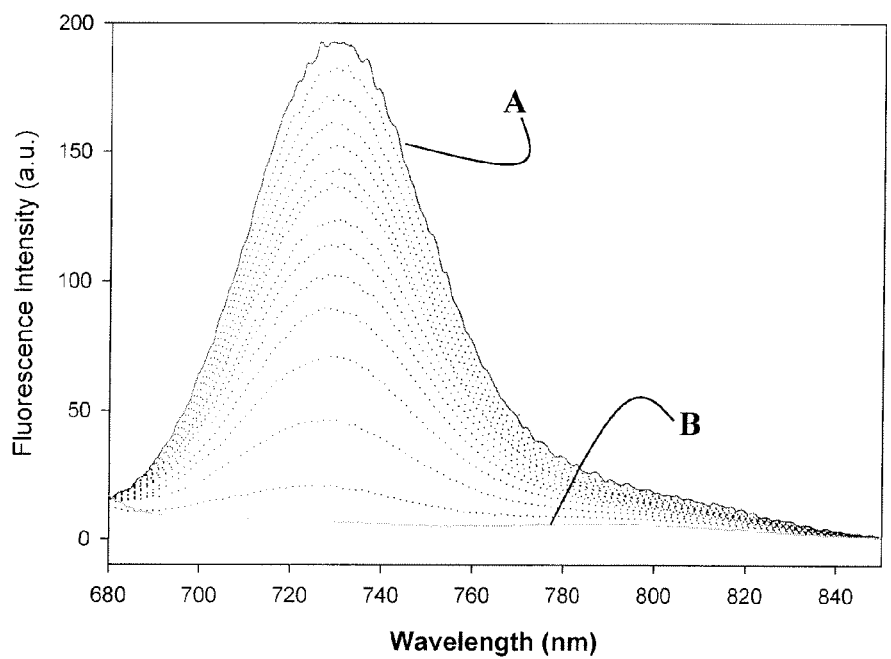
FIG. 10. Fluorescence pH Spectral Profile of 8a: pH=6.0=A trace; pH=9.0=B trace.
Figure 11:
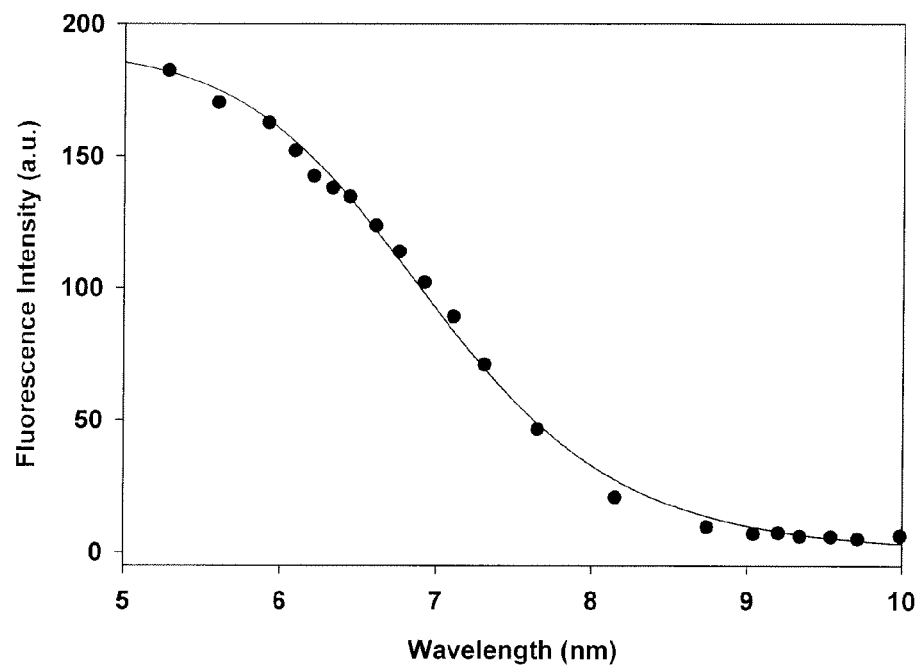

With reference to FIG. 5, it was observed that the UV-Vis/fluorescence spectra of 8a-c in methanol conveniently showed little difference from each other or from the alkyne derivative 2 demonstrating that the cycloaddition reaction had negligible effect on these spectral characteristics. As a representative example (FIGS. 9-11), the pH responsive nature of the galactose conjugated derivative 8a was examined and shown to have similar ground and excited state responses as that of 2 with pKa of 6.9. Analysis of the fluorescence intensity of 8a at five different pH values illustrated how a significant bias towards higher fluorescence intensity at low physiological pH regions was accomplished. For example, comparison of the measured fluorescence intensity difference from pH 6.1 to 7.2 was greater than 2 fold and the difference between 6.6 and 8 was 6 fold (FIG. 6).

Figure 7:
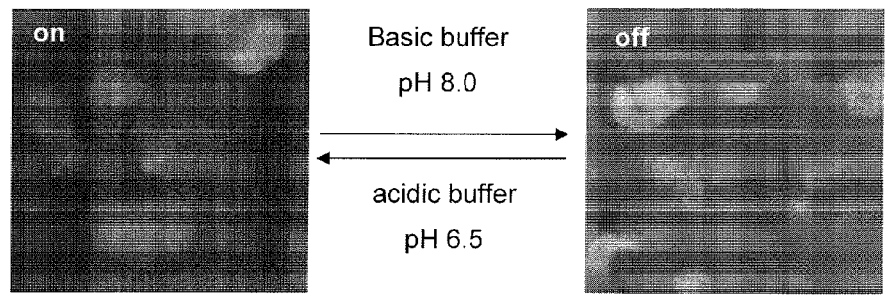
FIG. 7. Confocal fluorescence image of MDA-MB-231 cells following treatment with pH 8.0 and 6.5 buffers. 8a (red color) and nuclear DAPI stain (blue color).
Figure 8:
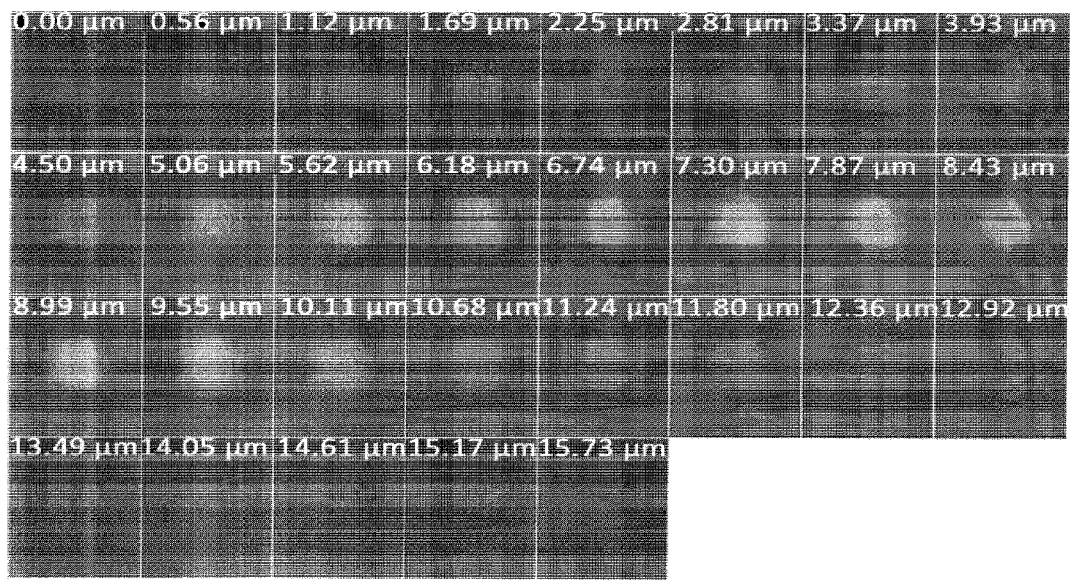
FIG. 8. Confocal Laser Scanning Microscopy Z-Stack Imaging of 8a in CAKI-1 cells.

Demonstration of cell internalization of 8a was achieved by incubation with MDA-MB-231 cells for 1 h followed by blue nuclear co-staining with 4,6-diamidino-2-phenylindole (DAPI). Dual-color imaging with confocal laser scanning microscopy showed a distinct red emission from 8a localised to the cytosol (FIG. 8). Illustrative reversible on/off switching of intracellular 8a could be achieved by treating a population of dual-stained cells with aqueous carbonate buffer of pH 8.0 or acidic buffer of pH 6.6 (FIG. 7), and as illustrated below.

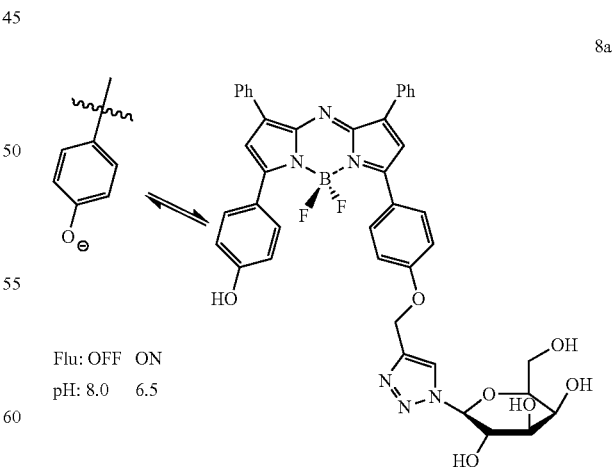

Imaging of the same cell population following addition of basic buffer showed almost complete quenching of the red emission of 8a with the blue nuclear DAPI emission still clearly visible. In contrast following the addition of pH 6.6 buffer to the cells the emission from 8a was re-established. The difference in averaged whole cell red fluorescence taken from off-cells to on-cells was six-fold (FIG. 7).

In summary, an efficient synthesis and photophysical characteristics of a new pH responsive fluorochrome platform with emission at 730 nm has been demonstrated.

EXAMPLE 3(A)

Compounds 9, 10, 11a and 11b: Compounds Comprising a Water-solubilizing Group and a Conjugation Group In this example, the synthesis and spectral properties of the first fluorochromes based on the prior art fluorophore scaffold 1, and capable of amine conjugations, are presented. The strategy was to exploit compound 6 as a key synthetic starting point to produce compounds of the formula (I), specifically of the formula (IA).

Synthetic manipulation via alkylation of phenolic rings by oxygen alkylation was utilized to introduce to water-solublizing group on one ring of compound 6 and a conjugation group on the other, as indicated below. It will be appreciated that the positions of the water-solubilizing group and conjugation group may be reversed.

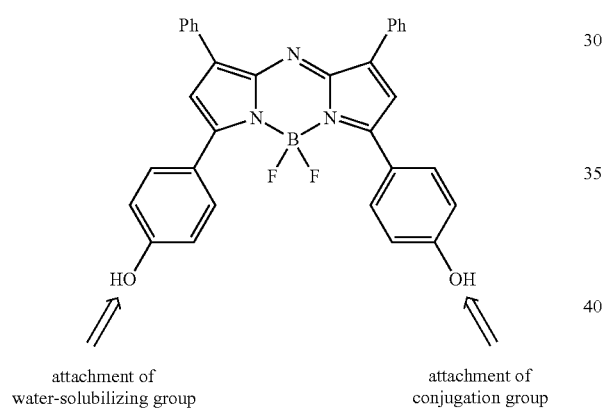

For this example, the approach was to impart partial aqueous solubility to the fluorophore by introducing a polyether on one phenol ring. It was anticipated that a single polyether alone would not be sufficient to impart complete water solubility but perhaps sufficient to facilitate the conjugation reaction. While other charged solubilizing groups are currently under investigation this approach offers the potential to produce an overall charge neutral fluorochrome which may limit the complications of non-covalent charge interactions of fluorophore and the conjugating bio-molecule. The other phenol ring would be substituted with a spacer unit and a conjugatable activated ester group. Two different activated esters, N-hydroxysuccinimide and a sulfonated N-hydroxysulfosuccinimide sodium salt were investigated, the latter providing enhanced aqueous solubility without introducing charge directly onto the fluorophore.

The synthetic challenge of functionalising the equivalent phenols of 6 with differing substituents was achieved utilizing simultaneous Mitsunobu coupling of 6 with two different alcohols. It was found that rather than reacting the phenols in successive steps conditions were optimised to achieve this in a single operation. With reference to Scheme 3. Fluorochrome synthesis.

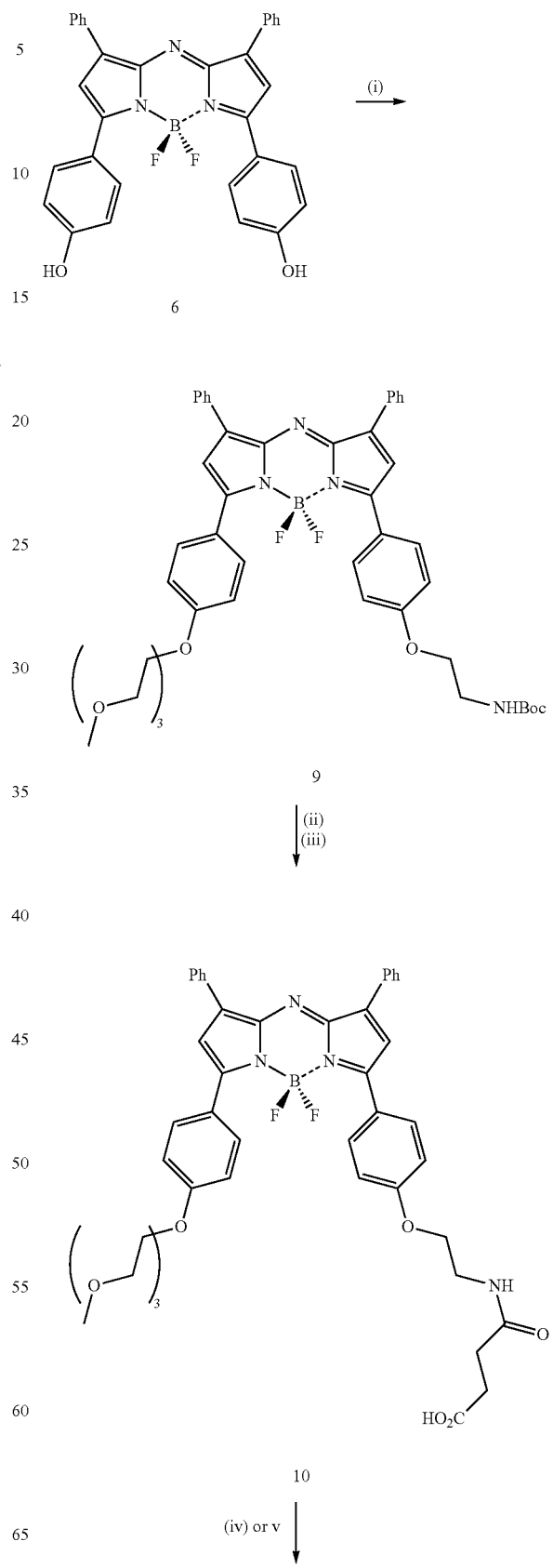

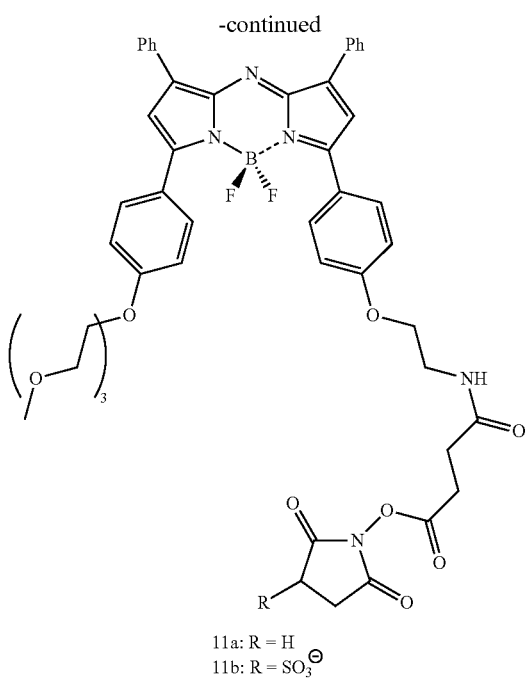

11a: R = H
11b: R = SO$_3^\ominus$

Reagents and conditions: (i) triethylene glycol monomethyl ether, N-Boc ethanolamine, PPh$_3$, DIAD, THF, r.t., 16 hr, 39%. (ii) TFA, CH$_2$Cl$_2$, 2 hr, rt. (iii) succinic anhydride, DIPEA, r.t., 3 h, 57%. (iv) N-hydroxysuccinimide, EDCI, DMAP (cat.) CH$_2$Cl$_2$, r.t., 16 hr, 99%. (v) N-hydroxysulfosuccinimide sodium salt, EDCI, DMAP (cat.), DMSO, r.t., 16 hr.

Chromatographic separation of 9 from unwanted symmetrical coupling products was achievable due to the large differences in retention factors on silica. This approach proved superior to a stepwise introduction of phenolic substituents due to poorer overall conversions and more difficult purifications. The introduction of a four-carbon spacer unit was achieved by the Boc-deprotection of 9 with TFA in CH$_2$Cl$_2$ and subsequent reaction with by reaction with succinic acid anhydride yielding the carboxylic acid 10. Subsequently, 10 was transformed into the activated ester 11a or 11b by coupling with N-hydroxysuccinimide or N-hydroxysulfosuccinimide respectively (Scheme 3). Fluorochrome 11a was a bench stable solid and due to the higher reactivity of 11b it was directly used upon generation.

Further details of the products 9, 10, 11a and 11b and synthesis thereof are provided below.

Synthesis of 9. Compound 6 (630 mg, 1.2 mmol), triethylene glycol monomethyl ether (294 μL, 1.8 mmol), N-Boc ethanolamine (285 μL, 1.8 mmol) and PPh$_3$ (1.257 g, 4 mmol) were dissolved in dry THF (100 ml). DIAD (969 μL, 4 mmol) in dry THF (5 mL) was slowly (20 min) added to the solution and the reaction mixture stirred at r.t. for 16 hr. Solvent was removed under reduced pressure and dark green residue was chromatographed (silica, AcOEt/cyclohexane gradient of 1:1, to 4:1). Middle green fraction was isolated (R$_f$=0.35, silica, AcOEt/cyclohexane, 4:1), evaporated and rechromatographed (silica, AcOEt/CH$_2$Cl$_2$, 1:4) to give 9 (380 mg, 39%) as a dark green solid. M.p.=51-53° C. δ$_H$ (500 MHz, CDCl$_3$): 1.47 (s, 9H), 3.38 (s, 3H), 3.54-3.58 (m, 4H), 3.67 (t, J=4.6 Hz, 2H), 3.70 (t, J=4.6 Hz, 2H), 3.76 (t, J=4.6 Hz, 2H), 3.90 (t, J=4.6 Hz, 2H), 4.11 (t, J=4.6 Hz, 2H), 4.22 (t, J=4.6 Hz, 2H), 4.99 (br s, 1H), 6.97-7.06 (m, 6H), 7.39-7.48 (m, 6H), 8.04-8.10 (m, 8H). δ$_C$ (125 MHz, CDCl$_3$): δ 161.2, 160.8, 158.3, 157.8, 155.8, 145.4, 143.2, 132.4, 131.6, 129.2, 128.5, 124.5, 124.2, 118.7, 118.5, 114.8, 114.6, 79.6, 71.9, 70.9, 70.7, 70.6, 69.6, 67.6, 67.3, 59.0, 40.0, 28.4. HRMS (ESI) calcd for C$_{46}$H$_{49}$N$_4$O$_7$NaBF$_2$ [M+Na$^+$]$^+$: 841.3560. found 841.3571. IR (KBr disc) cm$^{-1}$: 1504, 1603, 1710. λ$_{abs}$ (CHCl$_3$, ε×10$^{-3}$) 689 (87.1), 450 (17.3), 367 (11.9), 318 (26.0) nm. λ$_{emiss}$ (CHCl$_3$): 717 nm, Φ 0.36 (1 used as standard Φ=0.36).

Synthesis of 10. Compound 9 (164 mg, 200 μmol) was dissolved in CH$_2$Cl$_2$ (10 mL), TFA (1 mL) was slowly added and the reaction mixture was stirred at r.t. for 2 hr. Saturated aqueous NaHCO$_3$ was added and the resulting suspension extracted with CH$_2$Cl$_2$ (2×30 mL) The combined organic phases were washed with water, dried over Na$_2$SO$_4$ and evaporated to dryness. The resulting green residue was dissolved in dry THF (10 mL), treated with succinic anhydride (24 mg, 240 μmol) and DIPEA (70 μL, 400 mmol) and stirred at r.t. for 3 hr. Solvent was removed under reduced pressure and the residue chromatographed (silica, MeOH/CH$_2$Cl$_2$, 2:8) to give 10 (93 mg, 57%) as a dark green solid. M.p.=72-74° C. δ$_H$ (500 MHz, CDCl$_3$): 2.45 (t, J=6.2 Hz, 2H), 2.65 (t, J=6.2 Hz, 2H), 3.36 (s, 3H), 3.52-3.55 (m, 2H), 3.56-3.61 (m, 2H), 3.62-3.68 (m, 4H), 3.70-3.74 (m, 2H), 3.85 (t, J=4.7 Hz, 2H), 4.01 (t, J=4.7 Hz, 2H), 4.16 (t, J=4.7 Hz, 2H), 6.45 (s, 1H), 6.87-7.01 (m, 6H), 7.34-7.44 (m, 6H), 7.92-8.08 (m, 8H). δ$_C$ (100 MHz, CDCl$_3$): 26.9, 58.9, 66.5 (br), 67.5, 69.4, 70.4, 70.5, 70.7, 71.8, 114.5, 114.7, 118.4, 118.6, 124.1, 124.2, 128.3, 128.4, 129.0, 129.14, 129.17, 131.5 (br), 131.6 (br), 132.1, 132.4, 142.56, 142.59, 142.7, 145.0, 145.2, 157.5, 157.8, 160.7, 161.0. HRMS (ESI) calcd for C$_{45}$H$_{45}$N$_4$O$_8$NaBF2 [M+Na$^+$]$^+$: 841.3196. found 841.3215. IR (KBr disc) cm$^{-1}$: 1509, 1602, 1655. λ$_{abs}$ (CHCl$_3$) 689 nm. λ$_{emiss}$ (CHCl$_3$): 717 nm.

Synthesis of 11a. Compound 10 (27 mg, 33 μmol), N-hydroxysuccinimide (5.2 mg, 45 μmol) and DMAP (cat.) were dissolved in dry DCM (5 mL). 1-Ethyl-3-(3'-dimethylaminopropyl)carbodiimide (EDCI) (8.8 mg, 45 μmol) was added at 0° C. and the resulting mixture stirred at r.t. for 16 hr. The organic phase was washed with HCl (1 M, 1 mL), water (2 mL) and dried over Na$_2$SO$_4$. Solvent was removed under reduced pressure to give 11a (28 mg, 99%) as a dark green solid. δ$_H$ (500 MHz, CDCl$_3$): 2.54 (t, J=7 Hz, 2H), 2.57 (s, 4H), 2.91 (t, J=7 Hz, 2H), 3.30 (s, 3H), 3.46-3.49 (m, 2H), 3.56-3.64 (m, 6H), 3.65-3.69 (m, 2H), 3.81 (t, J=5 Hz, 2H), 4.01 (t, J=5 Hz, 2H), 4.13 (t, J=5 Hz, 2H), 6.18 (t, J=5.6 Hz, 1H), 6.87-6.97 (m, 6H), 7.31-7.39 (m, 6H), 7.95-8.00 (m, 8H). HRMS (ESI) calcd for C$_{49}$H$_{48}$BF$_2$N$_5$O$_{10}$Na [M+Na$^+$]$^+$: 938.3360. found 938.3886. IR (KBr disc) cm$^{-1}$: 1603, 3054.

Synthesis of 11b. Compound 10 (5 mg, 6.11 μmol), N-hydroxysulfosuccinimide sodium salt (1.4 mg, 6.4 μmol), 1-ethyl-3-(3'-dimethylaminopropyl)carbodiimide hydrochloride (1.2 mg, 6.2 μmol) and DMAP (cat.) were dissolved in dry in DMSO (200 μL) were stirred at r.t. for 16 hr, under nitrogen. Monitoring the reaction by reverse phase HPLC (C-18 column eluting with acetonitrile water 7:3) complete consumption of starting material. The solution was used directly for conjugation experiments.

Figure 12:
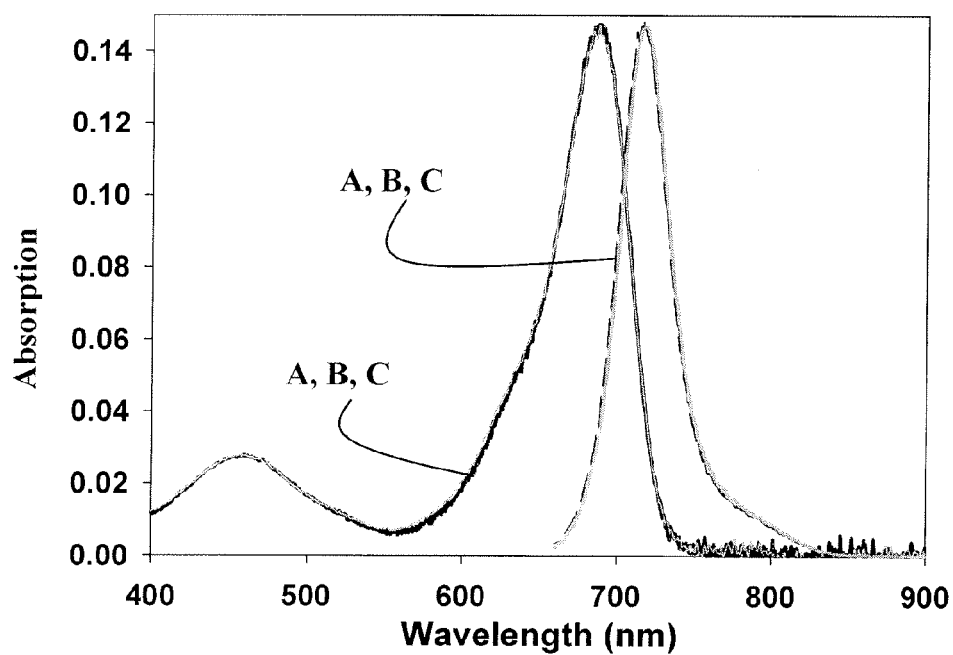
FIG. 12. Normalised absorption ($5 \times 10^{-6}$ M) and emission ($5 \times 10^{-7}$ M) spectra of 9 (A), 10 (B) and 12 (C) in EtOH.

Spectroscopic analysis of 9 and 10 as representative constituent building blocks of the fluorescent probes showed very little variance in their properties with absorbance maxima at 688 and 691 nm respectively and fluorescence maxima at 714 nm for both (Table 4, FIG. 12). Both had extinction coefficient in excess of 80,000 and good fluorescence quantum yields (Table 4).

TABLE 4

Spectroscopic properties[a]

| Entry | Comp. | $\lambda_{max}$abs nm[b] | $\epsilon$ M$^{-1}$cm$^{-1}$ | $\lambda_{max}$emiss nm[c,d,e] | $\Phi_f$[f] |
|---|---|---|---|---|---|
| 1 | 9 | 688 | 95000 | 714 | 0.23 |
| 2 | 10 | 691 | 85500 | 714 | 0.20 |
| 3 | 12 | 691 | 74500 | 714 | 0.22 |

[a]In ethanol.
[b]Conc 5 × 10$^{-6}$ M.
[c]Conc 5 × 10$^{-7}$ M.
[d]Excitation at 640 nm.
[e]Slit widths 5 nm.
[f]1 used as standard.[6a]

Figure 13:
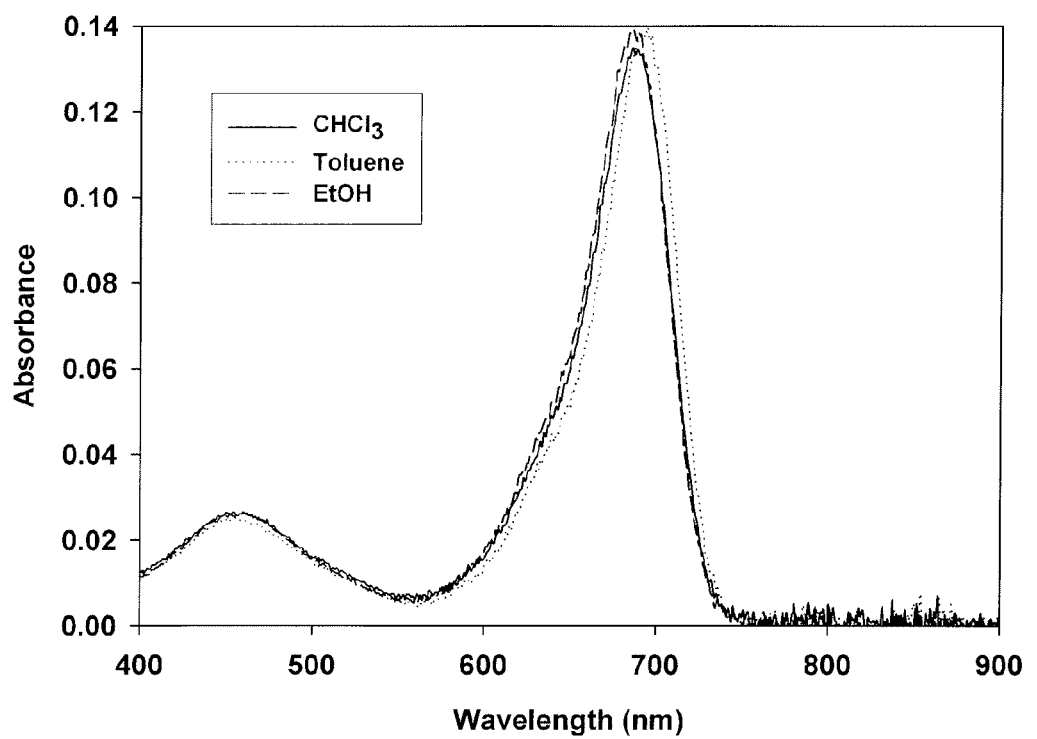
FIG. 13. UV-Visible and fluorescence spectra of 9 in different solvents.
Figure 13:
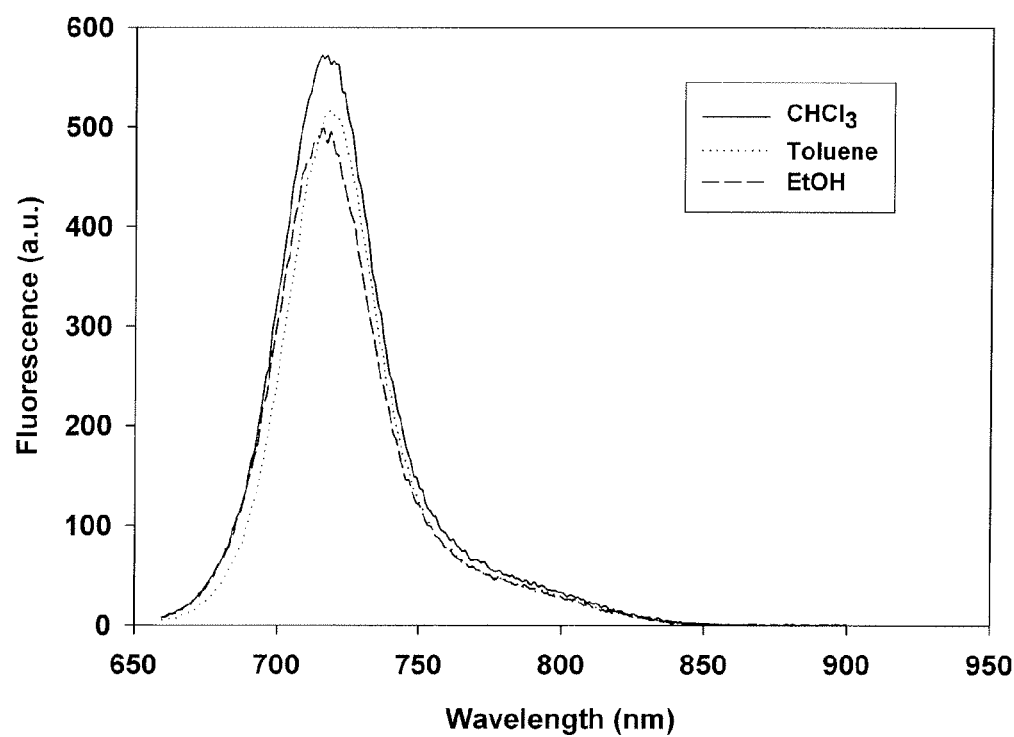
Figure 14:
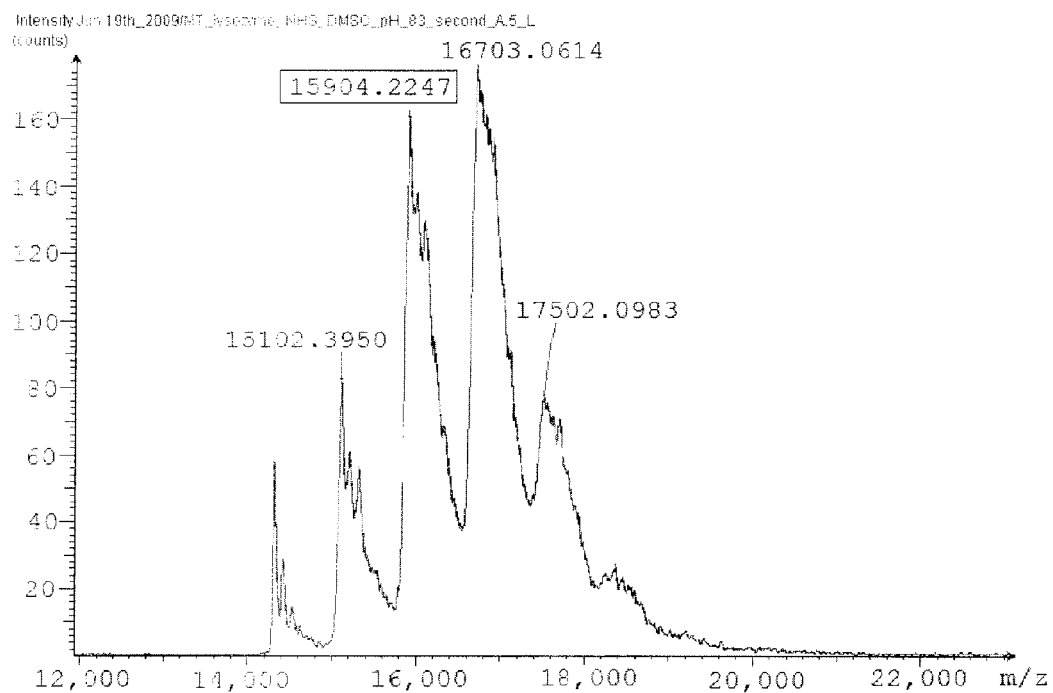
FIG. 14. Conjugation of 11a with lysosyme in DMSO/water.
Figure 15:
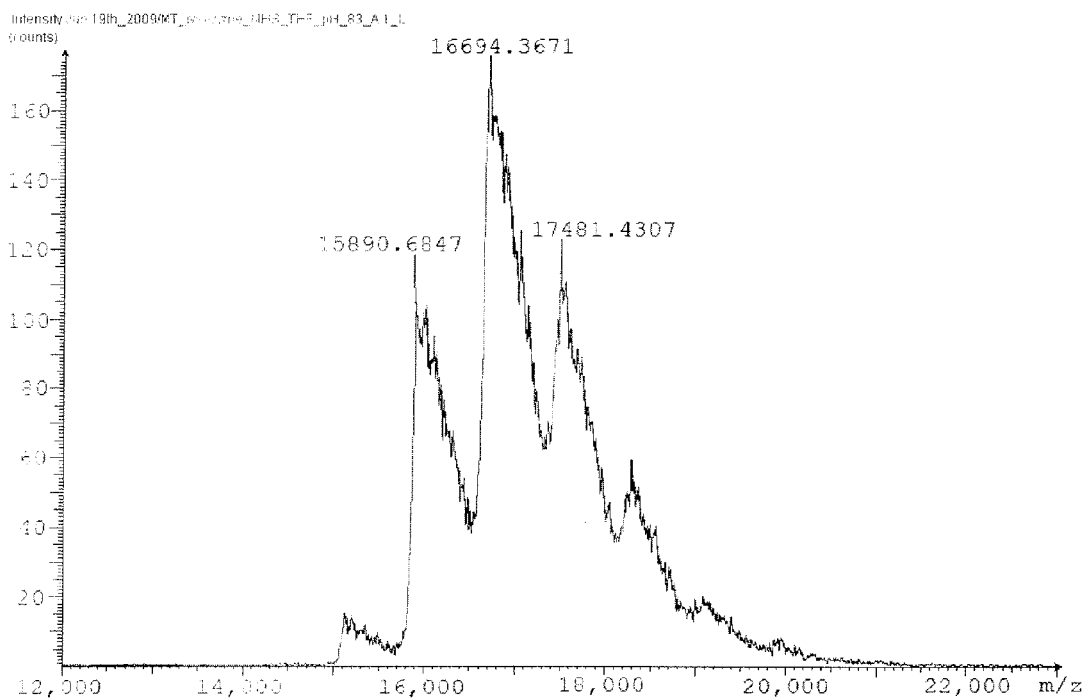
FIG. 15. Conjugation of 11a with lysosyme in THF/water.
Figure 16:
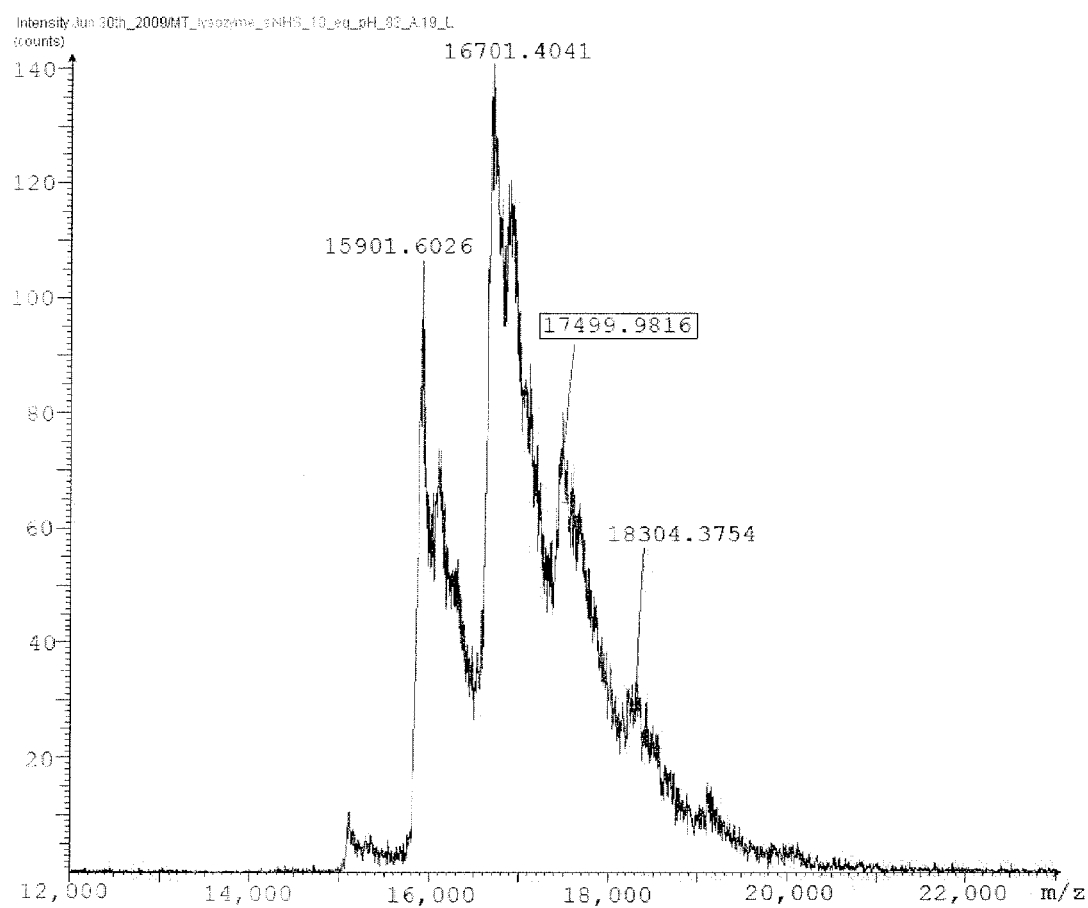
FIG. 16. Conjugation of 10 equiv. of 11b with lysosyme in 0.1 M $NaHCO_3$ at pH=8.3.
Figure 17:
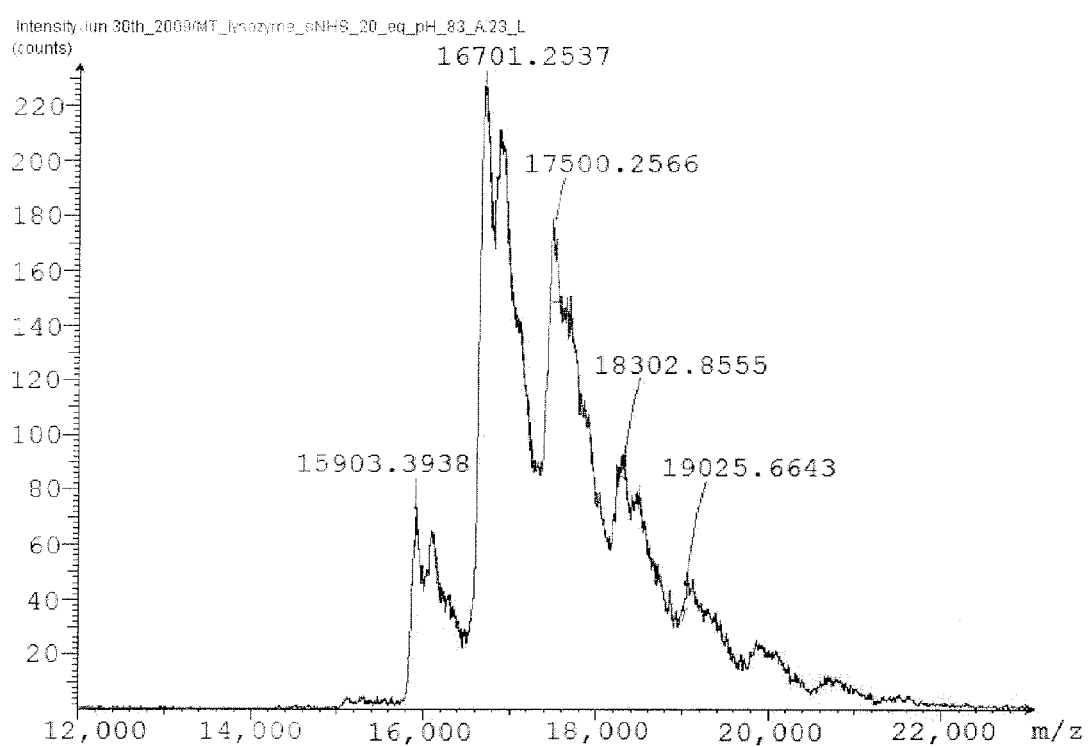
FIG. 17. Conjugation of 20 equiv. of 11b with lysosyme in 0.1 M $NaHCO_3$ at pH=8.3.

Their spectral features were also relatively insensitive to solvent polarity (FIG. 13).

EXAMPLE 3(B)

Dye Conjugates from Compounds 11a and 11b

EXAMPLE 3(B)(I)

Activated succinimide esters typically react with the N-terminus α-amino group and the amine of lysine constituent amino acids. With reference to Scheme 3(A), and as described further below, illustrative coupling of 11a in organic and 11b in aqueous solutions with N$_\epsilon$-Boc-L-lysine rapidly gave amino acid substituted derivative 12 in good yields in both organic and aqueous solutions.

Scheme 3(A). Coupling with Boc-protected lysine.

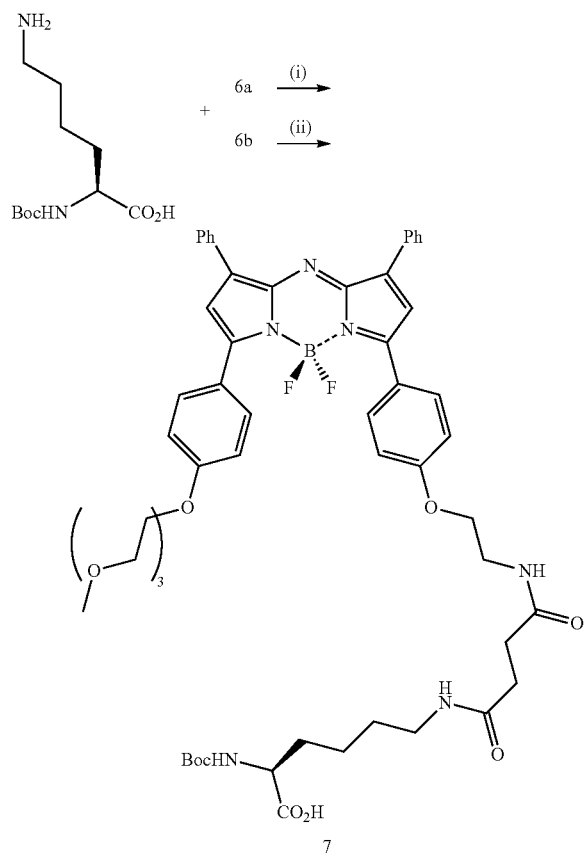

Reagents and conditions: (i) N$_\epsilon$—Boc—L-lysine, DIPEA, CH$_3$CN, rt, 0.5 hr.
(ii) N$_\epsilon$—Boc—L-lysine, pH 8.3 NaHCO$_3$ buffered water, rt, 5 min.

Conjugation with N$_\epsilon$-Boc-L-lysine, Synthesis of Compound 12

With reference to Scheme 3(A), starting from 11a: Activated ester 11a (11 mg, 12 μmol), Boc-lysine (6 mg, 24 μmol) and DIEA (6.4 μL, 36 μmol) were suspended in dry acetonitrile (5 mL) and stirred for 2 h under the nitrogen atmosphere. Solvent was removed and the residue was chromatographed (silica, CH$_2$Cl$_2$/MeOH, 9:1 then 8:2, 7:3) affording 12 (2 mg, 16%) as green solid.

Starting from 11b: Carboxylic acid 10 (5 mg) was activated according to the procedure described for 11b. Resulting solution was added to Boc-lysine (15 mg, 30.5 μmol) solution in 0.1M NaHCO$_3$ (1 mL, pH=8.3). After 15 min the resulting mixture was acidified with 2N HCl and extracted with AcOEt. Subsequent chromatography (silica, CH$_2$Cl$_2$/MeOH, 7:3) afforded 12 as green solid (4 mg, 63%). $^1$H NMR (500 MHz, CDCl$_3$) 1.26-1.46 (br m, 4H), 1.39 (s, 9H), 1.55-1.65 (br m, 2H), 1.70-1.80 (br m, 2H), 2.25-240 (br m, 2H), 2.46-2.54 (br m, 2H), 3.12-3.18 (br m, 2H), 3.34 (s, 3H), 3.52-3.55 (m, 2H), 3.50-3.53 (m, 2H), 3.60-3.66 (m, 4H), 3.68-3.71 (m, 2H), 3.82 (br t, 2H), 3.95-4.02 (br m, 3H), 4.10-4.16 (br m, 2H), 5.83 (s, 1H), 6.83-6.97 (m, 6H), 7.05 (br s, 1H), 7.22 (br s, 1H), 7.29-7.40 (m, 6H), 7.90-8.05 (m, 8H). $^{13}$C NMR (100 MHz, CDCl$_3$) δ: 173.2, 172.8, 161.1, 160.8, 157.8, 156.1, 145.2, 145.1, 142.9, 118.6, 114.7, 114.6, 71.8, 70.8, 70.5, 70.4, 69.5, 67.5, 66.6, 59.0, 28.5. HRMS (ESI) found: 1069.5371, exact calcd mass: 1069.4670 (C$_{56}$H$_{65}$BF$_2$N$_6$O$_{11}$Na$^+$). IR (KBr disc) cm$^{-1}$: 740, 1265, 1475, 1506, 1603, 1657, 3055.

The spectroscopic properties of 12 differed very little from 10 (Table 4, FIG. 12).

EXAMPLE 3(B)(II)

Next the conjugation of 11a and b with the 14.4 kDa protein lysosyme was examined. Lysosyme was chosen as a substrate as it has six potentially reactive lysine residues in addition to the N-terminal amine. Conjugation of lysosyme with five equivalents of 11a was carried out in 1:1 water/DMSO and 4:1 water/THF mixtures and 11b was coupled in pH 8.3 NaHCO$_3$ buffered water, as described below (for 11b).

Conjugation of 11b with Lysozyme 1 eq: Lysozyme (18 mg, 1.2 μmol) was dissolved in 0.1 M NaHCO$_3$ (1.8 mL, pH=8.3). Dye solution (40 μL) was added, resulting in formation of green precipitate. After 1 h incubation in darkness, the precipitate was centrifuged and supernatant was removed. Distilled water (400 μL) was added, the resulting suspension was vortexed and centrifuged again. Precipitate was washed that way additional 2 times and it was used for the analysis without any further purification.

5 eq: Lysozyme (18 mg, 1.2 μmol) was dissolved in 0.1 M NaHCO$_3$ (1.8 mL, pH=8.3). Dye solution (200 μL) was added, resulting in formation of green precipitate. After 1 h incubation in darkness, the precipitate was washed as it was described for coupling with 1 eq of the dye.

10 eq: Lysozyme (3.6 mg, 0.25 μmol) was dissolved in 0.1 M NaHCO$_3$ (1 mL, pH=8.3). Dye solution was added (80 μL), resulting in formation of green precipitate. After 1 h incubation in darkness, the precipitate was purified as it was described above.

20 eq: Lysozyme (3.6 mg, 0.25 μmol) was dissolved in 0.1 M NaHCO$_3$ (1 mL, pH=8.3). Dye solution was added (160 μL), resulting in formation of green precipitate. After 1 h incubation in darkness, the precipitate was purified as it was described above.

Coupling was effectively achieved in all cases and confirmed by MALDI-TOF mass spectrometry and HPLC analysis (FIGS. 14, 15, 16 and 17). For the MALDI-TOF data, sample preparation was as follows: lysozyme conjugates were dissolved directly in matrix solution (saturated solution of sinapic acid in acetonitrile/water 1:1 mixture containing 0.1% TFA).

Figure 19:
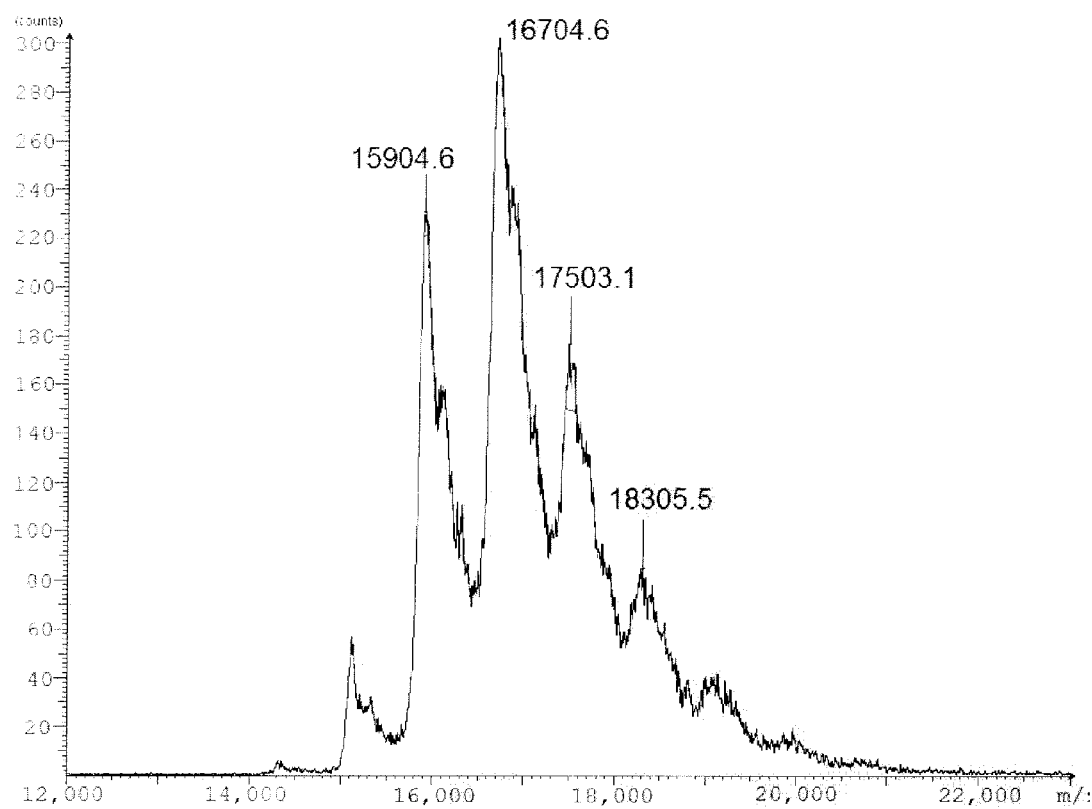
FIG. 19. MALDI-MS of lysosyme conjugated with five equiv. of 6b. Di-conjugate 15,904; tri-conjugate 16,704; tetra-conjugate 17,503; penta-conjugate 18,305.

Encouragingly the MALDI analysis of the conjugates identified a distribution of mono to penta conjugates from both 11a and 11b illustrating the highly reactive nature of the fluorochromes. As might be expected the coupling of 11b was superior to that of 11a with a the tri-conjugates being the most abundant, with each conjugate separated by an approximate mass of 800 amu (FIG. 19). This high loading achievable illustrates the effectiveness of the coupling reaction. The use of greater ratios of fluorochrome 11b (20 equiv.) to protein increased the loading levels with the tetra to hexa-conjugates being the most abundant.

A further confirmatory coupling of 11b with the 23.3 kDa protein trypsin in PBS at pH 7.5 was carried out, as described below.

Conjugation of 11b with Trypsin 1 mL of trypsin-EDTA solution 10× (containing 0.5% trypsin, 0.2% EDTA, without phenol red, in saline) was diluted with PBS (1 mL, pH=7.0) and pH was adjusted to 7.5. Dye solution (35 µL) was slowly added and the protein was incubated for 1 h in darkness. Resulting solution was loaded on BIO-GEL column (P-2, 1 cm diameter, 15 cm long, eluted with distilled water) affording desalted protein solution, that was used directly for the analysis.

Figure 18:
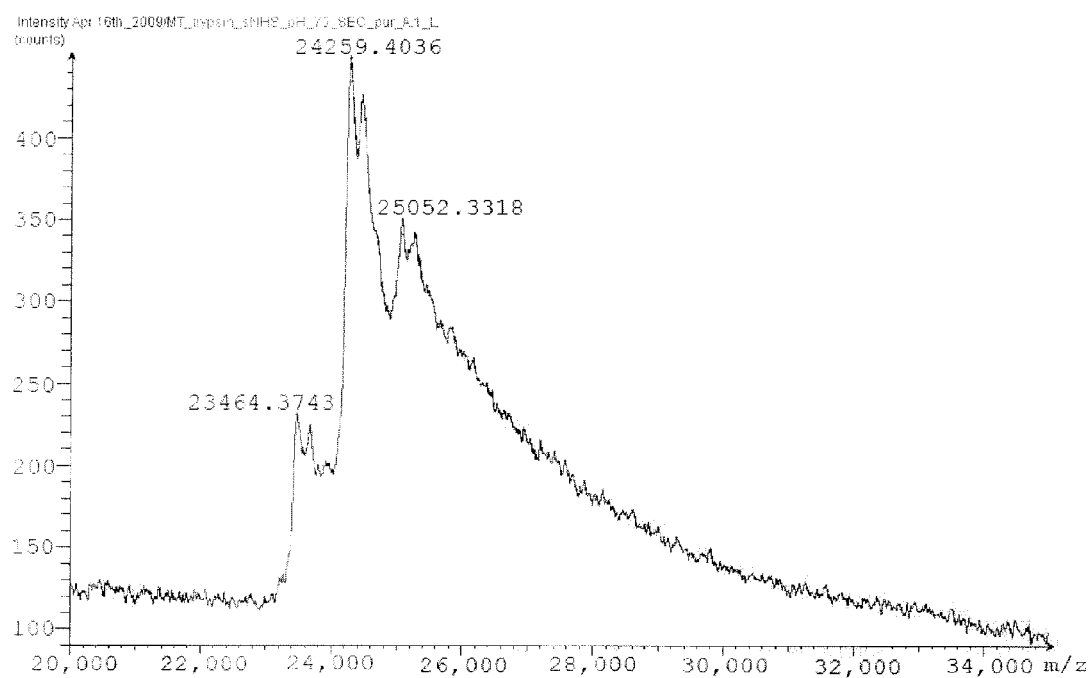
FIG. 18. Conjugation of 10 equiv. of 11b with trypsin in PBS at pH=7.5.

This coupling of 11b with the 23.3 kDa protein trypsin in PBS at pH 7.5 gave a distribution of mono and di functionalised enzyme (FIG. 18). For the MALDI-TOF data, sample preparation was as follows: fractions obtained after BIO-GEL filtration were diluted with matrix solution (saturated solution of sinapic acid in acetonitrile/water 1:1 mixture containing 0.1% TFA).

Figure 20:
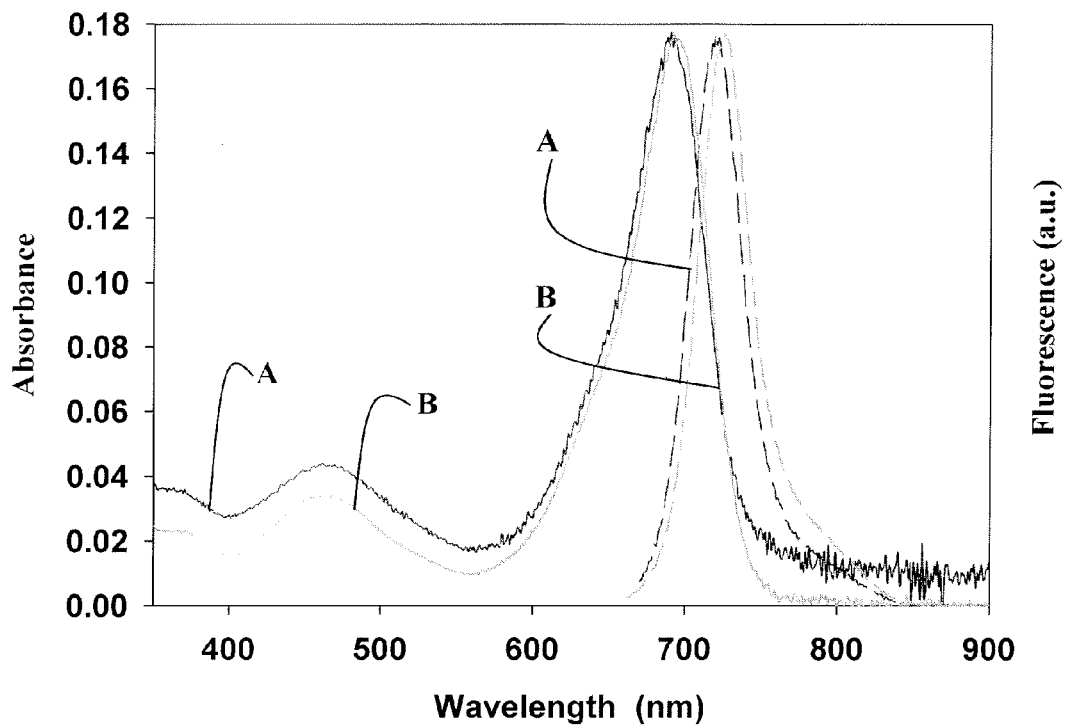
FIG. 20. Normalised absorption (left) and emission (right) spectra of lysozyme (A), and trypsin (B) in aqueous PBS.

Spectral analysis of the lysoyme and trypsin conjugates show that the attractive spectral features of this chromophore such as sharp absorption and emission bands are retained (FIG. 20). Importantly the emission maxima of both were above 720 nm.

In summary, in Example 3, a short synthesis to a new NIR fluorchrome has been described, and its potential for effective amine conjugations with amino acids and proteins has been illustrated.

EXAMPLE 4

Compounds Comprising Two Water-solubilizing Groups or Two Conjugation Groups

Water soluble $BF_2$-chelated tetraarylazadipyrromethanes are prepared in this Example, and their spectroscopic properties and in vitro delivery are demonstrated. It has previously been reported that inclusion of an electron donating para-alkoxy group on the aryl rings a to the pyrrole nitrogen the prior art compound results in significant emission bathochromic shift of ~40 nm when compared to the unsubstituted derivative. As such, this substitution pattern was included in the structural core of the sensitisers with additional carboxylic acid, sulfonic acid and ammonium salt functional groups introduced to provide aqueous solubility.

The synthesis of bis-carboxylic acid and bis-sulfonic acid derivatives, 16 and 17 respectively, which are both compounds of the formula (I), specifically of the formula (IA), had a common starting point of the bis-phenol substituted azadipyrromethene 13, which is readily accessible from 1-(4-hydroxyphenyl)-3-phenylpropenone in two synthetic steps. With reference to Scheme 4, alkylation of both phenols of 13 with methyl bromoacetate gave the corresponding diester 14 in high yields, following purification by silica gel chromatography (Scheme 4).

Saponification of 15 with potassium trimethylsilanolate (TMSOK) in THF at room temperature afforded the bis-carboxylic acid derivative 16. It will be appreciated, however, that 16 may alternatively be synthesised from compound 6. The optimised conditions to the bis-sulfonic acid analogue required $BF_2$ chelation of 3 to generate 6 and subsequent reaction with propane-1,3-sultone in presence of $K_2CO_3$ providing 17, in moderate yield, as a dark green powder following chromatographic purification.

Scheme 4. Synthesis of bis-anionic substituted derivatives.

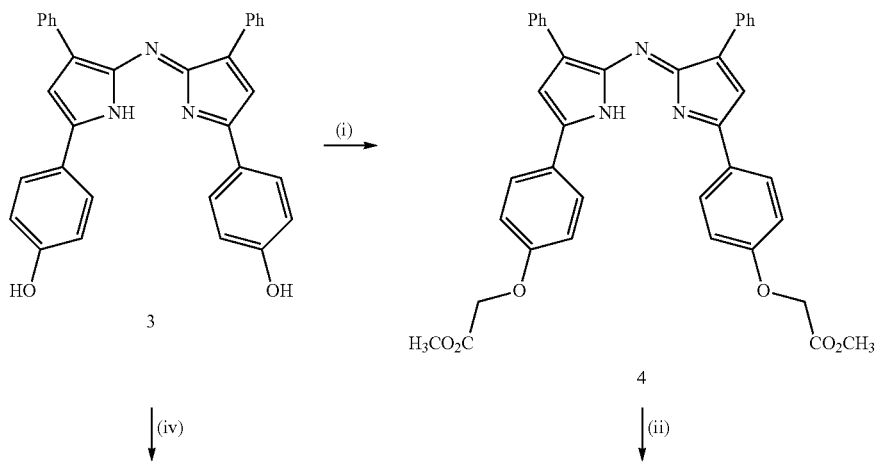

-continued

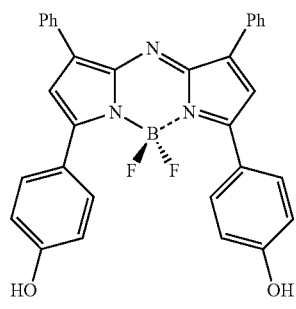

7

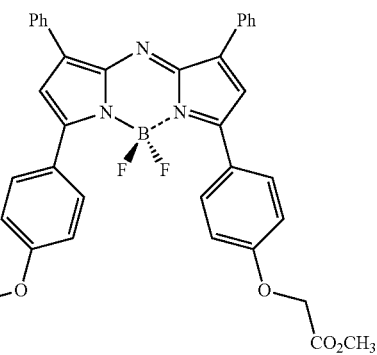

5

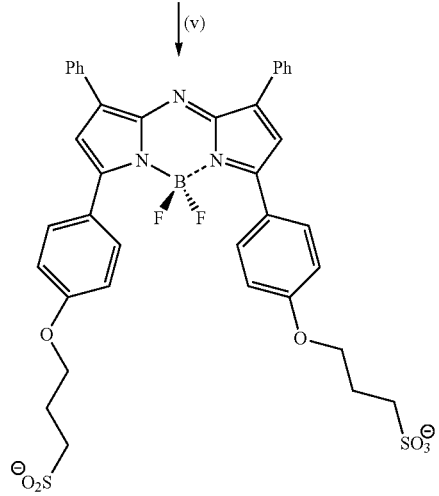

8

Reagents and conditions: (i) methyl bromoacetate, K₂CO₃, acetone, reflux, 16 hr, 89%. (ii) BF₃·OEt₂, DIEA, CH₂Cl₂, rt, 24 hr, 73%.
(iii) TMSOK, THF, rt, 3 hr, 34%. (iv) BF₃·OEt₂, DIEA, CH₂Cl₂, rt, 16 hr, 78%. (v) propane-1,3-sultone, K₂CO₃, acetone, reflux, 6 hr, 41%.

Further details of the products 14, 15, 16 and 17 and synthesis thereof are provided below.

Compound 14:

Compound 13 (481 mg, 1 mmol), methyl bromoacetate (368 μL, 4 mmol), NaI (300 mg, 2 mmol) and K₂CO₃ (550 mg, 4 mmol) were placed in round bottom flask. Acetone (100 mL) was added and the reaction mixture heated under reflux for 16 hr. The solvent was removed, the residue was dissolved in CH₂Cl₂, washed with water, dried over Na₂SO₄ and evaporated to dryness. Crystallization from ethyl acetate/cyclohexane gave 14 as dark solid (554 mg, 89%), m.p. 194-196° C. $\delta_H$ (500 MHz, CDCl₃): 8.03 (d, J=7.4, 4H), 7.85 (d, J=8.3, 4H), 7.40 (t, J=7.4, 4H), 7.34 (t, J=7.1, 2H), 7.09 (s, 2H), 7.03 (d, J=8.3, 4H), 4.72 (s, 4H), 3.85 (s, 6H). $\delta_C$ (100 MHz, CDCl₃): 169.0, 159.3, 154.1, 149.4, 142.3, 133.8, 129.0, 128.20, 128.15, 127.9, 126.1, 115.3, 114.4, 65.3, 52.4. HRMS (ESI) calcd for $C_{38}H_{32}N_3O_6$ [M+H⁺]⁺: 626.2291. found 626.2304. IR (KBr disc) cm⁻¹: 1767, 3055 cm⁻¹.

Compound 15:

Compound 14 (275 mg, 0.44 mmol) was dissolved in dry CH₂Cl₂ (80 mL) DIEA was added (0.8 mL, 4.6 mmol) followed by BF₃.OEt₂ (1 mL, 8.12 mmol) and the reaction mixture was stirred at r.t. for 24 hr under N₂ atmosphere. The reaction mixture was washed twice with water, the organic phase separated, dried and evaporated. The residue was purified by silica gel column chromatography (eluent, CH₂Cl₂/AcOEt 95:5) affording 15 as red solid (215 mg, 73%), m.p. 206-208° C. $\delta_H$ (500 MHz, CDCl₃): 8.04-8.09 (m, 8H), 7.54-7.36 (m, 6H), 7.07-6.94 (m, 6H), 4.71 (s, 4H), 3.84 (s, 6H). $\delta_C$ (100 MHz, CDCl₃): 168.9, 160.0, 158.1, 145.4, 143.5, 132.4, 131.7, 129.33, 129.30, 128.6, 125.2, 118.7, 114.9, 65.2, 52.4. HRMS (ESI) calcd for $C_{38}H_{31}BN_3O_6F_2$ [M+H⁺]⁺: 674.2274. found 674.2277. IR (KBr disc): 1602, 1732, 1763 cm⁻¹.

Compound 16:

Compound 15 (248 mg, 400 mmol) and potassium trimethylsilanolate (600 mg, 4.8 mol) were stirred in dry THF for 3 h. 2N HCl (12.5 mL) was added, THF was removed under the reduced pressure and the resulting mixture was extracted with 25% isopropanol in CH₂Cl₂. Organic phase was washed with water, dried and evaporated. Subsequent preparative RP-HPLC (C-18; acetonitrile-water, 90:10; retention time: 8 min) afforded 16 as dark powder (86 mg, 34%), m. p. 214-216° C. $\delta_H$ (500 mHz, acetone-$d_6$): 8.04-8.09 (m, 8H), 7.54-7.36 (m, 6H), 7.07-6.94 (m, 6H), 4.71 (s, 4H), 3.84 (s, 6H). ¹³C NMR (100 mHz, acetone-$d_6$): 168.9, 160.71, 158.2, 145.2, 143.0, 132.4, 131.8, 129.4, 129.3, 128.6, 124.5, 119.4, 114.8, 64.5. HRMS (ESI) calcd for $C_{36}H_{25}BN_3O_6F_2$ [M−H⁺]⁺: 644.1804. found 644.1824. IR (KBr disc): 1023, 1035, 1266, 1472, 1503, 1604 cm⁻¹.

Compound 17:

Compound 16 (168 mg, 320 mmol), propane-1,3-sultone (97 mg, 800 mmol) and K₂CO₃ (110 mg, 800 mmol) were heated under reflux in acetone (60 mL) for 6 hr, under a N₂ atmosphere. The resulting precipitate was filtered, washed with acetone and cold methanol. Preparative RP-HPLC (C-18; acetonitrile-water, 60:40; retention time: 3 min) afforded 16 (102 mg, 41%) as a green solid m.p.>300° C. For NMR analysis the compound was transformed into tetrabutylammonium salt by extraction of aqueous solution of 17 with CHCl₃ in presence of tetrabutylammonium chloride. The organic phase was washed with water twice, dried and evaporated. $\delta_H$ of 17.(NBu₄)₂ (500 MHz, CDCl₃): 8.11-8.00 (m, 8H), 7.51-7.35 (m, 6H), 7.04 (s, 2H), 6.99 (d, J=9.0, 4H), 4.25 (t, J=6.4, 4H), 3.32-3.17 (m, 16H), 2.98 (t, J=7.3, 4H), 2.42-2.28 (m, 4H), 1.61 (dt, J=12.0, 7.8, 16H), 1.51-1.31 (m, 16H), 0.98 (t, J=7.3, 24H). $\delta_C$ (100 MHz, CDCl₃): 161.7, 158.0, 145.2, 142.9, 132.5, 131.6, 129.21, 129.18, 128.5, 123.7, 118.6, 114.8, 67.4, 58.7, 48.2, 25.6, 23.9, 19.7, 13.7. HRMS (ESI) calcd for $C_{38}H_{33}BN_3O_8F_2S_2$ [–H⁺]⁻: 772.1770. found 772.1757. IR (KBr disc) cm⁻¹: 1468, 1505, 1603 cm⁻¹.

The synthetic approach adopted for the bis-cationic derivative is outlined in Scheme 5.

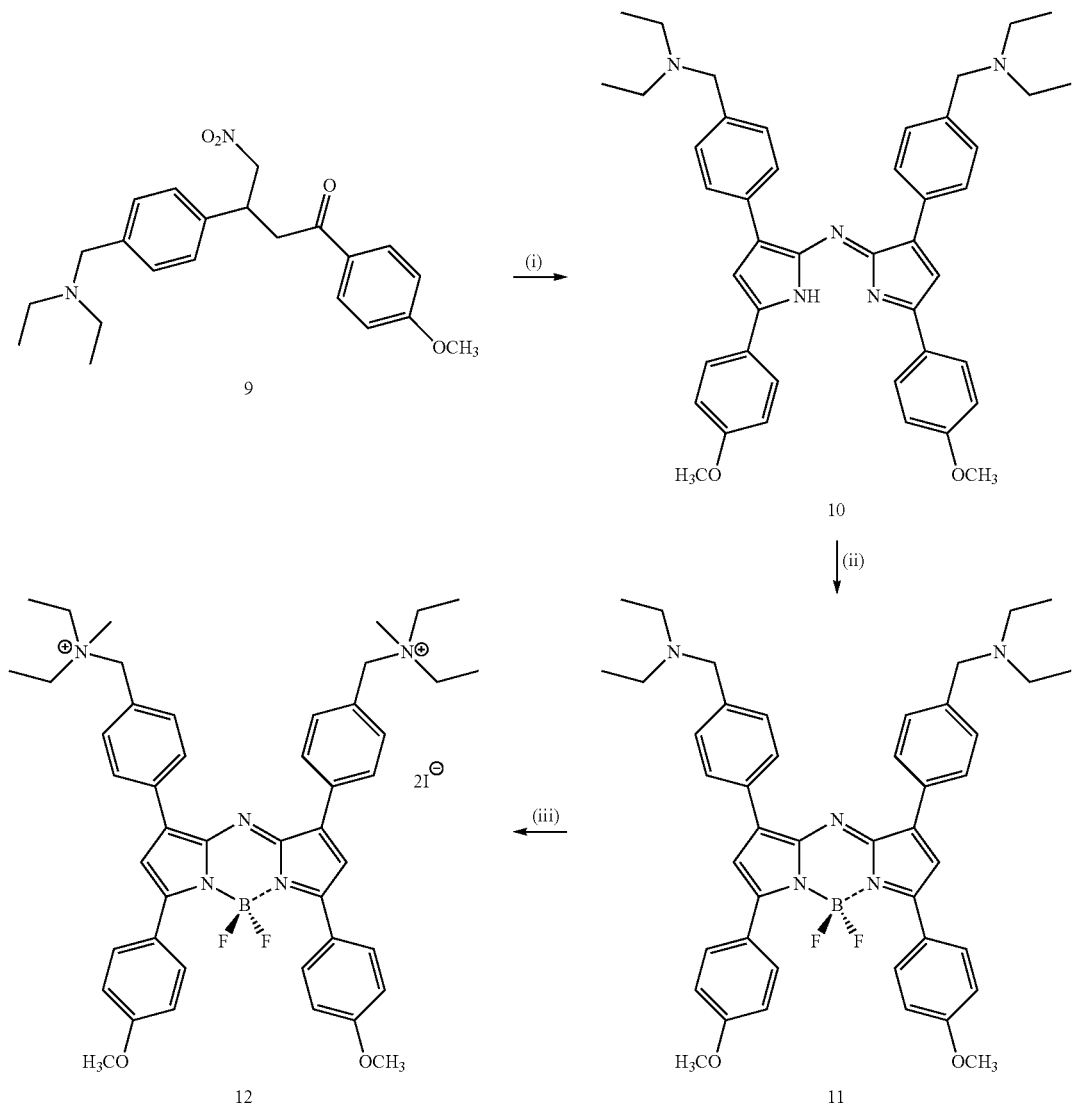

Scheme 5. Synthesis of bis-cationic substituted derivative.

Reagents and conditions: (i) NH₄OAc, EtOH, reflux, 48 hr, 36%. (ii) BF₃·OEt₂, DIEA, CH₂Cl₂, rt, 24 hr, 72%. (iii) MeI, CH₂Cl₂, rt, 24 hr, 80%.

Heating of the 1,3-diaryl-4-nitrobutan-1-one 18 with ammonium acetate gave the azadipyrromethene 19, and subsequent BF₂ chelation under standard conditions generated 20 in a 72% yield. Reaction of 20 with methyliodide at room temperature in dichloromethane proved an effective means to ensure complete alkylation with purified 21 obtained following recrystallisation from CH₂Cl₂/diethylether.

Further details of the products 19, 20 and 21 and synthesis thereof are provided below Compound 19:

3-(4-Diethylaminomethylphenyl)-1-(4-methoxyphenyl)-4-nitrobutan-1-one 18 (7.88 g, 20.5 mmol), ammonium acetate (55.22 g, 0.72 mol) and ethanol (200 mL) were heated under reflux for 48 hr. The reaction was allowed to cool to room temperature, the solvent was removed and the residue partitioned between CH₂Cl₂ (200 mL) and H₂O (150 mL).

The aqueous layer was basified with 1 M NaOH and extracted with CH$_2$Cl$_2$ (3×100 mL). The organic fractions were combined and the solvent evaporated. Column chromatography on alumina with CH$_2$Cl$_2$/ethyl acetate (7:1) as eluent gave 19 as a red metallic solid (2.50 g, 36%), m.p. 172-173° C. $\delta_H$ (300 MHz, CDCl$_3$): 8.01 (d, J=8.2 Hz, 4H), 7.87 (d, J=8.8 Hz, 4H), 7.38 (d, J=8.2 Hz, 4H), 7.10 (s, 2H), 7.03 (d, J=8.8 Hz, 4H), 3.90 (s, 6H), 3.64 (s, 4H), 2.58 (q, J=7.2 Hz, 8H), 1.10 (t, J=7.2 Hz, 12H), NH not observed. $\delta_C$ (100 MHz, 50 CDCl$_3$): 161.4, 154.2, 149.6, 142.3, 139.8, 132.7, 129.2, 129.0, 128.3, 125.3, 114.8, 114.1, 57.7, 55.7, 47.0, 12.1. ES-MS: m/z 680 [M+H$^+$]$^+$. HRMS (ESI) calcd for C$_{44}$H$_{50}$N$_5$O$_2$ [M+H$^+$]$^+$: 680.3965. found 680.3967. IR (KBr disk): 3455, 3421, 1606 cm$^{-1}$.

Compound 20:

Compound 19 (0.45 g, 0.66 mmol) was dissolved in dry CH$_2$Cl$_2$ (80 mL) under N$_2$, treated with diisopropylethylamine (0.86 g, 6.6 mmol) and BF$_3$.Et$_2$O (1.32 g, 9.3 mmol) and stirred at room temperature for 24 hr. The resultant green solution was washed with water (3×50 mL), dried over Na$_2$SO$_4$ and evaporated to dryness. The crude material was recrystallised from toluene or was columned on alumina eluting with CH$_2$Cl$_2$/ethylacetate (8:1) to give 20 as a metallic red solid (0.35 g, 72%), m.p. 198-200° C. $\delta_H$ (500 MHz CDCl$_3$): 8.09-8.11 (m, 4H), 8.05 (d, J=8.1 Hz, 4H), 7.46 (d, J=8.1 Hz, 4H), 7.01-7.04 (m, 6H), 3.90 (s, 6H), 3.68 (s, 4H), 2.61 (q, J=7.2 Hz, 8H), 1.12 (t, J=7.2 Hz, 12H). $\delta_C$ (125 MHz CDCl$_3$): 162.1, 158.3, 145.6, 143.4, 141.6, 131.8, 131.3, 129.3, 129.3, 124.5, 118.5, 114.5, 57.6, 55.7, 47.1, 12.0. ESI-MS: m/z 728 [M+H]$^+$. HRMS calcd for C$_{44}$H$_{49}$BF$_2$N$_5$O$_2$ [M+H]$^+$: 728.3947. found: 728.3936. IR (KBr disk): 3419, 2966, 1602 cm$^{-1}$. $\lambda_{max}$ abs (CHCl$_3$): 691 nm ($\epsilon$=76,000 Lmol$^{-1}$ cm$^{-1}$).

Compound 21:

Compound 20 (300 mg, 0.41 mmol) was dissolved in dry CH$_2$Cl$_2$ (60 mL), treated with methyliodide (260 μL, 4.1 mmol) and stirred under N$_2$ for 24 hr at rt. The solvent was removed under reduced pressure and recrystallisation from CH$_2$Cl$_2$/Et$_2$O (8:1) gave the product 21 (330 mg, 80%) as a dark green solid mp>300° C. $\delta_H$ (500 MHz, DMSO-d$_6$): 8.30 (d, J=8.0 Hz, 4H), 8.20 (d, J=9.0 Hz, 4H), 7.77 (d, J=8.0 Hz, 4H), 7.74 (s, 2H), 7.17 (d, J=9.0 Hz, 4H), 4.62 (s, 4H), 3.90 (s, 6H), 3.43-3.39 (m, 4H), 3.31-3.26 (m, 4H), 2.95 (s, 6H), 1.35 (t, J=7.0 Hz, 12H). $\delta_C$ (125 MHz, DMSO-d$_6$): 162.7, 158.1, 145.1, 141.2, 133.8, 132.4, 129.7, 129.4, 123.4, 121.0, 115.0, 63.5, 56.1, 55.8, 46.6, 8.30. IR (KBr disc) cm$^{-1}$: 3434, 1603. ES-MS: m/z 884.7 [M-I$^-$]$^+$. HRMS (ESI) calcd for C$_{46}$H$_{54}$BF$_2$N$_5$O$_2$ [M-I$^-$]$^+$ 884.3383. found 884.3381.

Spectroscopic properties of 16, 17 and 21 in organic solvents correspond very closely to those previously reported for this class of compound. For example, in chloroform the absorption maxima range from 681 nm for 16, 694 nm for 17 to 702 nm for 12 with very minor shifts from these values recorded in methanol (Table 5, FIGS. 21 and 22).

TABLE 5

Spectroscopic Characteristics of 16, 17 and 21.

| | | $\lambda_{max}$ abs. [nm][a] | | | | $\lambda_{max}$ emiss. [nm][b,c,d] | | | | |
|---|---|---|---|---|---|---|---|---|---|---|
| Entry | Comp. | CHCl$_3$ | MeOH | DMEM | PBS/BSA | CHCl$_3$ | MeOH | DMEM | PBS/BSA | $\Phi_f$[f] |
| 1 | 16 | 681 | 681 | 694 | 692 | 711 | 715 | 722 | 718 | 0.30 |
| 2 | 17 | 694[e] | 687 | 694 | 692 | 726 | 716 | 728 | 718 | 0.31 |
| 3 | 21 | 702 | 702 | 709 | 706 | 735 | 732 | 737 | 730 | 0.22 |

[a] Conc. 1 × 10$^{-6}$ M.
[b] Conc 5 × 10$^{-7}$ M.
[c] Excitation at 640 nm.
[d] Slit widths 5 nm.
[e] As tetra-butylammonium salt.
[f] CHCl$_3$.

Figure 21:
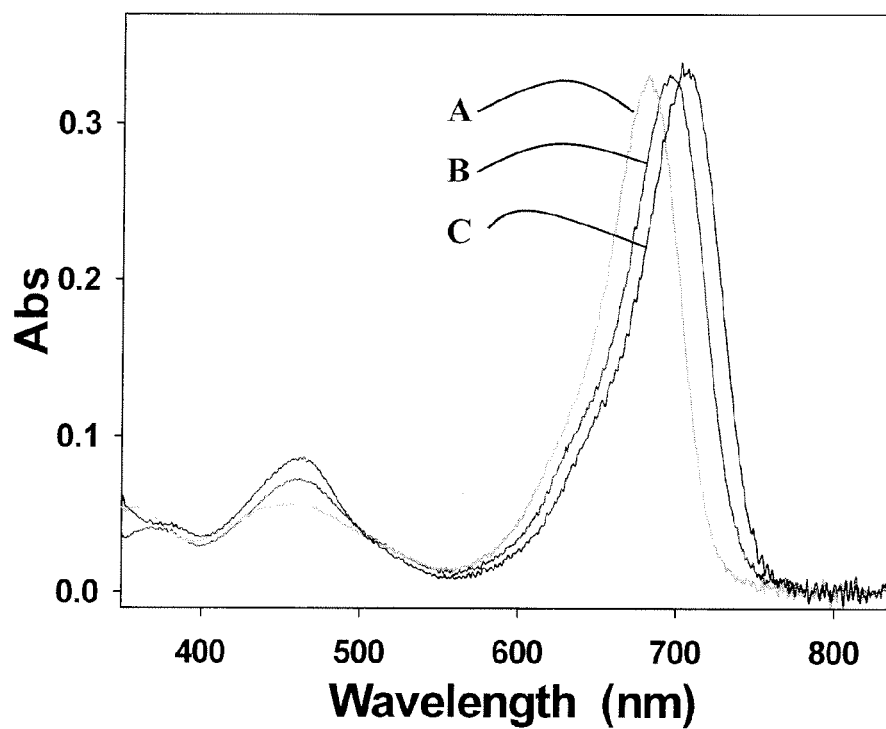
FIG. 21. Normalised absorption (left) and emission (right) spectra of 16 (A), 17 (B), and 21 (C) in $CHCl_3$.
Figure 21:
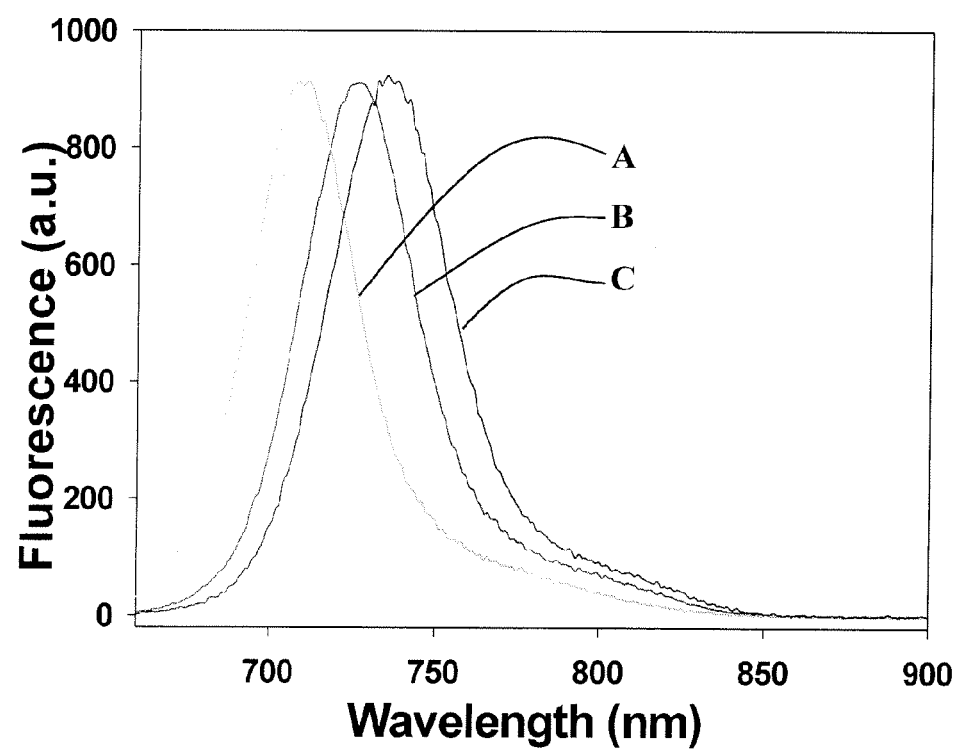
Figure 22:
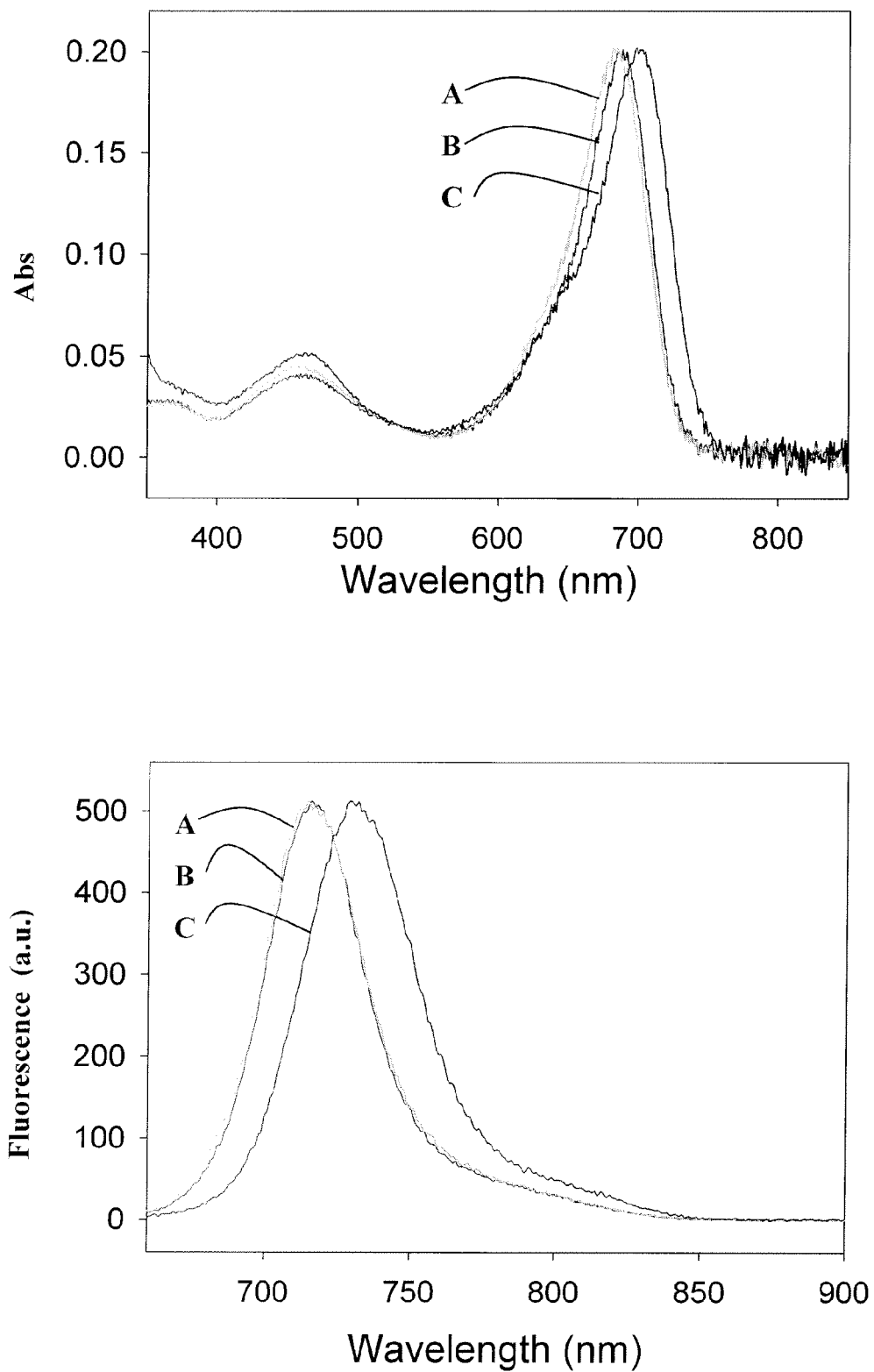
FIG. 22. The absorption (left) and fluorescence (right) of 16 (A), 17 (B), and 21 (C) in methanol. Fluorescence spectra were taken after excitation at 640 nm.
Figure 23:
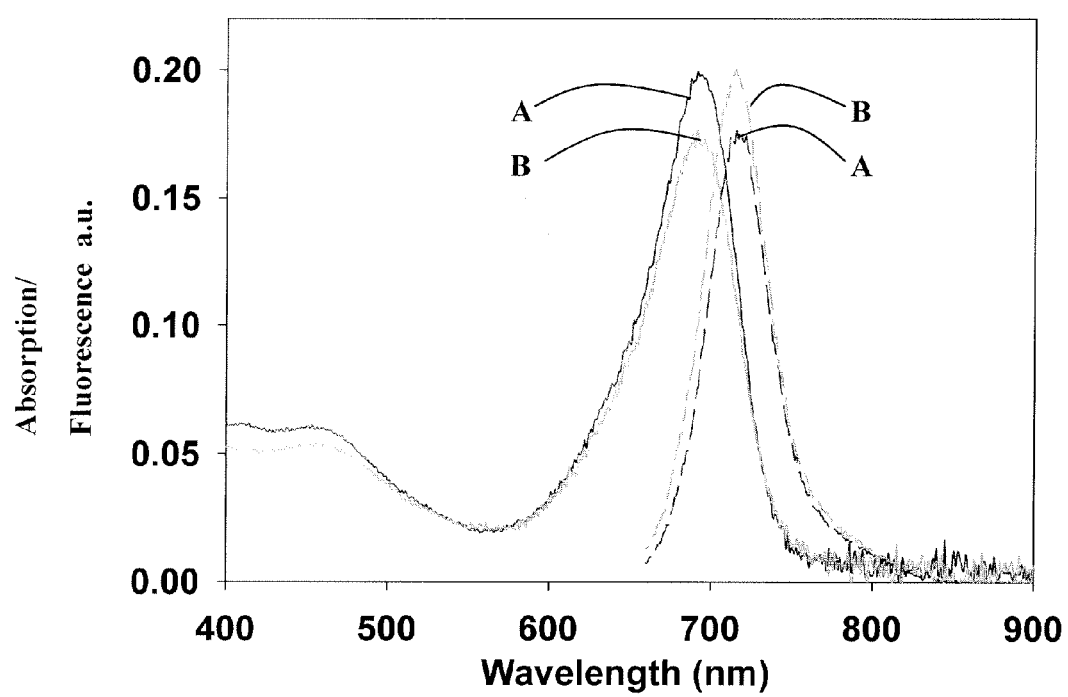
FIG. 23. The stability of 16 in PBS (pH=7.0) containing 3% of BSA. Spectra were taken after 24 hr (A) and 48 hr (B) exposure to the sun light. Solid and dashed lines represent relative absorption and fluorescence respectively.
Figure 24:
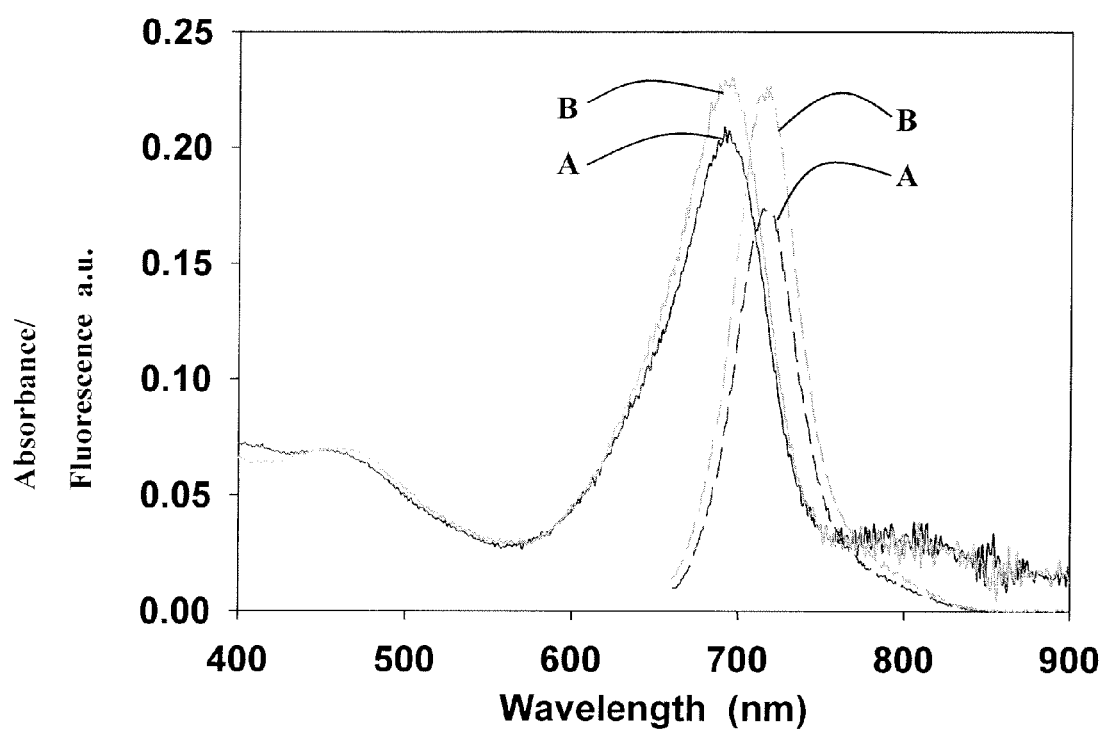
FIG. 24. The stability of 17 in PBS (pH=7.0) containing 3% of BSA. Spectra were taken after 24 hr (A) and 48 hr (B) exposure to the sun light. Solid and dashed lines represent relative absorption and fluorescence respectively.
Figure 25:
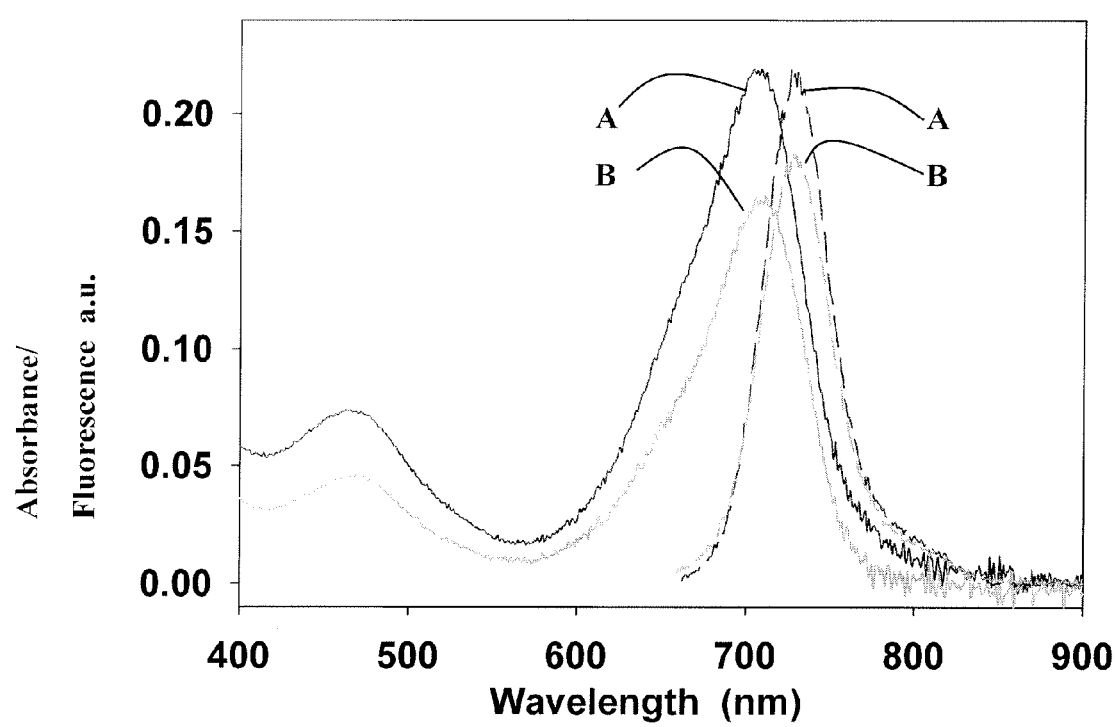
FIG. 25. The stability of 21 in PBS (pH=7.0) containing 3% of BSA. Spectra were taken after 24 hr (A) and 48 hr (B) exposure to the sun light. Solid and dashed lines represent relative absorption and fluorescence respectively.

Each fluorophore exhibited a strong fluorescence emission with quantum yields between Φ=0.22-0.31 and maxima at 711, 726 and 735 nm for 16, 17 and 21 respectively (Table 5, FIGS. 21 and 22). Comparison of the three fluorophores showed only minor bathochromic shifts for the derivatives 16 and 17 when compared to 21 (Table 5).

It will be appreciated that when 17 is used, the COO$^-$ moieties may be used as conjugation groups, for attaching to small molecules, or as water-solubilizing groups, or one as a conjugation group and the other as a water-solubilizing group, depending on the preferred use.

Figure 26:
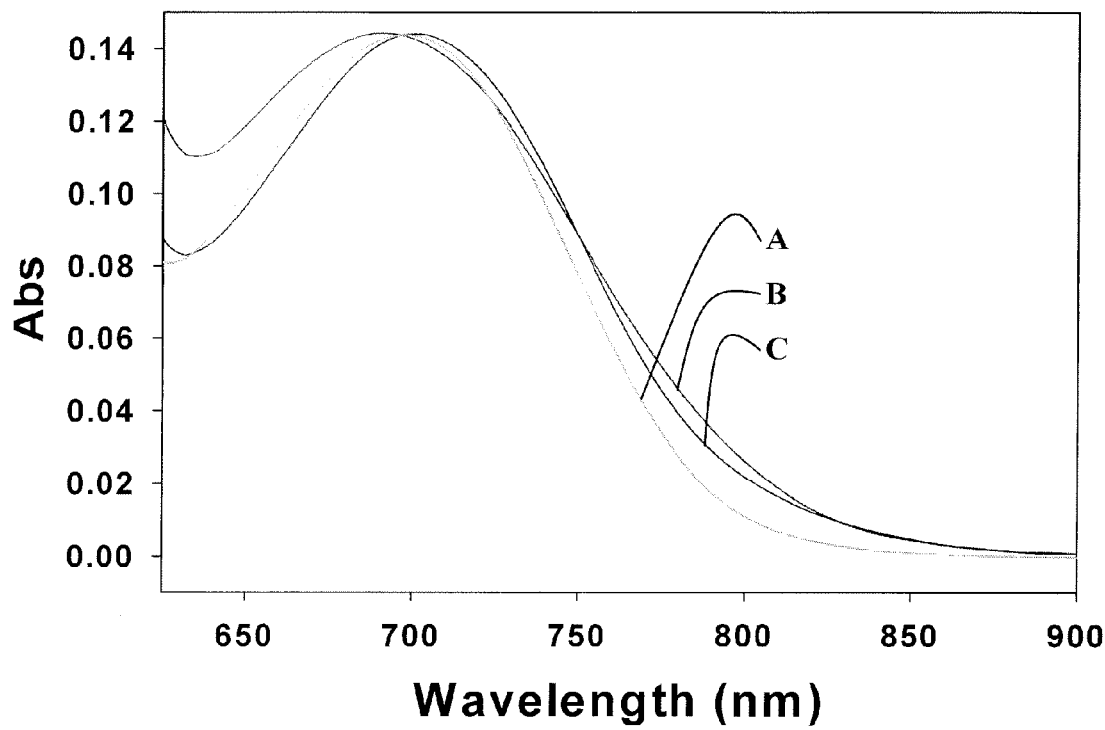
FIG. 26. Normalised absorption (left) and emission (right) spectra of 16 (A), 17 (B), and 21 (C) in DMEM. Absorption spectrum below 600 nm is not shown due to masking by phenol red dye contained in DMEM.
Figure 26:
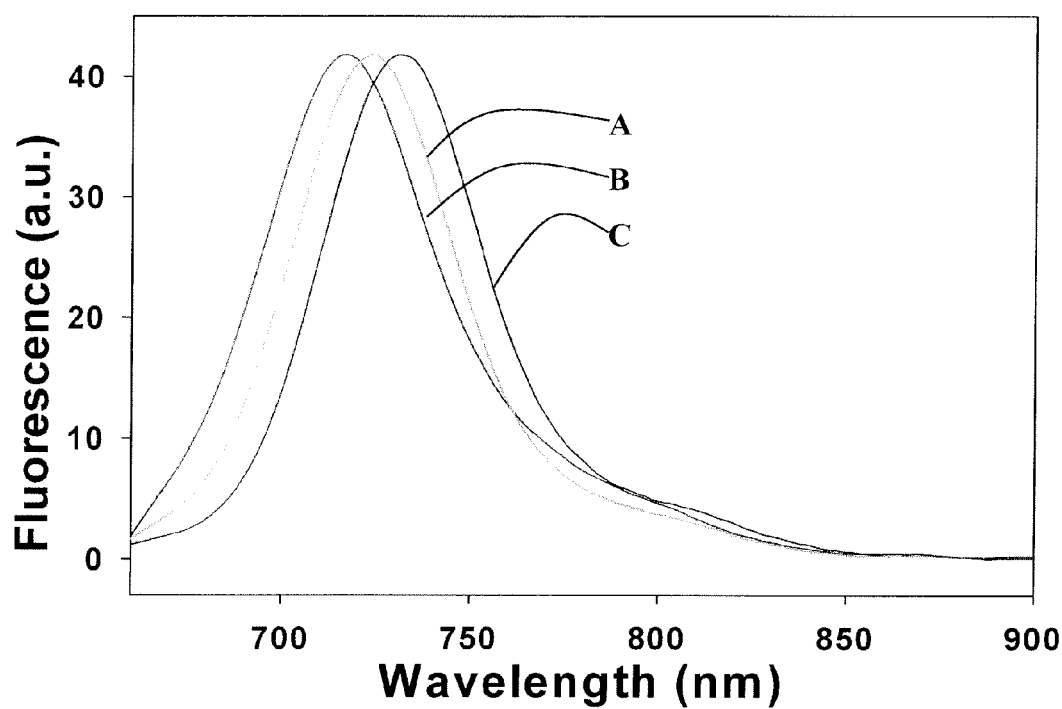

As a representative biological aqueous solution, spectra of 16, 17, and 21 were taken in Dulbecco's modified Eagle's medium (DMEM) which is a commonly used medium for cellular manipulations. Each fluorophore showed small bathochromic shift in their λ max of emission (5-12 nm) when compared to organic solvents, with emission bands extending from 700 to 800 nm (FIG. 26).

These spectroscopic properties correlate perfectly to the optical requirements of commercially available confocal laser scanning microscopy (CLSM) instruments and small animal optical imaging instruments. Cellular uptake of DMEM solutions of 16 and 17 were utilised to illustrate their potential for in vitro imaging. Compounds 16 and 17 were incubated with MDA-MB-231 cells for 1 hour at 5 μM concentration and the excess dye was removed by washing with PBS before visualisation.

Further details of the procedure are provided below.

MDA-MB-231 Cell and Bacteria Incubation Conditions

MDA-MB-231 cells were seeded into a 8 well chambered microscopy slide and they were grown overnight in DMEM media at 37° C. in the presence of 5% CO$_2$. The media was then removed and 16 and 17 (5 μM) was added, followed by an incubation period of 1 hour in the dark. Cells were then washed with PBS to remove excess compound. Prior to visualization, cells were fixed in 3.7% formaldehyde solution, co-stained with DAPI and a coverslip was mounted onto the microscopy slide. In a similar way, E. coli cells were incubated with 21 (4 μM) in the dark for 10 minutes. The bacterial cells were washed with PBS and An aliquot of this solution was suspended onto a microscopy slide and allowed to dry. Before imaging, a coverslip was mounted onto the microscopy slide. Images were obtained using an LSM510 META confocal laser scanning microscope equipped with 63× numerical aperture 1.4 objective. DAPI was excited at 364 nm and detected with a band-pass filter 385-470 nm, whilst 16, 17 and 21 were excited at 633 nm and their fluorescence was detected through a 650 nm long-pass filter.

Figure 27:
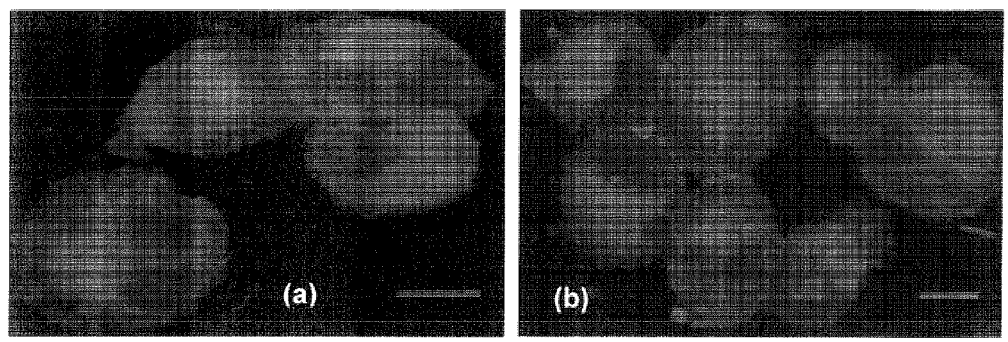
FIG. 27. CLSM images of MDA-MB-231 cells after 1 hr incubation with 5 μM solution of (a) 16 and (b) 17. Scale bars, 10 μm.
Figure 31:
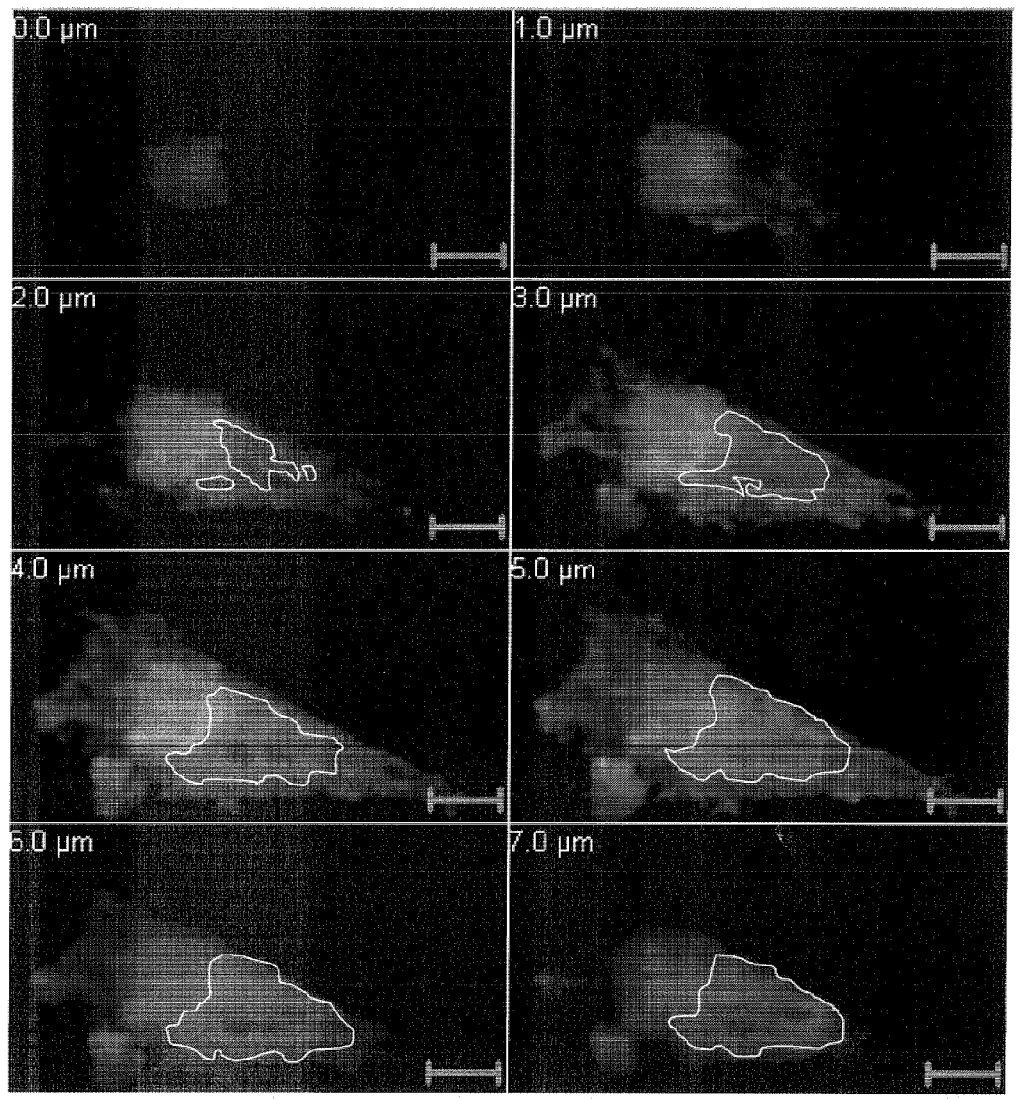
FIG. 31. CLSM Z-Stack Analysis of 17 in MDA cells and nuclear co-staining with DAPI (blue colour). scale bar 5 μm.
Figure 32:
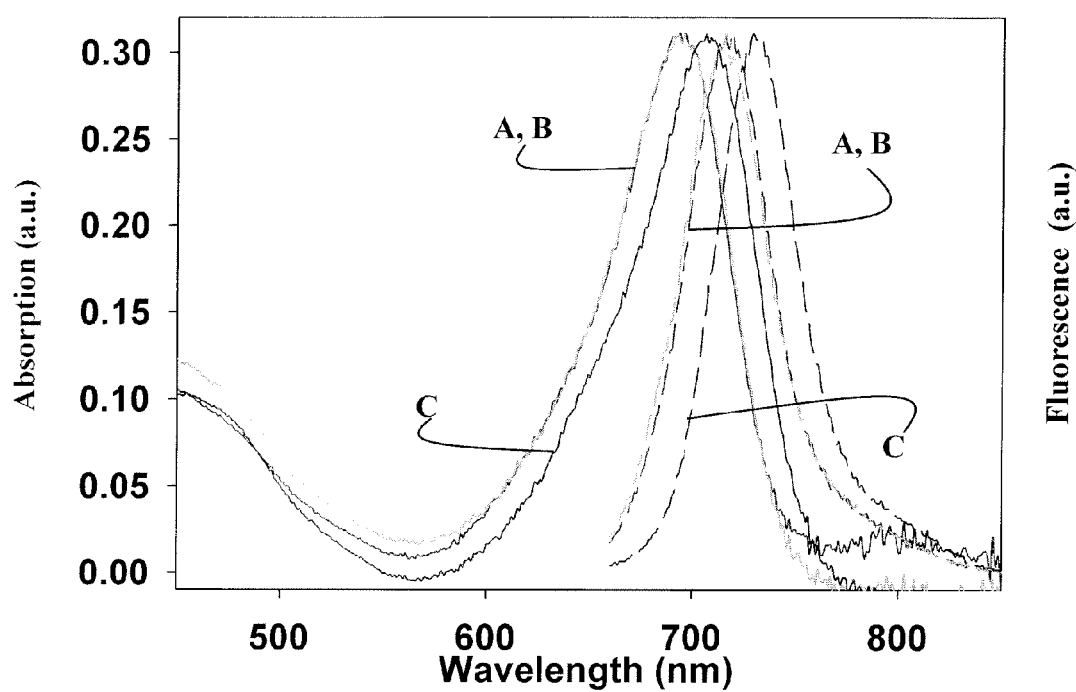
FIG. 32. Absorbance (solid line) and fluorescence (dashed line) spectra of 16 (A), 17 (B) and 21 (C) in PBS/BSA solutions.
Figure 33:
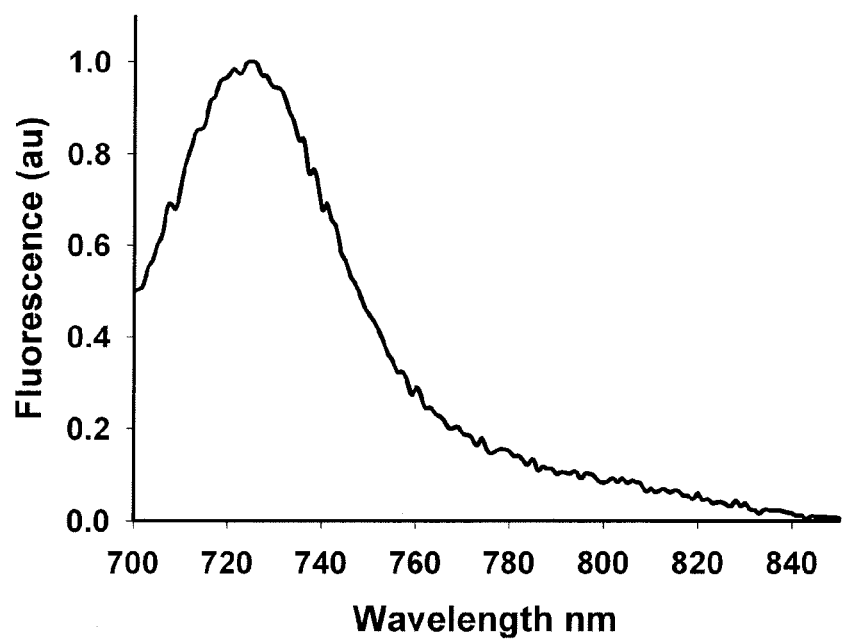
FIG. 33. Emission Spectrum of 200 nm functionalized beads in $H_2O$, Nano-bead fluorescence λ max of 727 nm.
Figure 34:
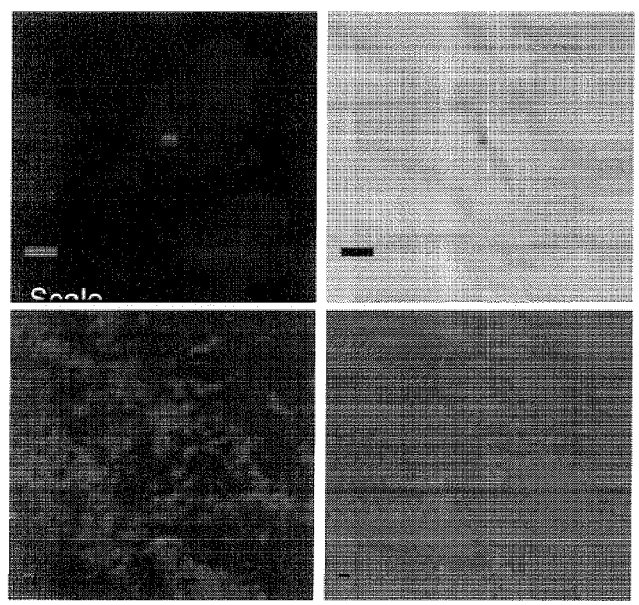
FIG. 34. Confocal Image of 200 nm functionalized beads. Image acquired using a 633 nm excitation and a 650 nm long-pass collection filter. Scale Bar, 1 μm.
Figure 35:
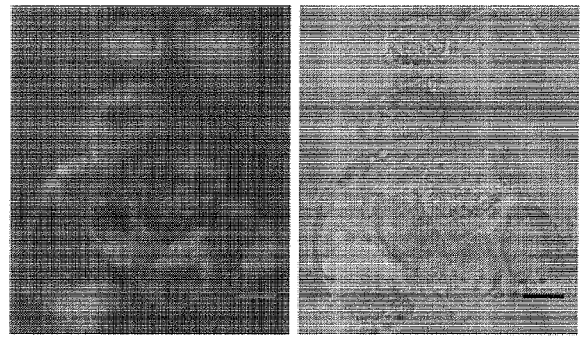
FIG. 35. Confocal Image of MDA cells with internalised 200 nm functionalized beads. Image acquired using a 633 nm excitation and a 650 nm long-pass collection filter.
Figure 36:
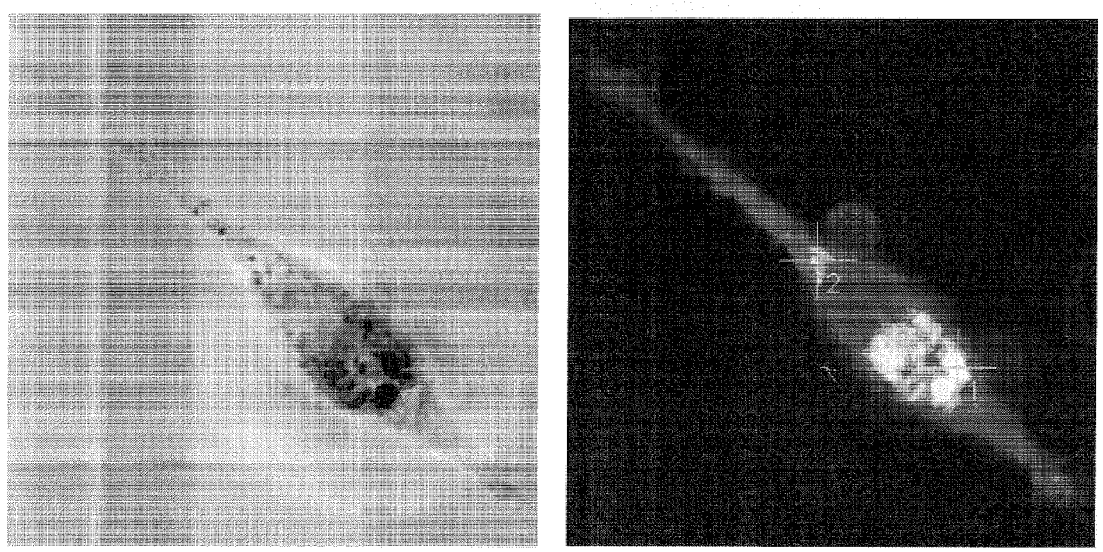
FIG. 36. Confocal Image of a single MDA cell with internalised 200 nm functionalized beads. Image acquired using a 633 nm excitation and a 650 nm long-pass collection filter.

The obtained images showed that 16 and 17 were efficiently taken up by cells, after a relatively short incubation period, and were readily imaged by CSLM (FIGS. 27a, 27b). 3-D reconstruction of cellular distribution determined by the combination of 10 focal plane sections and nuclear co-staining with 4,6-diamidino-2-phenylindole (DAPI) showed that the subcellular localisation of 16 and 17 were primarily to the cytoplasm (FIG. 31).

Figure 28:
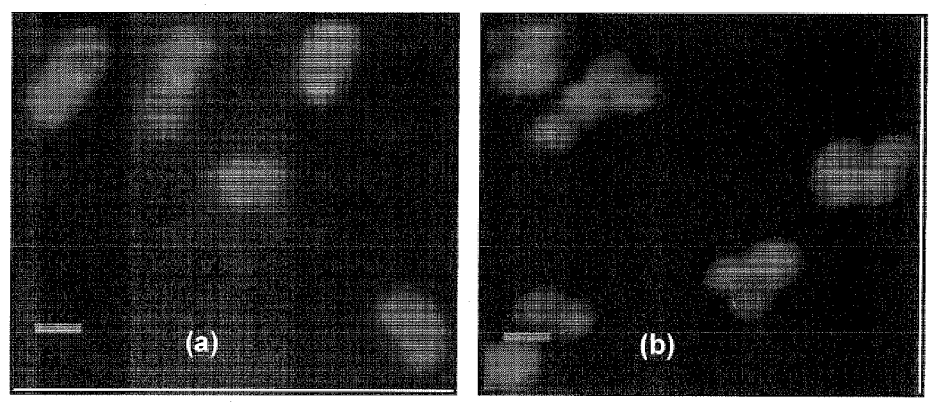
FIG. 28. CLSM images of (a) E. coli and (b) S. aureus cells after 10 min. incubation with 4 μM solution of 21. Scale bars, 1 μm.
Figure 29:
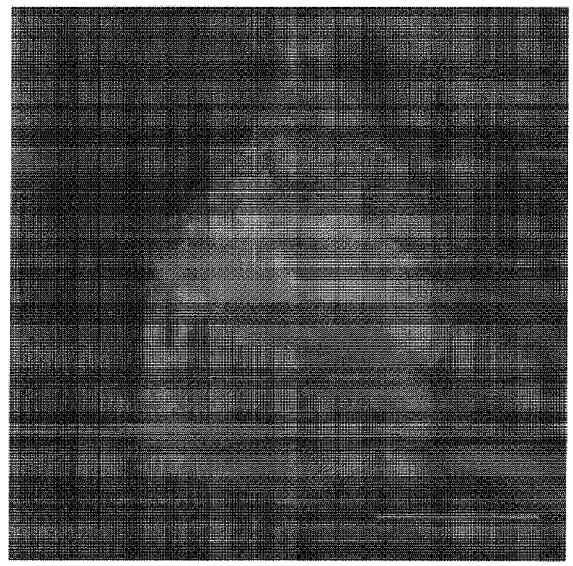
FIG. 29. Individual MDA-MB-231 cell following incubation with 16. Scale bar 10 μm.
Figure 30:
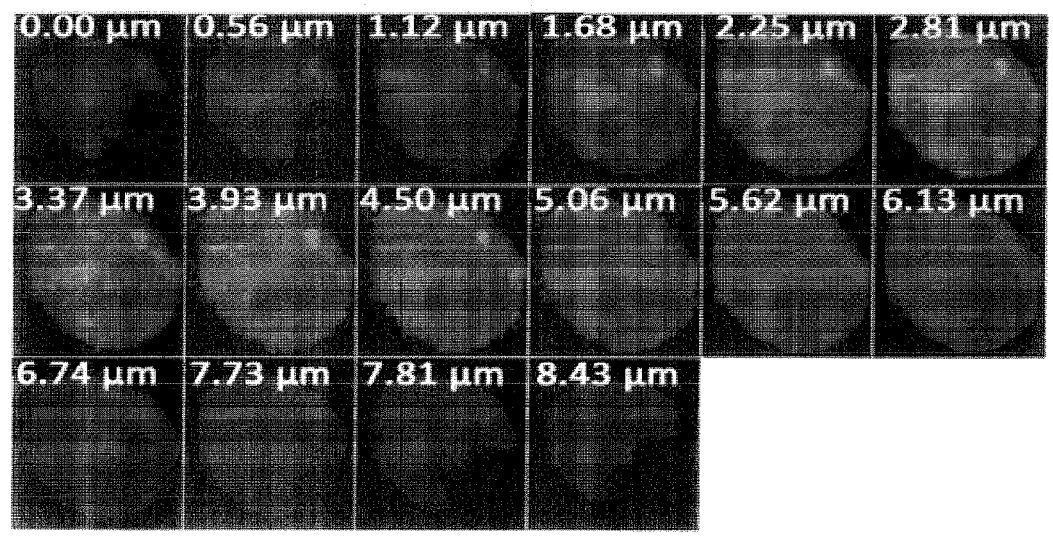
FIG. 30. CLSM Z-Stack Analysis of 16 in MDA-MB-231 cells.

It was envisaged that the bis-cationic nature of sensitizer 21 would be optimal for uptake into prokaryotic cells thereby broadening their utility. Incubation of aqueous solutions of 21 with both gram-positive (*Staphylococcus aureus*) or gram-negative (*Escherichia coli*) bacterial cells for only 10 minutes was sufficient for cellular uptake. Confocal imaging confirmed the binding of 21 to both gram-positive and negative bacterial cells (FIGS. 28a, 28b). Additional images are shown in FIGS. 29 and 30.

To establish the spectral characteristics of these fluorophores for potential in vivo imaging applications, their properties in the presence of serum proteins were examined. Serum albumin is the most abundant protein in blood plasma at a typical concentrations of ~50 g/L. As one of its principal functions is to act as a binding and carrier protein within the vasculature it would be expected that strong interactions between it and our fluorophores could occur. This is known for ICG and the spectroscopic effects of plasma on ICG have been thoroughly documented. As a preliminary examination to test if the spectral properties are adversely effected by such proteins their spectra in aqueous BSA (bovine serum albumin) solutions was recorded. Sharp absorbance and emission bands were observed in each case with emission maxima at 718 nm for 16 and 17 and 730 nm for 21 in a phosphate buffered saline (PBS) solution containing $4 \times 10^{-4}$ M BSA. These solutions remained stable for prolonged periods exposed to ambient light with less than 10% variance in absorbance and fluoresence intensity after 24 hours (FIGS. 23, 24, 25 and 32). Collectively these properties are positive indicators for use as in vivo NIR fluorophores.

In summary, anionic and cationic substituted $BF_2$-chelated tetraarylazadipyrromethene derivatives, bearing sulfonic acid, carboxylic acid or quaternary amine moieties have been synthesised. These fluorophores show excellent photophysical characteristics in both organic and aqueous solutions. Delivery to and confocal imaging within eukaryotic and prokaryotic cells can be readily achieved.

EXAMPLE 5

Fluorescent Nano-Beads

This example demonstrates the preparation of fluorescent particles, specifically fluorescent nano-beads of the order of 100 nm. It is proposed that these fluorescent particles can be used for a wide range of commercial applications including in vivo imaging and as calibrants for fluorescence based analytical instrumentation such as flow cytometry.

Synthesis of Activated Ester PL-Latex Super Carbonyl White 200 nm

A water suspension of PL-Latex Super Carbonyl white 200 nm (2 mL), available from Varian Inc, was centrifuged and the resulting solid was dried over night under reduced pressure. The solid (75 mg, 0.014 mmol) was dispersed in dry DMSO (1.5 ml) and treated with EDCI (27 mg, 0.14 mmol) and N-hydroxysuccinimide (16 mg, 0.14 mmol). The reaction was agitated at room temperature for 16 hours. The solution was then diluted with water (3 mL) and centrifuged. The solid obtained was washed and centrifuged three times with water/DMSO (3:1) and dried under high vacuum. The full conversion of the acids residue into activated esters was confirmed by comparing the IR of the PL-Latex Super Carbonyl white 200 nm (IR 1698.50, 1739.48 cm$^{-1}$) with the IR of the product obtained (IR 1602.50, 1640.65 cm$^{-1}$). The resultant activated ester bead 22 is shown in Scheme 7.

Synthesis of Azadipyrromethene $BF_2$ Chelated-PL-Latex 200 nm Beads

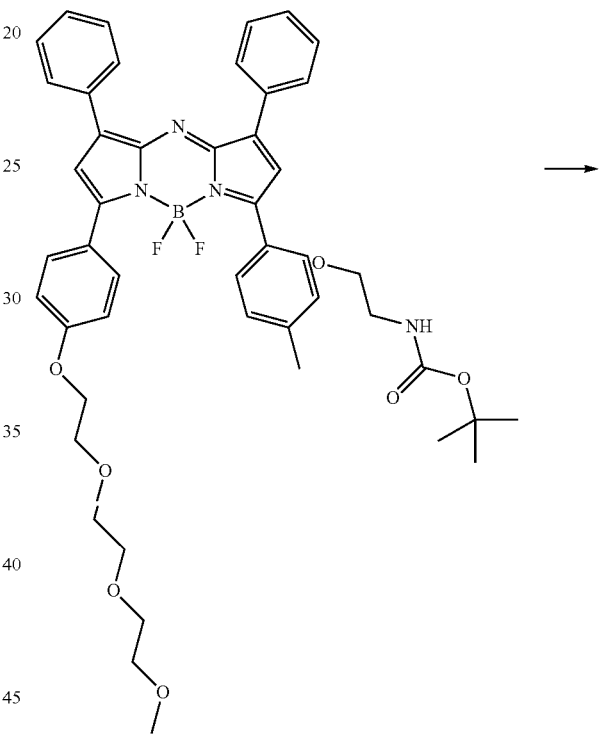

Scheme 6

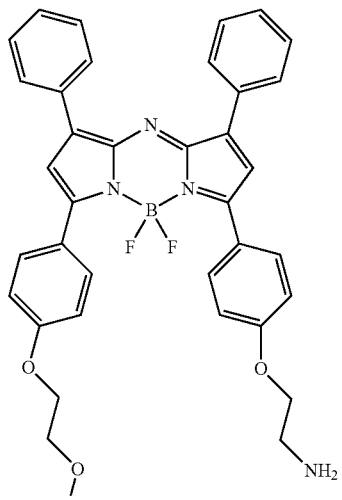

24

With reference to Scheme 6, the azadipyrromethene BF$_2$ chelated 23 (6 mg, 0.0075 mmol) was dissolved in DCM (10 mL) and treated with TFA (1 mL) at room temperature. The reaction was monitored by TLC and stopped when 23 was completely consumed. The reaction was extracted with NaHCO$_3$ (×2) and with water (×1) and dried over sodium sulfate yielding 24 in quantitative amounts.

Scheme 7

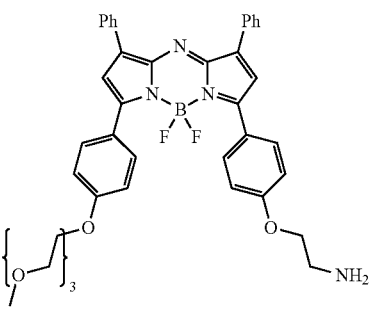

24

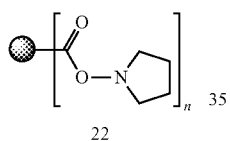

22

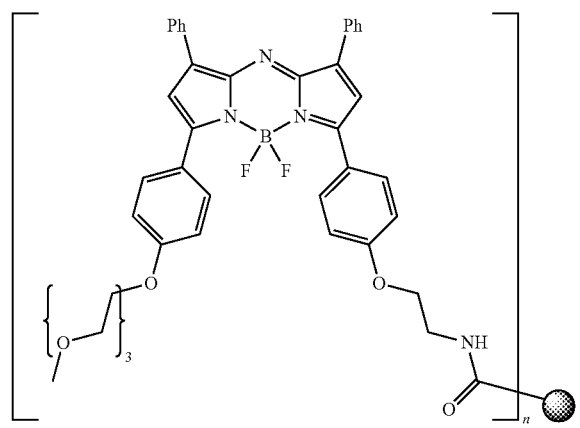

25

With reference to Scheme 7, a round bottom flask was charged with activated ester beads 22 (30 mg, 0.0058 mmol), azadipyrromethene BF$_2$ chelated 24 (5 mg, 0.0075 mmol) and dry THF (5 mL). The reaction was agitated at room temperature for 24 h. Deionized water (5 mL) was then added to the reaction mixture and the THF was removed under reduced pressure. The water solution was filtered under vacuum through a C18 filter to yield the purified functionalized beads 25.

Images obtained using the functionalized beads are shown in FIGS. 33-36.

EXAMPLE 6

Additional Compounds

In this example, the preparation of compounds according to the invention is described. All of the compounds described herein are produced downstream of compound 6, which is a compound of the formula (IB).

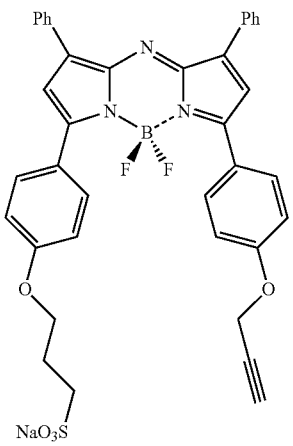

26

Compound 2 (75 mg, 125 mmol), propane-1,3-sultone (31 mg, 250 mmol) and K$_2$CO$_3$ (35 mg, 250 mmol) were heated under reflux in acetone (30 mL) for 6 hr, under a N$_2$ atmosphere. Solvent was removed and the residue was suspended in 2N HCl. Resulting solid was filtered, washed with water and dried affording product 26 (64 mg, 74%) as a dark green solid. For NMR analysis the compound was transformed into tetrabutylammonium salt by extraction of aqueous solution of acids with CHCl$_3$ in presence of tetrabutylammonium chloride. The organic phase was washed with water twice, dried and evaporated. $\delta_H$ of sulfonic acid.NBu$_4$ (500 MHz, CDCl$_3$): 8.10-8.04 (m, 8H), 7.48-7.38 (m, 6H), 7.10-7.06 (m, 3H), 7.02-6.99 (m, 3H), 4.77 (d, J=2.5 Hz, 2H), 4.25 (t, J=5 Hz, 2H), 3.32-3.25 (m, 8H), 3.01 (t, J=7.5 Hz, 2H), 2.58 (t, J=2.5 Hz, 1H), 2.40-2.32 (m, 2H), 1.68-1.60 (m, 8H), 1.48-1.40 (m, 8H), 1.00 (t, J=7.5 Hz, 12H). $\delta_C$ (100 MHz, CDCl$_3$): 162.0, 159.1, 145.7, 144.9, 143.6, 142.6, 132.6, 132.4, 131.7 (m), 131.4 (m), 129.3, 129.2, 129.1, 128.53, 128.52, 125.2, 123.4, 119.0 (m), 118.3 (m), 114.97, 114.91, 78.1, 76.1, 67.4, 58.8, 55.9, 48.2, 25.6, 25.0, 19.7, 13.6. HRMS (ESI) calcd for C$_{38}$H$_{29}$BN$_3$O$_5$F$_2$S [M−H$^+$]$^-$ 688.1889. found 688.1877.

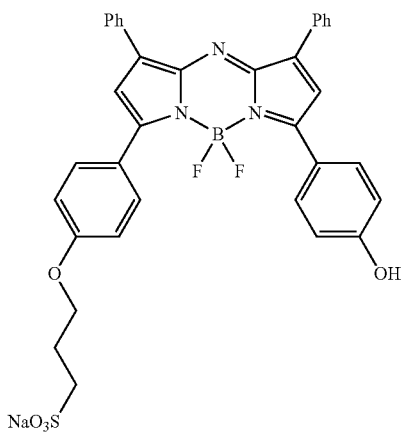

27

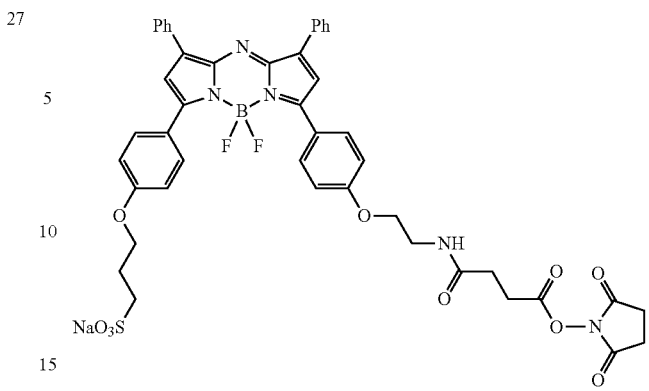

28

Compound 6 (168 mg, 320 mmol), propane-1,3-sultone (97 mg, 800 mmol) and K$_2$CO$_3$ (110 mg, 800 mmol) were heated under reflux in acetone (60 mL) for 6 hr, under a N$_2$ atmosphere. The resulting precipitate was filtered, washed with acetone and cold methanol. Preparative RP-HPLC (C-18; acetonitrile-water, 60:40) afforded bissulfonic acid (102 mg, 41%) and monosulfonic acid 27 (34 mg, 18%) as a green solids m.p.>300° C. For NMR analysis the compound was transformed into tetrabutylammonium salt by extraction of aqueous solution of acids with CHCl$_3$ in presence of tetrabutylammonium chloride. The organic phase was washed with water twice, dried and evaporated. $\delta_H$ of monosulfonic acid. (NBu$_4$)$_2$ (400 MHz, CDCl$_3$): 8.06-7.96 (m, 8H), 7.45-7.32 (m, 6H), 7.11-7.05 (m, 3H), 6.97-6.93 (m, 3H), 4.26 (t, J=6 Hz, 2H), 3.19-3.12 (m, 16H), 3.02 (t, J=6 Hz, 2H), 2.40-2.29 (m, 2H), 1.60-1.49 (m, 16H), 1.42-1.30 (m, 16H), 0.95 (t, J=8 Hz, 24H). $\delta_C$ (100 MHz, CDCl$_3$): 160.9, 159.3, 145.9, 144.1, 143.1, 142.5, 140.6, 132.9, 132.5 (m), 132.3, 131.2 (m), 129.2, 129.0, 128.6, 128.5, 128.4, 124.4, 120.9, 117.4, 117.2, 114.6, 67.1, 58.7, 48.1, 25.5, 23.9, 19.7, 13.6. HRMS (ESI) calcd for C$_{35}$H$_{27}$BN$_3$O$_5$F$_2$S [M–H$^+$]$^-$ 650.1733. found 650.1750.

$^1$H NMR (as Bu$_4$N salt): (400 MHz, CDCl$_3$): 0.95 (t, J=8 Hz, 24H), 1.42-1.30 (m, 16H), 1.60-1.49 (m, 16H), 2.48 (t, J=7 Hz, 2H), 2.61 (s, 4H), 2.97 (t, J=7 Hz, 2H), 3.44-3.51 (m, 2H), 3.52-3.75 (m, 6H), 4.01 (t, J=5 Hz, 2H), 4.13 (t, J=5 Hz, 2H), 6.87-6.97 (m, 6H), 7.31-7.39 (m, 6H), 7.95-8.00 (m, 8H). HRMS (ESI) calcd for C$_{49}$H$_{39}$BN$_5$O$_{10}$F$_2$S [M–Na$^+$]$^-$ 890.2479. found 890.2470.

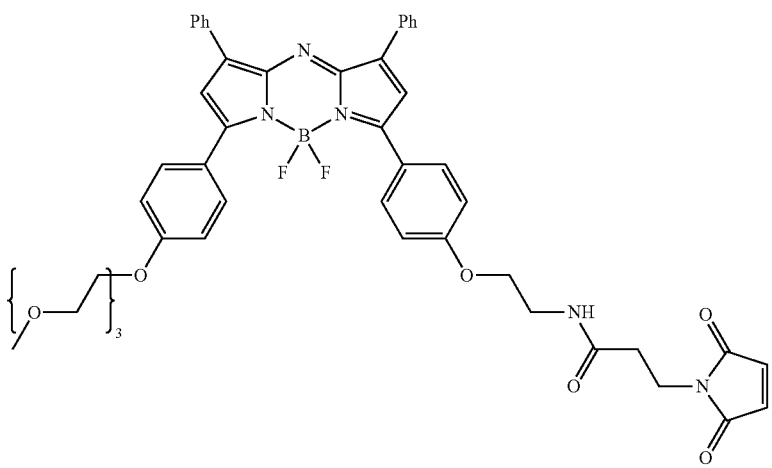

29

Boc-protected amine 9 (164 mg, 200 µmol) was dissolved in CH$_2$Cl$_2$ (10 mL), TFA (1 mL) was slowly added and the whole reaction mixture was stirred at r.t. for 2 h. Acid was neutralized by addition of sat. aqueous NaHCO$_3$, the resulting suspension was extracted with CH$_2$Cl$_2$ (2×30 mL), organic phases were washed with water and dried (Na$_2$SO$_4$). After evaporation, the resulting green residue was dissolved in dry THF (10 mL) and activated ester (succinimide-maleimide) (64 mg, 240 µmol) was added, followed by DIPEA (70 µL, 400 mmol). After stirring at r.t. for 3 h solvent was removed under reduced pressure and the residue was chromatographed (silica, EtOH/AcOEt, 4:96). Fractions containing desired product (R$_f$=0.35, silica, EtOH/AcOEt, 4:96) were collected and evaporated to afford 88 mg (51%) of product 29 as dark green crystals. M.p.=50-52° C. $^1$H NMR (500 MHz, CDCl$_3$) 2.54 (t, J=6.9 Hz, 2H, CH$_2$CO), 3.38 (s, 3H, OCH$_3$), 3.53-3.57 (m, 2H, ether), 3.61-3.70 (m, 6H, ether), 3.72-3.76 (m, 2H, ether), 3.83 (t, J=6.9 Hz, 2H, CH$_2$N (CO)$_2$), 3.87 (br t, J=4.8 Hz, 2H, ether), 4.05 (br t, J=4.8 Hz, 2H, ether), 4.20 (br t, J=4.8 Hz, 2H, ether), 6.12 (br m, 1H, NH), 6.54 (s, 2H, maleimide), 6.93-7.05 (m, 6H, Ar+pyrrole), 7.39-7.47 (m, 6H, Ar); 8.01-8.08 (m, 8H, Ar); $^{13}$C NMR (100 MHz, CDCl$_3$) δ 26.9, 29.7, 34.3, 34.9, 38.9, 59.0, 66.8, 67.6, 69.6, 70.56, 70.64, 70.9, 71.9, 114.6, 114.8, 118.38, 118.42, 118.77, 118.80, 124.1, 124.7, 128.5, 129.19, 129.23, 129.27, 131.53, 131.58, 131.64, 131.68, 132.4, 132.5, 134.1, 143.0, 143.4, 145.1, 145.5, 157.6, 158.5, 160.6, 161.3, 169.9, 170.5. ESI-HR obsd 892.3345 [M+Na$^+$], calcd exact mass 892.3305 (C$_{48}$H$_{46}$N$_5$O$_8$NaBF$_2$). (KBr disc): 1037, 1110, 1129, 1260, 1474, 1505, 1602, 1708, 2880, 2927. λ$_{abs}$ (CHCl$_3$) 689, nm. Fluorescence (CHCl$_3$): λ$_{max}$ (I)=717 nm (1.00).

NaHCO3 (2×50 mL), water (1×50 mL) and brine (1×50 dried with Na$_2$SO$_4$ and concentrated in vacuo. It was recrystallized with dichloromethane/cyclohexane 1/6. The resulting solid was collected by filtration as a black solid (270 mg, 96%).

$^1$H NMR (400 MHz, CDCl$_3$) δ: 7.95-8.01 (m, 10H), 7.72 (d, J=8.0, 1H), 7.30-7.36 (m, 6H), 7.16-7.22 (m, 8H), 6.82-6.95 (m, 8H), 6.22 (broad s, 1H, NH), 4.06 (t, J=5.0 Hz, 2H, CH$_2$), 3.97 (t, J=5.0 Hz, 2H, CH$_2$), 3.76 (t, J=5.0 Hz, 2H, CH$_2$), 3.63-3.70 (m, 7H, 2×CH$_2$+CH$_3$OCO), 3.55-3.60 (m,

30

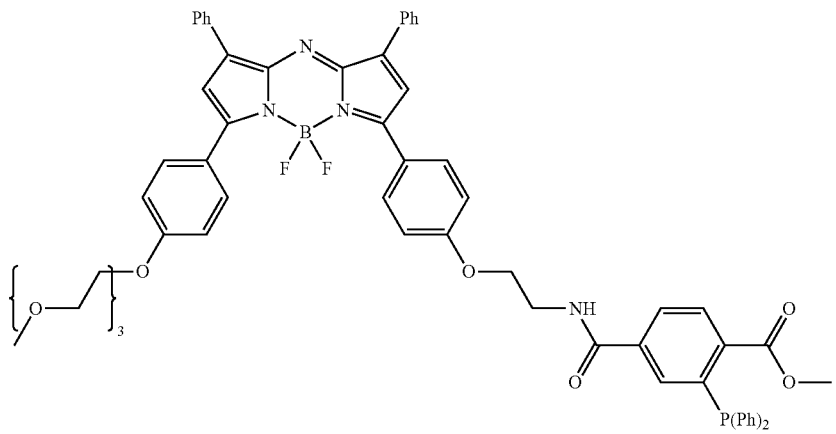

To a solution of 2-diphenilphosphonylterephthalic acid 1-methyl ester (96 mg, 0.26), DMAP (cat.) and EDO (60.5 mg, 0.32 mmol) in dry DCM (15 mL), azabodipy-amine (189 mg, 0.26 mmol) dissolved in dichloromethane mL) was added. The solution was degassed by freezing it in liquid nitrogen, after that the flask was put under high vacuum and the solution was allowed to thaw, finally the flask was back-filled with nitrogen. The mixture was stirred under nitrogen at room temperature overnight. Diethyl ether (100 mL) was added, and the organic layer was washed with 10% hydrochloric acid (2×50 mL), water (1×50 mL), saturated aqueous 4H, 2×CH$_2$), 3.44-3.47 (m, 2H, CH$_2$), 3.28 (s, 3H, CH$_3$OCH$_2$); $^{13}$C NMR (400 MHz, CDCl$_3$) δ: 165.5, 160.3, 159.4, 157.6, 156.5, 144.5, 144.1, 142.5, 141.9, 140.8, 140.5, 136.0, 135.9, 132.9, 132.7, 131.5, 131.3, 130.7, 130.6, 128.3, 128.2, 128.1, 127.7, 127.6, 127.5, 126.0, 123.9, 123.0, 113.8, 113.6, 70.9, 69.9, 69.6, 69.5, 68.5, 66.6, 58.0, 51.2, 38.4. $^{31}$P-NMR (162 MHz, CDCl$_3$) δ: −3.68 (P:). IR (KBr disk) cm$^{-1}$: 3055, 2929, 1720, 1668, 1604, 1476, 1265, 740. EI-MS: m/z 1065. HRMS Calcd for C$_{62}$H$_{57}$BF$_2$N$_4$O$_8$P [M+H]$^+$: 1065.3975. Found: 1065.3990. λ$_{max}$ (CHCl$_3$)=686 nm, extinction coefficient 75,500 M$^{-1}$ cm$^{-1}$.

31

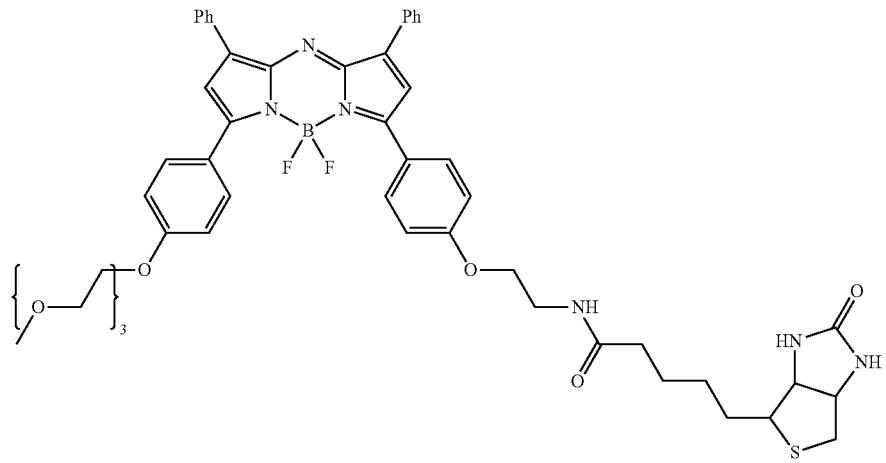

Boc-Amine 9 (10 mg, 12.2 μmol) was dissolved in CH$_2$Cl$_2$ (1 mL), TFA (0.15 mL) was slowly added and the whole reaction mixture was stirred at r.t. for 1 h. Acid was neutralized by addition of sat. aqueous NaHCO$_3$, the resulting suspension was extracted with CH$_2$Cl$_2$ (2×10 mL), organic phases were washed with water and dried (Na$_2$SO$_4$). After evaporation, the resulting green residue was dissolved in dry THF (1 mL) and DIPEA (10 μL) was added, followed by biotin-NHS (4 mg, 12.2 μmol). After stirring at r.t. for 10 min there was still some starting material left so more biotin-NHS (4 mg, 12.2 μmol) was added, leading to complete conversion after 10 min. Solvent was removed under reduced pressure and the residue was chromatographed (silica, MeOH/DCM, 5:95). Fractions containing desired product were collected and evaporated to afford 8 mg (69%) of product as dark green solid. $^1$H NMR (500 MHz, CDCl$_3$) δ 1.37-1.45 (m, 2H), 1.60-1.72 (m, 4H), 2.17-2.30 (m, 2H), 2.56-2.60 (m, 1H), 2.76-2.82 (m, 1H), 3.02-3.07 (m, 1H), 3.38 (s, 3H), 3.54-3.57 (m, 2H), 3.64-3.70 (m, 6H), 3.73-3.77 (m, 2H), 3.88 (t, J=5 Hz, 2H), 4.11 (br t, J=5 Hz, 2H), 4.15-4.19 (m, 1H), 4.21 (br t, J=5 Hz, 2H), 4.30-4.34 (m, 1H), 4.99 (br s, 1H), 5.95 (br s, 1H), 6.54 (br s, 1H), 6.97-7.04 (m, 6H), 7.38-7.47 (m, 6H), 8.02-8.07 (m, 8H). $^{13}$C NMR (400 MHz, CDCl$_3$) δ: 173.4, 161.3, 160.8, 158.4, 157.7, 145.4, 145.2, 143.4, 143.2, 132.45, 132.40, 131.6 (m), 129.3, 128.6, 124.6, 124.2, 118.8, 118.5, 114.9, 114.7, 72.0, 70.9, 70.7, 70.6, 69.6, 67.7, 67.2, 61.7, 60.1, 59.0, 55.4, 40.5, 38.9, 35.8, 28.0, 25.6, 25.4. ESI-HR obsd 945.4031 [M+H$^+$], calcd exact mass 945.3992 (C$_{51}$H$_{56}$N$_6$O$_7$SBF$_2$). (KBr disc): 1036, 1474, 1504, 1602, 1701.

An additional feature of fluorophore conjugated to nanoparticles is that the particles can be constructed such that the fluorescence intensity from the particle can be made responsive to micro-environmental changes. For example, in one embodiment the particles are virtually fluorescent-silent in aqueous media (due to self-aggregation on the particle surface and quenching by water molecules), including cell growth media. In contrast, following particle endocytosis and internalization within cells they become highly fluorescent (due to individual fluorophore molecules relaxing away from the surface of the particle and being shielded from the surrounding water molecules thereby giving rise to a large enhancement of their fluorescence intensity). This off-to-on fluorescence switching property facilitates real-time imaging of the cellular uptake processes, as conjugated particles and cells can be co-incubated together without a masking or interfering fluorescent signal from the extracellular particles.

Figure 37:
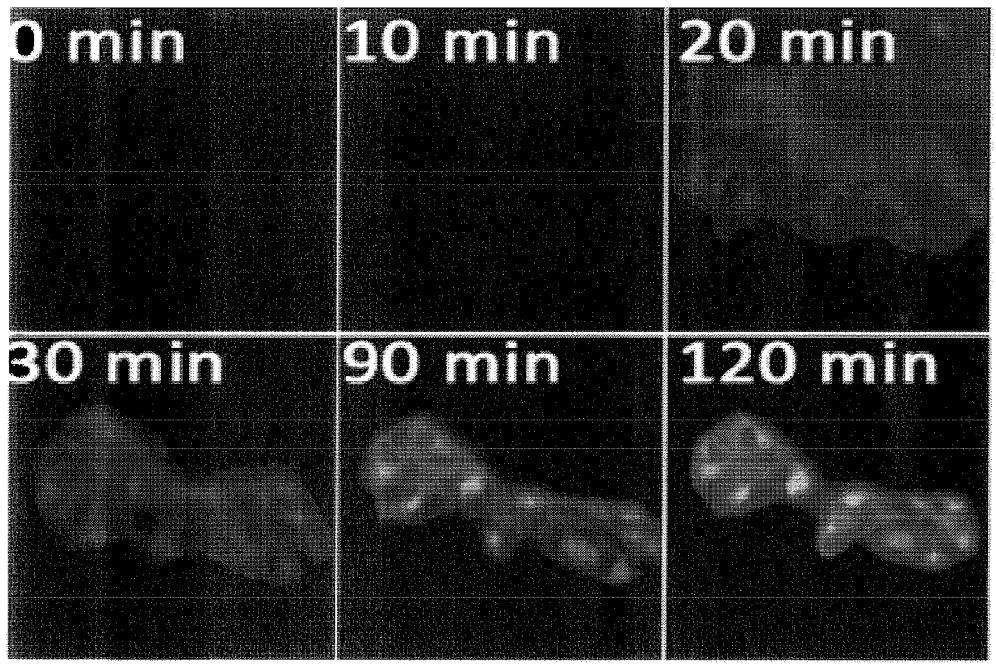
FIG. 37. Time course of confocal fluorescence real time images of HEK293T cells with conjugated nanoparticles.
Figure 38:
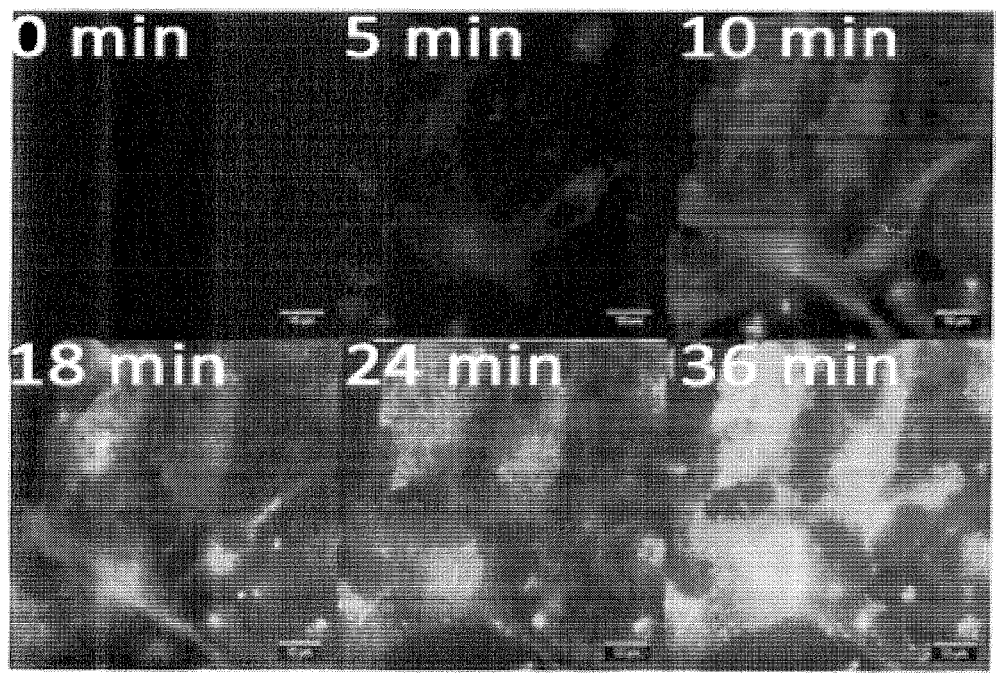
FIG. 38. Time course of confocal fluorescence real time images of CAKI-1 cells with conjugated nanoparticles.

In FIGS. 37 and 38 six static frames of the particle uptake obtained by real time imaging of HEK297T and CAKI-1 cells co-incubated with fluorophore conjugated particles are shown. It is clear that the intracellular fluorescence intensity increases over time as the particles are taken up by the cells but also that the extracellular particles are relatively non-fluorescent (dark background).

Figure 39:
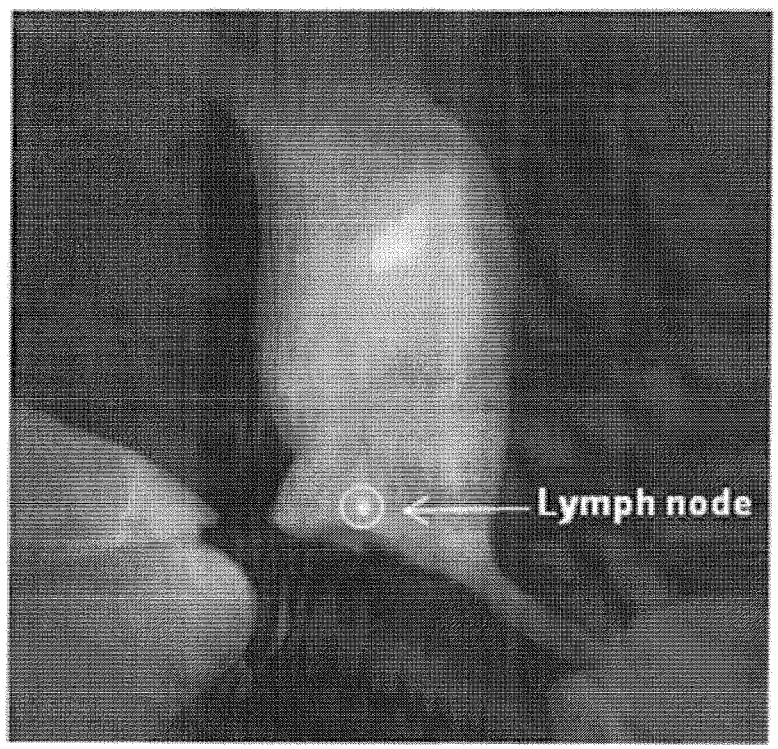
FIG. 39. In vivo fluorescence lymph node imaging taken 30 seconds after intra-dermal injection of dye conjugated particles in the left foot of the mouse.

In FIG. 39, an example of in vivo nano particle imaging is illustrated. It was possible to image the lymphatic node of a mouse following intra-dermal injection of dye conjugated particles in the left foot of the mouse. The closest lymph node from the injection site was successfully imaged immediately after the injection was performed.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described which may be varied in construction and detail without departing from the spirit of the invention.

The invention claimed is:

1. A compound of formula (I)

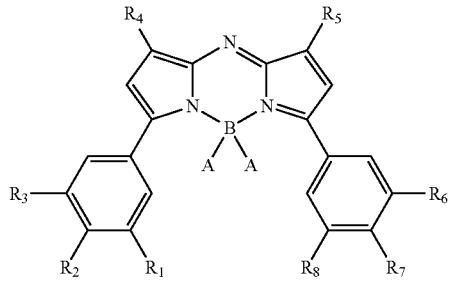

in which each A, which may be the same or different, is a halide selected from fluoride, chloride, bromide and iodide, or is O-Y, wherein Y is a substituted or unsubstituted, saturated or unsaturated, straight or branched chain alkyl moiety;

R$_1$, R$_2$, R$_3$, R$_6$, R$_7$, and R$_8$ are each independently H, OH, NO$_2$ or O-L-X, wherein L is a spacer group, and X is a conjugation group or a water-solubilizing group; with the proviso that at least one of R$_1$, R$_2$, R$_3$ is OH or O-L-X and at least one of R$_6$, R$_7$, and R$_8$ is OH or O-L-X; and each of R$_4$ and R$_5$ is phenyl.

2. A compound according to claim 1, wherein A is a halide.

3. A compound according to claim 1 and having a formula (IA),

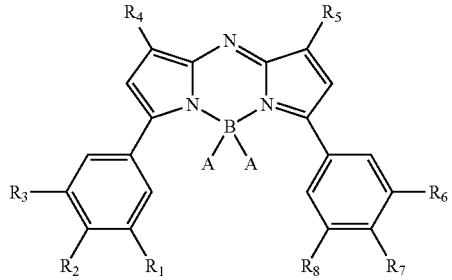

wherein R$_1$, R$_2$, R$_3$, R$_6$, R$_7$, and R$_8$ are each independently H, OH, NO$_2$ or O-L-X, with the further proviso that at least one of R$_1$, R$_2$, R$_3$, R$_6$, R$_7$, and R$_8$ is O-L-X.

4. A compound according to claim 3, wherein only one of R$_1$, R$_2$, R$_3$ is OH or O-L-X, and the remaining groups of R$_1$, R$_2$ and R$_3$ are each independently H or NO$_2$.

5. A compound according to claim 3, wherein only one of R$_6$, R$_7$, and R$_8$ is OH or O-L-X, and the remaining groups of R$_6$, R$_7$, and R$_8$ are each independently H or NO$_2$.

6. A compound according to claim 4, wherein when one of R$_1$, R$_2$, R$_3$ is OH or O-L-X, the remaining groups of R$_1$, R$_2$ and R$_3$ are each independently H.

7. A compound according to claim 5, wherein when one of R$_6$, R$_7$, and R$_8$ is OH or O-L-X, the remaining groups of R$_6$, R$_7$, and R$_8$ are each independently H.

8. A compound having a formula (IA),

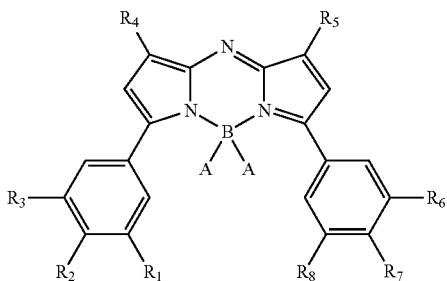

in which each A, which may be the same or different, is a halide selected from fluoride, chloride, bromide and iodide, or is O-Y, wherein Y is a substituted or unsubstituted, saturated or unsaturated, straight or branched chain alkyl moiety;

$R_1$, $R_2$, $R_3$, $R_6$, $R_7$ and $R_8$ are each independently H, OH, $NO_2$ or O-L-X, with the proviso that only one of $R_1$, $R_2$ and $R_3$ is O-L-X and only one of $R_6$, $R_7$, and $R_8$ is OH, wherein L is a spacer group and X is a conjugation group or a water-solubilizing group, and $R_4$ and $R_5$, which may be the same or different, are each independently H; or are a substituted or unsubstituted, saturated or unsaturated, cyclic moiety; a substituted or unsubstituted, saturated or unsaturated heterocyclic moiety; or a substituted or unsubstituted, saturated or unsaturated, straight or branched chain alkyl moiety.

9. A compound having a formula (IA),

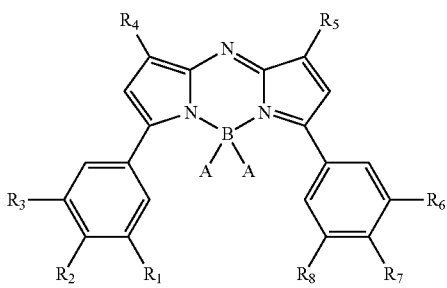

in which each A, which may be the same or different, is a halide selected from fluoride, chloride, bromide and iodide, or is O-Y, wherein Y is a substituted or unsubstituted, saturated or unsaturated, straight or branched chain alkyl moiety;

$R_1$, $R_2$, $R_3$, $R_6$, $R_7$ and $R_8$ are each independently H, OH, $NO_2$ or O-L-X, with the proviso that only one of $R_1$, $R_2$ and $R_3$ is OH and only one of $R_6$, $R_7$, and $R_8$ is O-L-X, wherein L is a spacer group and X is a conjugation group or a water-solubilizing group, and $R_4$ and $R_5$, which may be the same or different, are each independently H; or are a substituted or unsubstituted, saturated or unsaturated, cyclic moiety; a substituted or unsubstituted, saturated or unsaturated heterocyclic moiety; or a substituted or unsubstituted, saturated or unsaturated, straight or branched chain alkyl moiety.

10. A compound according to claim 3, wherein when only one of $R_1$, $R_2$ and $R_3$ is O-L-X and only one of $R_6$, $R_7$, and $R_8$ is O-L-X, wherein:
(a) each X is a conjugation group; or
(b) each X is a water-solubilizing group; or
(c) one X is a conjugation group and the other X is a water-solubilizing group.

11. A compound having a formula (IA),

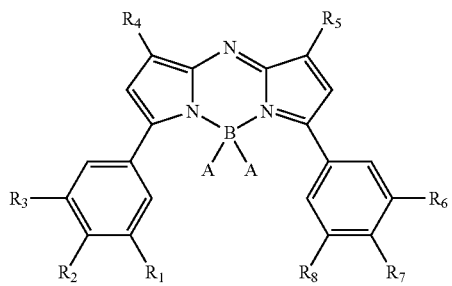

in which each A, which may be the same or different, is a halide selected from fluoride, chloride, bromide and iodide, or is O-Y, wherein Y is a substituted or unsubstituted, saturated or unsaturated, straight or branched chain alkyl moiety;

$R_1$ is H, $R_2$ is O-L-X, $R_3$ is H, $R_6$ is H, $R_7$ is O-L-X and $R_8$ is H, wherein one X is a conjugation group and the other X is a water-solubilizing group, and $R_4$ and $R_5$, which may be the same or different, are each independently H; or are a substituted or unsubstituted, saturated or unsaturated, cyclic moiety; a substituted or unsubstituted, saturated or unsaturated heterocyclic moiety; or a substituted or unsubstituted, saturated or unsaturated, straight or branched chain alkyl moiety.

12. A compound according to claim 11, wherein each A is F, $R_1$ is H, $R_2$ is O-L-X, $R_3$ is H, $R_4$ is Ph, $R_5$ is Ph, $R_6$ is H, $R_7$ is O-L-X and $R_8$ is H, wherein one X is a conjugation group and the other X is a water-solubilizing group.

13. A compound according claim 1, wherein L is a moiety selected from substituted or unsubstituted, saturated or unsaturated, straight or branched chain alkyls, methylenes, amines, amides and ethers, or derivatives thereof.

14. A compound according to claim 13, wherein the amine moiety is —$(CH_2)_2NH$—.

15. A compound according to claim 13, wherein the amide moiety is selected from $(CH_2)_2NHCO(CH_2)$—, —$(CH_2)_2NHCO(CH_2)_2$— and —$CONH(CH_2)_2NHCO(CH_2)_2$.

16. A compound according to claim 13, wherein ether moiety is $CH_2CH_2OCH_2CH_2$—.

17. A compound according to claim 1, wherein a conjugation group is a moiety selected from a carboxylic acid, an amine, an alkyne, a succinimidyl ester, an azide, an acyl azide, a maleimide, a diarylphosphonyl-aryl ester and biotin, or derivatives thereof.

18. A compound according to claim 17, wherein a diarylphosphonyl-aryl ester is ortho-diarylphosphonyl-aryl-methyl ester.

19. A compound according to claim 1, wherein a water-solubilizing group is a moiety selected from a carboxylic acid, an amine, a sulfonic acid, an alcohol, an ether, a polyether, an amide, a sulphonamide and a tetrazole, or derivatives thereof.

20. A compound of formula (I),

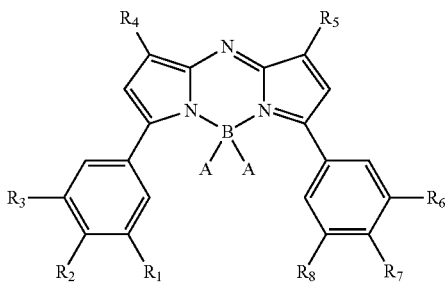

in which each A, which may be the same or different, is a halide selected from fluoride, chloride, bromide and iodide, or is O-Y, wherein Y is a substituted or unsubstituted, saturated or unsaturated, straight or branched chain alkyl moiety;

$R_1$, $R_2$, $R_3$, $R_6$, $R_7$ and $R_8$ are each independently H, OH, $NO_2$ or O-L-X, with the proviso that one of $R_1$, $R_2$ and $R_3$ is O-L-X and one of $R_6$, $R_7$, and $R_8$ is O-L-X, wherein L is a spacer group, one X is a sulfonic acid moiety and the other X is a succinimidyl ester moiety, and $R_4$ and $R_5$, which may be the same or different, are each independently H; or are a substituted or unsubstituted, saturated or unsaturated, cyclic moiety; a substituted or unsubstituted, saturated or unsaturated heterocyclic moiety; or a substituted or unsubstituted, saturated or unsaturated, straight or branched chain alkyl moiety.

21. A compound according to claim 20, wherein one of $R_1$, $R_2$ and $R_3$ is O-L-X, and O-L-X is O—$(CH_2)_3$—$SO_3Na$ or O—$(CH_2)_3$—$SO_3H$ or O—$(CH_2)_3$—$SO_3^-$, and one of $R_6$, $R_7$, and $R_8$ is O-L-X, and O-L-X is O—$CH_2$-succinimidyl ester or O—$(CH_2)_2NHCO(CH_2)_2$-succinimidyl ester or O—$CONH(CH_2)_2NHCO(CH_2)_2$-succinimidyl ester.

22. A compound according to claim 20, wherein one of $R_6$, $R_7$, and $R_8$ is O-L-X, and O-L-X is O—$(CH_2)_3$—$SO_3Na$ or O—$(CH_2)_3$—$SO_3^-$, and one $R_1$, $R_2$ and $R_3$ is O-L-X, and O-L-X is O—$CH_2$-succinimidyl ester or O—$(CH_2)_2NHCO(CH_2)_2$-succinimidyl ester or O—$CONH(CH_2)_2NHCO(CH_2)_2$-succinimidyl ester.

23. A compound according to claim 20, wherein each A is F, $R_4$ is Ph and $R_5$ is Ph.

24. A compound according to claim 1, wherein when two carboxylic acids or two amines or one carboxylic acid moiety and amine moiety are X, one of the two functions as a conjugation group and the other as a water-solubilizing group.

25. A compound according to claim 1, wherein where more than one ether group is present, one or more of the ether groups present provide the function of a spacer group.

26. A compound according to claim 1, wherein the compounds have a maximum absorbance $\lambda_{max}$ at greater than 660 nm, preferably greater than 670 nm, and a maximum emission at greater than 690 nm, preferably greater than 720 nm.

27. A compound of claim 1 selected from the compounds shown in the table below; wherin each A is fluoride, $R_1$ is H, $R_3$ is H, $R_4$ is Ph, $R_5$ is Ph, and $R_8$ is H:

| Reference number of compound in Examples where applicable | $R^2$ | $R^6$ | $R^7$ |
|---|---|---|---|
| 2 (Example 2(A)) | OH | H | $OCH_2$—C≡CH |
| 9 (Example 3(B)) | $O((CH_2)_2O)_3CH_3$ | H | $O(CH_2)_2NHBoc$ |
| Variation of 9 (Example 3(A)) | $O((CH_2)_2O)_3CH_3$ | H | $O(CH_2)_2NH_2$ |
| 10 (Example 3(A)) | $O((CH_2)_2O)_3CH_3$ | H | $O(CH_2)_2NHCO(CH_2)_2CO_2H$ |
| 11a (Example 3(A)) | $O((CH_2)_2O)_3CH_3$ | H | $O(CH_2)_2NHCO(CH_2)_2$-C(=O)-O-N-succinimidyl |
| 11b (Example 3(A)) | $O((CH_2)_2O)_3CH_3$ | H | $O(CH_2)_2NHCO(CH_2)_2$-C(=O)-O-N-sulfosuccinimidyl ($SO_3^-$) |
| 16 (Example 4) | $OCH_2CO_2^-$ | H | $OCH_2CO_2^-$ |
| Variation of 16 (Example 4) | $OCH_2CO_2H$ | H | $OCH_2CO_2H$ |
| 17 (Example 4) | $O(CH_2)_3SO_3^-$ | H | $O(CH_2)_3SO_3^-$ |
| Variation of 17 (Example 4) | $O(CH_2)_3SO_3H$ | H | $O(CH_2)_3SO_3H$ |
| 26 (Example 6) | $OCH_2CH_2CH_2SO_3Na$ | H | $OCH_2$—C≡CH |
| — | $OCH_2CO_2H$ | H | $OCH_2$—C≡CH |
| — | $O(CH_2)_3SO_3Na$ | H | $O(CH_2)_2NH_2$ |
| — | $O(CH_2)_3SO_3Na$ | H | $OCH_2CO_2H$ |

| Reference number of compound in Examples where applicable | R² | R⁶ | R⁷ |
|---|---|---|---|
| — | O(CH₂)₃SO₃Na | H | OCH₂–C(=O)–O–N(succinimidyl) |
| 27 (Example 6) | O(CH₂)₃SO₃Na | H | OH |
| — | OCH₂CO₂H | H | OH |
| — | OCH₂CO₂H | NO₂ | OH |
| — | OCH₂–C(=O)–O–N(succinimidyl) | H | OH |
| — | O(CH₂)₃SO₃Na | H | OCONH(CH₂)₂NHCO(CH₂)₂–C(=O)–O–N(succinimidyl) |
| 28 (Example 6) | O(CH₂)₃SO₃Na | H | O(CH₂)₂NHCO(CH₂)₂–C(=O)–O–N(succinimidyl) |
| — | O(CH₂)₃SO₃Na | H | O(CH₂)₂NHCO(CH₂)₂–N(maleimidyl) |
| — | OCH₂–C(=O)–O–N(succinimidyl) | H | OCH₂–C(=O)–O–N(succinimidyl) |
| 29 (Example 6) | O((CH₂)₂O)₃CH₃ | H | O(CH₂)₂NHCO(CH₂)₂–N(maleimidyl) |
| 30 (Example 6) | O((CH₂)₂O)₃CH₃ | H | O(CH₂)₂NH– 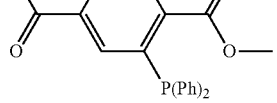 |

| Reference number of compound in Examples where applicable | $R^2$ | $R^6$ | $R^7$ |
|---|---|---|---|
| 31 (Example 6) | $O((CH_2)_2O)_3CH_3$ | H | 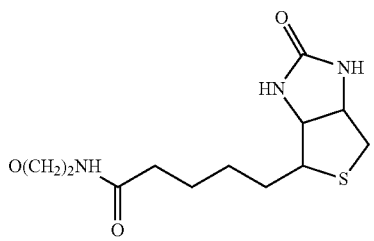 |

28. A compound according to claim 1 and having a formula (IB),

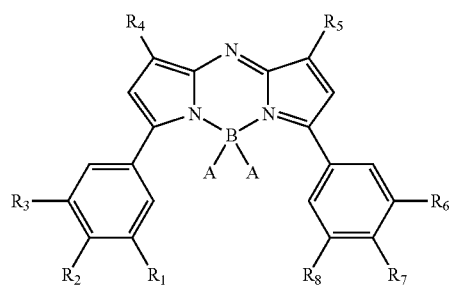

wherein $R_1$, $R_2$, $R_3$, $R_6$, $R_7$, and $R_8$ are each independently H, OH or $NO_2$; with the proviso that at least one of $R_1$, $R_2$, $R_3$ is OH and at least one of $R_6$, $R_7$, and $R_8$ is OH.

29. A compound according to claim 28, wherein only one of $R_1$, $R_2$, $R_3$ is OH, and the remaining groups of $R_1$, $R_2$, and $R_3$ are each independently H or $NO_2$.

30. A compound according to claim 28, wherein only one of $R_6$, $R_7$, and $R_8$ is OH, and the remaining groups of $R_6$, $R_7$, and $R_8$ are each independently H or $NO_2$.

31. A compound according to claim 28, wherein when one of $R_1$, $R_2$, $R_3$ is OH, the remaining groups of $R_1$, $R_2$, and $R_3$ are each independently H.

32. A compound according to claim 28, wherein when one of $R_6$, $R_7$, and $R_8$ is OH, the remaining groups of $R_6$, $R_7$, and $R_8$ are each independently H.

33. A compound according to claim 28, wherein $R_1$ is H, $R_2$ is OH, $R_3$ is H, $R_6$ is H, $R_7$ is OH and $R_8$ is H.

34. A compound according to claim 28, wherein each A is F, $R_1$ is H, $R_2$ is OH, $R_3$ is H, $R_4$ is Ph, $R_5$ is Ph, $R_6$ is H, $R_7$ is OH and $R_8$ is H.

* * * * *